(12) United States Patent
Crabtree et al.

(10) Patent No.: US 6,171,781 B1
(45) Date of Patent: Jan. 9, 2001

(54) NF-AT POLYPEPTIDES AND POLYNUCLEOTIDES

(75) Inventors: Gerald R. Crabtree, Woodside; Jeffrey P. Northrop, Cupertino; Steffan N. Ho, San Diego, all of CA (US)

(73) Assignee: The Board of Trustees of the Leland Stanford Junior University, Stanford, CA (US)

( * ) Notice: Under 35 U.S.C. 154(b), the term of this patent shall be extended for 0 days.

(21) Appl. No.: 09/049,691

(22) Filed: Mar. 27, 1998

Related U.S. Application Data

(63) Continuation-in-part of application No. 08/260,174, filed on Jun. 13, 1994, which is a continuation-in-part of application No. 08/124,981, filed on Sep. 20, 1993, now Pat. No. 5,837,840.

(51) Int. Cl.$^7$ ................ C12Q 1/00; C12Q 1/42; C12Q 1/48; G01N 33/53
(52) U.S. Cl. ................ 435/4; 435/7.1; 435/15; 435/21
(58) Field of Search ................ 435/4, 7.1, 15, 435/21

(56) References Cited

U.S. PATENT DOCUMENTS

| 5,612,455 | 3/1997 | Hoey | 530/350 |
| 5,656,452 | 8/1997 | Rao et al. | 435/69.1 |
| 5,708,158 | 1/1998 | Hoey | 536/23.5 |

FOREIGN PATENT DOCUMENTS

| WO 93/04203 | 3/1993 | (WO) . |
| WO 94/15964 | 7/1994 | (WO) . |
| WO 95/02053 | 1/1995 | (WO) . |
| WO 95/08554 | 3/1995 | (WO) . |
| WO 96/26959 | 6/1996 | (WO) . |

OTHER PUBLICATIONS

Clipstone, N. and Crabtree, G., "Calcineurin is a key signaling enzyme in T lymphocyte activation and the target of the immunosuppressive drugs cyclosporin A and FK506", *Ann. N.Y. Acad. Sci.*, 696: 20–30 (1993).

Clipstone, N. and Crabtree, G., "Identification of calcineurin as a key signaling enzyme in T–lymphocyte activation", *Nature*, 357(6380): 695–697 (1992).

Crabtree, G. and Clipstone, N., "Signal transmission between the plasma membrane and nucleus of T lymphocyte", *Ann. Rev. Biochem.*, 63: 1045–1083 (1994).

Ho, S. et al., "Cloning and characterization of NF–AT$_c$ and NF–AT$_p$: the cytoplasmic components of NF–At", *Adv. Exp. Med. Biol.* 365:167 (1994).

Jain, J. et al., "The T cell transcription factor NF–AT$_p$ is a substrate for calcineurin and interacts with Fos and Jun", *Nature*, 365(6444): 352–355 (1993).

Jain, J. et al., "Analysis of the preexisting and nuclear forms of nuclear factor of activated T cells", *J. Immunol.*, 151(2): 837–848 (1993).

Jain, J. et al., "Nuclear factor of activated T cells contains Fos and Jun", *Nature*, 356(6372): 801–804 (1992).

McCaffrey, P. et al., "NF–AT$_p$, a T lymphocyte DNA–binding protein that is a target for calcineurin and immunosuppresive drugs", *J. Biol. Chem.*, 268(5): 3747–3752 (1993).

McCaffrey, P. et al., "Isolation of the cyclosporin–sensitive T cell transcription factor NF–AT$_p$", *Science*, 262: 750–754 (1993).

Northrop, J. et al., "NF–AT components define a family of transcription factors targeted in T–cell activation", *Nature*, 369: 497–502 (1994).

Northrop et al. "Characterization of the nuclear and cytoplasmic components of the lymphoid–specific nuclear factor of activated T cells (NF–AT) complex" *J. Biol. Chem.* 268:2917 (1993).

Verweij, C. et al., "Cell type and activation requirements for NFAT–1 (nuclear factor of activated T–cells) transcriptional activity determined by a new method using transgenic mice to assay transcriptional activity of an individual nuclear factor", *J. Biol. Chem.*, 265(26): 15788–15795 (1990).

Rao, A., "NF–AT$_p$: a transcription factor required for the co–ordinate induction of several cytokine genes", *Immunology Today*, 15(6): 274–281 (1994).

Bierer, B. et al., "Two distinct signal transmission pathways in T lymphocytes are inhibited by complexes formed between an immunophilin and either FK506 or rapamycin", *Proc. Nat. Acad. Sci.* USA, 87: 9231–9235 (1990).

Flanagan, W. et al., "Nuclear association of T–cell transcription factor blocked by FK–506 and cyclosporin A", *Nature*, 352: 803–807 (1991).

(List continued on next page.)

*Primary Examiner*—Robert A. Schwartzman
(74) *Attorney, Agent, or Firm*—Foley, Hoag & Eliot, LLP; Isabelle M. Clauss; Matthew P. Vincent

(57) ABSTRACT

The invention provides novel polypeptides which are associated with the transcription complex NF-AT, polynucleotides encoding such polypeptides, antibodies which are reactive with such polypeptides, polynucleotide hybridization probes and PCR amplification probes for detecting polynucleotides which encode such polypeptides, transgenes which encode such polypeptides, homologous targeting constructs that encode such polypeptides and/or homologously integrate in or near endogenous genes encoding such polypeptides, nonhuman transgenic animals which comprise functionally disrupted endogenous genes that normally encode such polypeptides, and transgenic nonhuman animals which comprise transgenes encoding such polypeptides. The invention also provides methods for detecting T cells (including activated T cells) in a cellular sample, methods for treating hyperactive or hypoactive T cell conditions, methods for screening for immunomodulatory agents, methods for diagnostic staging of lymphocyte differentiation, methods for producing NF-AT proteins for use as research or diagnostic reagents, methods for producing antibodies reactive with the novel polypeptides, and methods for producing transgenic nonhuman animals.

90 Claims, 29 Drawing Sheets

OTHER PUBLICATIONS

Israel, A., "NF–AT comes under control ", *Nature*, 369: 443–444 (1994).

Crabtree G. "Pathways of T lymphocyte activation" Abstract of NIH Grant No. R01CA39612 (1988).

Crabtree G. "Pathways of T lymphocyte activation" Abstract of NIH Grant No. R01CA39612 (1991).

Shaw et al. "Identification of a putative regulator of early T cell activation genes" *Science* 241:202 (1988).

Crabtree G. "Contigent genetic regulatory events in T lymphocyte activation" *Science* 243:355 (1989).

Emmel et al. "Cyclosporin A specifically inhibits function of nuclear proteins involved in T cell activation" *Science* 246:1617 (1989).

Schmidt et al. "Inducible nulcear factor binding to the kB element of the human immunodeficiency virus enhancer in T cells can be blocked by cyclosporin A in a signal–dependent manner" *J. Virol.* 64:4037 (1990).

Mattila et al. "The actions of cyclosporin A and FK506 suggest a novel step in the activation of T lympocytes" *EMBO J.* 9:4425 (1990).

Banerji et al. "The immunosuppressant FK–506 specifically inhibits mitogen induced activation of the interleukin–2 promoter and the isolated enhancer elements NFIL–2A and NF–AT1" *Mol. Cell. Biol.* 11: 4074 (1991).

Riegel et al. "Nuclear events after activation of CD4+CD8+ thymocytes" *J. Immunol.* 144:3611(1990).

Beals, C. et al., "Nuclear Exports of NF–ATc Enhanced by Glycogen Synthase Kinase–3", *Science*, 275: 1930–1933 (Mar. 28, 1997).

Beals, C. et al., "Nuclear localization of NF–ATc by a calcineurin–dependent, cyclosporin–senstive intramolecular interaction", *Genes & Dev.*, 11: 824–834 (Apr. 1, 1997).

Ho, S. et al.,"NFATc3, a Lymphoid–specific NFATc Family Member That is Calcium–regulated and Exhibits Distinct DNA Binding Specificity", *J. Biol. Chem.*, 270(34): 19898–19907 (1995).

Hoye, T. et al., "Isolation of Two New Members of the NF–AT Gene Family and Functional Characterization of the NF–AT Proteins", *Immunity*, 2: 461–472 (1995).

Jain, J. et al., "A Similar DNA–binding Motif in NFAT Family Proteins and the Rel Homology Region", *J. Biol. Chem.*, 270:(8) 4138–4145 (1995).

Luo, C. et al., "Recombinant NFAT1 (NFATp) Is Regulated by Calcineurin in T Cells and Mediates Trascription of Several Cytokine Genes", *Mol. Cell. Biol.*, 16(7): 3955–3966 (1996).

Masuda, E. et al., "NFATx, a Novel Member of the Nuclear Factor of Activated T Cells Family That Is Expressed Predominantly in the Thymus", *Mol. Cell. Biol.*, 15(5): 2697–2706 (1995).

Rao, A., "NFATp, a cyclosporin–sensitive transcription factor implicated in cytokine gene induction", *J. Leukocyte Biol.*, 57:536–542 (1995).

Shibasaki, F. et al., "Role of kinases and the phosphatase calcineurin in the nuclear shuttling of transcription factor NF–AT4", *Nature*, 382: 370–3373 (1996).

Wolfe, S. et al., "Unusual Rel–like architecture in the DNA–binding domain of the transcription factor NFATc", *Nature*, 385:172–176 (1997).

```
          gaattccgcagggcgcgggcaccgggggcaggctcggagccgcagtcctaggccgcgcggccccgcacacgcccc
                  .         .         .         .         .         .         .
                 10        30        50        70        90       110       130       150       170       190 tcgatgactttcctccgggcgcgcggggctgagcccgggggctgtcttcccggagacccgaccgcagcgggcggccacttctcctgtg
                  .         .         .         .         .         .         .
                210       230       250       270       290 cctccgcccgctgctccactcccgccgccgcggaccagtttccagtccctccaagtttccacttgccctgcgctgcggtct
                  .         .         .         .         .         .
                      M  P  S  T  F  P  V  P  S  K  F  P  L  G  P  A  A  A  V  F      21
                310       330       350       370       390 tcggagaggagaaactttgggccgccggcgccaccatgaagtcagcggaggaagaacactatggctatgcatcctccaacgtcagccc
                  .         .         .         .         .         .
           G  R  G  E  T  L  G  P  A  P  R  A  G  G  T  M  K  S  A  E  E  E  H  Y  G  Y  A  S  S  N  V  S  P   54
          410       430       450       470       490 cgccctgccgctcccacggcgcactccaccctgccgccccaacctttcagacctgccacaacctcagacctccacaccgggcatcatcccgccggcgatcaccctcg
                  .         .         .         .         .         .
           A  L  P  L  P  T  A  H  S  T  L  P  A  P  C  H  N  L  Q  T  S  T  P  G  I  I  P  P  A  D  H  P  S   87
          510       530       550       570       590 gggtacggagcagctttggacggtgggccgccggccgggtactcctctccctcggccacaccaggctgatgggccctgcctgagagtcctgcatcg
                  .         .         .         .         .         .
           G  Y  G  A  A  L  D  G  G  P  A  G  Y  F  L  S  S  G  H  T  R  P  D  G  A  P  A  L  E  S  P  R  I  E  121
```

FIG. 1A

```
                     610              630              650              670              690
                      .                .                .                .                .
     agataacctcgtgcttggcctgtaccacaacaatacccagttttccacgatgtggaggtgaagacgtcctcccctagtccaaacgtccccctccac
122  I  T  S  C  L  G  L  Y  H  N  N  Q  F  F  H  D  V  E  V  E  D  V  L  P  S  S  K  R  S  P  S  T  154
                            710              730              750              770              790
                             .                .                .                .                .
     ggccacgctgagtctgccagcctggaggcctacagagacccctgtgcctgagcccggccagcctgtcctccgagctgcaactcagaggcctcc
155  A  T  L  S  L  P  S  L  E  A  Y  R  D  P  S  C  L  S  P  A  S  S  L  S  S  R  S  C  N  S  E  A  S  187
                            810              830              850              870              890
                             .                .                .                .                .
     tcctacgagtccaactactcgtacccgtacccccccagacgtcgccatggcagtctccctgcgtgtctccaagaccacgaccccgaggagggct
188  S  Y  E  S  N  Y  S  Y  P  Y  A  S  P  Q  T  S  P  W  Q  S  P  C  V  S  P  K  T  T  D  P  E  E  G  F  221
                            910              930              950              970              990
                             .                .                .                .                .
     ttccccggggctggggggctgcacactgctggttcccgcagcactccccctcccactgcccccgccagcgtcactgaggagagctggctggtgc
222  P  R  G  L  G  A  C  T  L  L  G  S  P  P  Q  H  S  P  S  T  S  P  R  A  S  V  T  E  E  S  W  L  G  A  254
                            1010             1030             1050             1070             1090
                             .                .                .                .                .
     ccgctcctccagacccgcgccagccccctgcaacagagaggaagtacagcctcaacggccgcagccagcctcctactaccccaccgcctcccg
255  R  S  S  R  P  A  S  P  C  N  K  R  K  Y  S  L  N  G  R  Q  P  P  Y  S  P  H  H  S  P  T  P  S  P  287
                            1110             1130             1150             1170             1190
                             .                .                .                .                .
     cacggctccccgcgggtcagcgtgaccgacgactctgtggcaacaccagtacaccaccagtcggccatcgtggccgcatcaacgcgctgacca
288  H  G  S  P  R  V  S  V  T  D  D  S  W  L  G  N  T  T  Q  Y  T  S  S  A  I  V  A  A  I  N  A  L  T  T  321

FIG. 1B
```

```
                                                                                                                             1210                    1230                    1250                    1270                    1290
                                                                                                                              .                       .                       .                       .                       .
       ccgacagagcctggacctgggagatggcgtccctgtcaagtcccgcaagaccacctggagcagccctcagtggcgctcaagtggagcccgtcgg
322    D  S  S  L  D  L  G  D  D  G  V  P  V  K  S  R  K  T  T  L  E  Q  P  P  S  V  A  L  K  V  E  P  V  G    354
                      1310                    1330                    1350                    1370                    1390 ggaggacctggggcagccccccgccgacttcgcgcccgaagactactctctttccagcacatcaggaaggcggcttctgcgaccagtacctg
355    E  D  L  G  S  P  P  P  P  A  D  F  A  P  E  D  Y  S  S  F  Q  H  I  R  K  G  G  F  C  D  Q  Y  L    387
                      1410                    1430                    1450                    1470                    1490 gcggtgccgcagcaccccctaccagtgggcagcaagcccaagcccctgtccctacgtctcctacatgagccgactcgccgcctgccactggcagctgccgt
388    A  V  P  Q  H  P  Y  Q  W  A  K  P  K  P  L  S  P  T  S  Y  M  S  P  T  L  P  A  L  D  W  Q  L  P  S    421
                      1510                    1530                    1550                    1570                    1590 cccactcaggccccgtatgagcttcggattgaggtccagccaagtcccaagtcccaccaccgagcccactacgagacgagcagccggggggcctgaaggcgtc
422    H  S  G  P  Y  E  L  R  I  E  V  Q  P  K  S  H  H  R  A  H  Y  E  T  E  G  S  R  G  A  V  K  A  S    454
                      1610                    1630                    1650                    1670                    1690 ggccggagagacacccatcgtgcagctcatgctacttggagaatgagccgctgatgctgcagtcttcattggagctgctgcagcttcaggacggcgacgacgcctgctgcgc
455    A  G  G  H  P  I  V  Q  L  H  G  Y  L  E  N  E  P  L  M  L  Q  L  F  I  G  T  A  D  D  R  L  L  R    487
                      1710                    1730                    1750                    1770                    1790 ccgcacgcttctaccaggtgcaccgcatcacagggaagaccgtgtccaccagccagcaccggaggccatatcctccaccaaagtcctggagatcccac
488    P  H  A  F  Y  Q  V  H  R  I  T  G  K  T  V  S  T  T  S  H  E  A  I  L  S  N  T  K  V  L  E  I  P  L    521
```

FIG. 1C

```
         1810              1830              1850              1870              1890
         tcctgccggagaacagcatgcgagccgtcattgactgtgccggaatcctgaaactcagaaactccgacattgaacttcggaaggagacggacatcgg   554
522      L P E N S M R A V I D C A G I L K L R N S D I E L R K G E T D I G
         1910              1930              1950              1970              1990 gaggaagaacacagggtacggctggtgttccgtcccgcaaccagcgccgacgctgtccctgcaggtcgcctccaacccatgaatgc   587
555      R K N T R V R L V F R V H V P Q P S G R T L S L Q V A S N P I E C
         2010              2030              2050              2070              2090 tcccagccgctcagtcaggagctgcctctggtggagaagcagcacggacagctatccggtcgtgggcggaagaagatggtcctgtctggccacaact   621
588      S Q R S A Q E L P L V E K Q S T D S Y P V V G G K K M V L S G H N F
         2110              2130              2150              2170              2190 tcctgcaggactccaaggtcatttttcgtggagaaagccccagatggccaccatgtctgggagatggaagcaaaactgaccgggacctgtcaagccgaa   654
622      L Q D S K V I F V E K A P D G H H V W E M E A K T D R D L C K P N
         2210              2230              2250              2270              2290 ttctctgtggttgagatccgccatttcggaatcagagaggataaccagcccgttcactgtctgcagttcttctacgtctgcaacggaaagagaagccag   687
655      S L V V E I P P F R N Q R I T S P V H V S F Y V C N G K R K R S Q
         2310              2330              2350              2370              2390 taccagcgtttcacctacctcccgccaacgtaacgccatctttctaaccgtaagccgtgaacatgagcgcgtggggtgtcttttctaaagacgcagaa   716
688      Y Q R F T Y L P A N G N A I F L T V S R E H E R V G C F F
```

FIG. 1D

```
                  2410              2430              2450              2470              2490
acgacgtcgccgtaaagcagcgtggcgtgttgcacattaactgtgtgattgatgtccgttagtgagaccgagccatcgatgcccgaaaaggaaaag
                  2510              2530              2550              2570              2590
ggaagcttcggatgcattttccttgatccctgttggggtgggggcgggggttgcatactcagatagtcacgttatttgcttcttgcaatgtataa
                  2610              2630              2650              2670              2690
cagccaaggggaaaacatggctcttctgctcccaaaaactgagggggtcctggtgtgcatttgcaccctaaagctgctacggtgaaaaggcaaataggt
                  2710              2730              2750
atagctattttgcaggcacctttaggaataaactttgcttttaaaaaaaa
```

FIG. 1E

```
DMDORSAL  TKNVRKKPYVKITE-IQPAGKALRFRYECEGRS-AGSIPGVNSTPENKT
C-REL     MASGLYNPYIEIIE-IQPRQRGMRFRYKCEGRS-AGSIPQEHSTDNNRT
NFKB p50  IPLSTDGPYLQILE-IQPKQRGFRFRYVCEGPSHGGLPGASSEKNKKS
NFKB p65  EPAQASGPYVEIIE-IQPKQRGMRFRYKCEGRS-AGSIPGERSTDTTKT
NFATc     QLPSHSGPYELRIEVQPKSH-HRAHYETEG-ISRGAVKASAGG----
NFATp     PLSNQSGSYELRIEVQPKPH-HRAHYETEG-ISRGAVKAPTGG----
          463                            *            502

DMDORSAL  YPTIEIVGYKGRAVVVVSCVTKDTPYRP-HPHNLVGKEGCK-KGVCTLEI
C-REL     YPSINIMNYYGRGKVRITLVTKNDPYKP-HPHDLVGKD-CR-DGYYEAEF
NFKB p50  YPQVKICNYVGPAKVIVQLVTNGKNIHL-HAHSLVGKH-CE-DGVCTVTA
NFKB p65  HPTIKINGYTGPGTVRISLVTKDPPHRP-HPHELVGKD-CR-DGYYEADL
NFATc     HPIVQLHGYLENEPLMLQLFIGTADDRLLRPHAFYQV-IHRITGKTVSTT
NFATp     HPVVQLHGYMENKPLGLQIFIGTADERILKPHAFYQV-IHRITGKTVTTT
          503                            *                 550

DMDORSAL  NSE-TMRAVFSNLGIQCVKKKDIEAALKAR-EEIRVDPFKTGFSHRF---
C-REL     GNE-RRPLFFQNLGIRCVKKKEVKEAHITRIKAG-INPFN---------
NFKB p50  GPK-DMVVGFANLGILHVT-KKKVFETLEARMTEACIRGYNPGLLVHSDL
NFKB p65  CPDRDSIHSFQNLGIQCVKKRDLEQAHS-QRIQTNNNPFH---------
NFATc     SHE-AILSNTKVLEIPLLPENSMRAVIDCAGILKLRNS-----------
NFATp     SYE-KIVGNTKVLEIPLEPKNNMRATIDCAGILKLRNA-----------
          551                            *             587
```

FIG. 4A

```
DMDORSAL  - - - - - - - - - - - - - - - - - - - - - - - - - - - - - - - - - - - - - - Q P S S I D L N S V R L C F Q V F M E S E Q K
C-REL     - - - - V P E K Q L N D I E - - - - - - - - - - - - - - - - - - - - - - - - - D C D L N V V R L C F Q V F L - P D E H
NFKB p50  A Y L Q A E G G G D R Q L T D R E K E I I R Q A A V Q T K E M D L S V V R L M F T A F L - P D S T
NFKB p65  - - - - - - - - - - - - - - - V P I E E - - - - - - - - - - Q R G D Y D L N A V R L C F Q V T V - R D P A
NFATc     - - - - - - - - - - - - - - - - - D I E - - - - - - - - - L R K G E T D I G R K N T R V R L V F R V H V - P Q P S
NFATp     - - - - - - - - - - - - - - - - - D I E - - - - - - - - - L R K G E T D I G R K N T R V R L V F R V H V - P E P S
                                          588                                                                  617

DMDORSAL  G R F T S P L P P V V S E P I F D K K A - - M S D L V H C R L - C S C S A T V F G N T Q I I L L C E
C-REL     G N L T T A L P P V V S N P I Y D N R A P N T A E L R H C R V - N K N C G S V R G G D E I F L L C D
NFKB p50  G S F T R R L E P V V S D A I Y D S K A P N A S N L K I V R M - D R T A G C V T G G E E I Y L L C D
NFKB p65  G R P L L - L T P V L S H P I F D N R A P N T A E L K I C R V - N R N S G S C L G G D E I F L L C D
NFATc     G R T L S - L - Q V A S N P I - - - - - - - E C S Q R S A Q E L P L V E K Q S T D S Y P V V G G K K M V L S - G
NFATp     G R I V S - L - Q A A S N P I - - - - - - - E C S Q R S A H E L P M V E R Q D M D S C L V Y G G Q Q M I L T - G
          618                                                                                              663

DMDORSAL  K V A K E D I S V R F F E E K N G Q - S V W E A F G D F Q H T D V H K Q T A I T F K T P R Y H T L D
C-REL     K V Q K D D I E V R F V L - - - - - - N D W E A K G I F S Q A D V H R Q V A I V F K T P P Y C K - A
NFKB p50  K V Q K D D I Q I R F Y E E E E N G - G V W E G F G D F S P T D V H R Q F A I V F K T P K Y K D V N
NFKB p65  K V Q K E D I E V Y F T G - - - - - - P G W E A R G S F S Q A D V H R Q V A I V F R T P P Y A D P S
NFATc     H N F L Q D S K V I F V E K A P D G H H V W E M E A K T - D R D L C K P N S L V V E I P P F R N Q R
NFATp     Q N F T A E S K V V F M E K T T D G Q Q I W E M E A T V - D K D K S Q P N M L F V E I P E Y R N K H
          664                                                                                              712

```
WT       CLSPASSLSSRSCNSEASSYESNYS   C
mSRR     --A--AA-AA-A--A--AA--A--A   N
184-194  ----------------A--AA--A--A N
172-176  --A--AA------------------   N
178-181  --------AA-A-------------   N
184-188  ------------A--AA--------   N
191-194  ----------------------A--A  C
```

NF-AT POLYPEPTIDES AND POLYNUCLEOTIDES

CROSS-REFERENCE TO RELATED APPLICATIONS

This application is a continuation-in-part of application Ser. No. 08/260,174, entitled "NF-AT *Polypeptides and Polynucleotides*", filed Jun. 13, 1994, which is a continuation-in-part of application Ser. No. 08/124,981, entitled "NF-AT *Polypeptides and Polynucleotides*", filed Sep. 20, 1993, U.S. Pat. No. 5,837,840. These applications are hereby incorporated by referenced herein.

This invention was made in the course of work supported by the U.S. Government and Howard Hughes Medical Institute, which may have certain rights in this invention.

FIELD OF THE INVENTION

The invention provides novel polypeptides which are associated with the transcription complex NF-AT, polynucleotides encoding such polypeptides, antibodies which are reactive with such polypeptides, polynucleotide hybridization probes and PCR amplification probes for detecting polynucleotides which encode such polypeptides, transgenes which encode such polypeptides, homologous targeting constructs that encode such polypeptides and/or homologously integrate in or near endogenous genes encoding such polypeptides, nonhuman transgenic animals which comprise functionally disrupted endogenous genes that normally encode such polypeptides, and transgenic nonhuman animals which comprise transgenes encoding such polypeptides. The invention also provides methods for detecting T cells (including activated T cells) in a cellular sample, methods for treating hyperactive or hypoactive T cell conditions, methods for screening for immunomodulatory agents, methods for diagnostic staging of lymphocyte differentiation, methods for producing NF-AT proteins for use as research or diagnostic reagents, methods for producing antibodies reactive with the novel polypeptides, and methods for producing transgenic nonhuman animals.

BACKGROUND OF THE INVENTION

The immune response is coordinated by the actions of cytokines produced from activated T lymphocytes. The precursors for most T lymphocytes arise in the bone marrow and migrate to the thymus where they differentiate and express receptors capable of interacting with antigen. These differentiated T lymphocytes then migrate to the peripheral lymphoid organs where they remain quiescent until they come in contact with the cognate antigen. The interaction of antigen with the antigen receptor on T lymphocytes initiates an ordered series of pleiotropic changes; a process denoted as T lymphocyte activation. T lymphocyte activation is a 7 to 10 day process that results in cell division and the acquisition of immunological functions such as cytotoxicity and the production of lymphokines that induce antibody production by B lymphocytes and control the growth and differentiation of granulocyte and macrophage precursors. The cytokines produced by activated T lymphocytes act upon other cells of the immune system to coordinate their behavior and bring about an effective immune response.

The initiation of T lymphocyte activation requires a complex interaction of the antigen receptor with the combination of antigen and self-histocompatibility molecules on the surface of antigen-presenting cells. T lymphocytes may also be activated by relatively simple stimuli such as the combination of a calcium ionophore (e.g., ionomycin) and an activator of protein kinase C, such as phorbol myristate acetate (PMA). Several lectins, including phytohemagglutinin (PHA) may also be used to activate T cells (Nowell (1960) *Cancer Res.* 20: 462).

T lymphocyte activation involves the specific regulation of particular subsets of genes. The transcriptional regulation characteristic of T cell activation begins minutes after the antigen encounter and continues until at least 10 days later. The T lymphocyte activation genes can be grouped according to the time after stimulation at which each gene is transcribed. Early genes are the first subset of T lymphocyte activation genes that is expressed during the activation process. Expression of the early genes triggers the transcriptional modulation of subsequent genes in the activation pathway. Because of the critical role of the T lymphocyte in the immune response, agents that interfere with expression of the early activation genes, such as cyclosporin A and FK506, are effective immunosuppressants.

Transcription of the early genes requires the presence of specific transcription factors, such as NF-AT, which in turn are regulated through interactions with the antigen receptor. These transcription factors are proteins which act through enhancer and promoter elements near the early activation genes to modulate the rate of transcription of these genes. Many of these transcription factors reversibly bind to specific DNA sequences located in and near enhancer elements.

The interleukin-2 (IL-2) gene is a paradigmatic early activation gene. The IL-2 gene product plays a critical role in T lymphocyte proliferation and differentiation. The IL-2 gene is transcriptionally active only in T cells that have been stimulated through the antigen receptor or its associated molecules (Cantrell and Smith (1984) *Science* 224: 1312). The transcriptional induction of IL-2 in activated T lymphocytes is mediated by a typical early gene transcriptional enhancer that extends from 325 basepairs upstream of the transcriptional start site for the IL-2 gene (Durand et al. (1988) *Mol. Cell. Biol.* 8: 1715). Other genes known to contain NF-AT recognition sites in their regulatory regions include: γ-interferon, IL-4, GM-CSF, and others. This region, which is referred to herein as the IL-2 enhancer, has been used extensively to dissect the requirements for T lymphocyte activation. An array of transcription factors, including NF-AT, NFkb, AP-1, Oct-1, and a newly identified protein that associates with Oct-1 called OAP-40, bind to sequences in this region (Ullman et al. (1991) *Science* 254: 558). These different transcription factors act together to integrate the complex requirements for T lymphocyte activation.

Among the group of transcription factors mentioned above, the presence of NF-AT is characteristic of the transcription events involving early activation genes, in that its recognition sequence is able to enhance transcription of linked heterologous genes in activated T cells of transgenic animals (Verweij et al. (1990) *J. Biol. Chem.* 265: 15788). The NF-AT sequence element is also the only known transcriptional element in the IL-2 enhancer that has no stimulatory effect on transcription in the absence of physiologic activation of the T lymphocyte through the antigen receptor or through treatment of T cells with the combination of ionomycin and PMA. For example, the NF-AT element enhances transcription of linked sequences in T lymphocytes which have had proper presentation of specific antigen by MHC-matched antigen presenting cells or have been stimulated with the combination of ionomycin/PMA, but not in unstimulated T lymphocytes (Durand et al. (1988) op.cit; Shaw et al. (1988) op.cit; Karttunen and Shastri (1991) *Proc.*

Natl. Acad. Sci. USA 88: 3972; Verweij et al. (1990) op.cit). Moreover, the NF-AT sequence element naturally enhances transcription of the IL-2 gene only in activated T lymphocytes.

Other elements within the IL-2 enhancer, for example, the NFkb site or the AP-1 site, activate transcription in response to less specific stimuli, such as tumor necrosis factor α or simply PMA by itself These compounds do not by themselves activate transcription of the IL-2 gene and other early activation genes, and do not lead to T lymphocyte activation.

Such observations indicate that the expression of certain early genes, such as the interleukin-2 gene may be regulated by the protein complex NF-AT. Data have also indicated that a selective genetic deficiency of NF-AT produces severe combined immunodeficiency (SCID) (Chatilla et al. (1989) New Engl. J. Med. 320: 696).

One of the functional sequences in the IL-2 enhancer is a binding site for a multimeric protein complex, designated NF-AT (nuclear factor of activated T lymphocytes), that functions as a transcriptional regulator of IL-2, IL-4, and other early activation genes (Shaw et al. (1988) Science 241: 202). The NF-AT transcription complex is formed subsequent to a signal from the antigen receptor. Enhancement of transcription of genes adjacent to the NF-AT recognition site requires that the NF-AT complex bind to the recognition site (Shaw et al. (1988) op.cit). Although the molecular makeup of NF-AT is not fully defined, studies have reported that NF-AT can be reconstituted from a ubiquitous nuclear component that requires protein synthesis for induction and a T cell-specific constitutive cytoplasmic component, designated NF-AT, (Flanagan et al. (1991) Nature 352: 803). This cytoplasmic component, $NF-AT_c$, associates with the nucleus in response to calcium signalling in a manner that is inhibited by the immunosuppressive drugs cyclosporin A (CsA) and FK506. The nuclear component of NF-AT can be induced with PMA, is not sensitive to CsA or FK506, and can be seen in cells of non-T cell origin such as HeLa and Cos.

Northrop et al. (1993) J. Biol. Chem. 268: 2917 report that the nuclear component of NF-AT contains the phorbol ester-inducible transcription factor, AP-1 (Jun/Fos), and show that antisera to Fos (a component of AP-1) inhibits NF-AT binding to DNA containing a binding site for AP-1. Moreover, Northrop et al. show that NF-AT DNA binding can be reconstituted in vitro using semi-purified AP-1 proteins mixed with cytosol from T lymphocytes, presumably containing $NF-AT_c$. Northrop et al. also report partial purification of $NF-AT_c$ and report a molecular mass range of approximately 94 to 116 kD as estimated by SDS-polyacrylamide gel electrophoresis.

As noted above, cyclosporin A (CsA) and FK506 are capable of acting as immunosuppressants. These agents inhibit T and B cell activation, mast cell degranulation, and other processes essential to an effective immune response (Borel et al. (1976) Agents Actions 6: 468; Sung et al. (1988) J. Exp. Med. 168: 1539; Gao et al. Nature 336: 176). In T lymphocytes, these drugs disrupt a step in the signal transduction pathway(s) through which the binding of antigen to the T cell antigen receptor produces enhanced transcription of specific cytokine genes involved in the coordination of the immune response. Thus, these agents prevent T lymphocyte activation (Crabtree et al. (1989) Science 243: 355; Schreiber et al. (1989) Science 251:283; Hohman & Hutlsch (1990) New Biol. 2: 663) and act as immunosuppressants.

Putative intracellular receptors for FK506 and CsA have been described and found to be cis-trans prolyl isomerases (Fischer & Bang (1985) Biochim. Biophys. Acta 828: 39; Fischer et al. Nature 337: 476; Handschumacher et al. (1984) Science 226: 544; Lang & Schmid (1988) Nature 331: 453; Standaert et al. (1990) Nature 346: 671). Binding of the drugs inhibits isomerase activity; however, studies with other prolyl isomerase inhibitors (Bierer et al. (1990) Science 250: 556) and analysis of cyclosporin-resistant mutants in yeast suggest that the prevention of T lymphocyte activation results from formation of an inhibitory complex involving the drug and the isomerase (Bierer et al. (1990) Proc. Natl. Acad. Sci. U.S.A. 87: 9231; Tropschug et al. (1989) Nature 342: 953), and not from inhibition of the isomerase activity per se. CsA and FK-506 prevent T cell proliferation by inhibiting a calcium-dependent signalling event required for the induction of interleukin-2 transcription.

Calcineurin, a calmodulin-dependent protein phosphatase which occurs in various isoforms, has been identified as a critical component of T cell activation through the signal transduction pathway leading to transcriptional activation of NF-AT-dependent genes, such as lymphokine genes (Liu et al. (1991) Cell 66: 807; Clipstone and Crabtree (1992) Nature 357: 695; O'Keefe et al. (1992) Nature 357: 692).

Transcriptional enhancement involving NF-AT recognition sequences is completely blocked in T cells treated with efficacious concentrations of cyclosporin A or FK506, with little or no specific effect on transcriptional enhancement involving recognition sites for other transcription factors, such as AP-1 and NF-κB (Shaw et al.(1988) op.cit; Emmel et al. (1989) Science 246:1617; Mattila et al. (1990) EMBO J. 9: 4425). This blockage can be overcome, at least partially, by the expression of hyperphysiolgical amounts of calcineurin (Clipstone and Crabtree (1992) op.cit.).

Unfortunately, while both cyclosporin A and FK506 are potent immunosuppressive agents, both drugs possess detrimental properties. For example, cyclosporin elicits adverse reactions including renal dysfunction, tremors, nausea and hypertension. Indeed, for many years researchers have attempted to develop superior replacements, with FK506 being the most recent candidate. However, without understanding the mechanisms by which cyclosporin (or FK506) functions at the intracellular level, developing improved immunosuppressants represents an extremely difficult research effort with a limited likelihood of success.

Thus, there exists a significant need to understand the functional basis of T cell activation involving NF-AT, particularly with regard to the mechanism by which these immunosuppresants such as CsA and FK506 inhibit transcription of the early activation genes. With such knowledge, improved assays for screening drug candidates would be feasible, which could in turn dramatically enhance the search process. Modulation of the immune system, especially modulation of T cell activation, also may be effected by directly altering the amount or activity of NF-AT. The present invention fulfills these and other needs.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention provides several novel methods and compositions for modulating the immune response and for screening for modulators of the immune response. These methods utilize polynucleotide sequences encoding $NF-AT_c$ recombinant proteins and complementary polynucleotides which are substantially identical to NF-$AT_c$ polynucleotide sequences.

In one aspect of the invention, NF-$AT_c$ polypeptides and compositions thereof are provided. NF-$AT_c$ polypeptides comprise polypeptide sequences which are substantially identical to a sequence shown in FIG. 1 or a cognate NF-$AT_c$ gene sequence.

Nucleic acid sequences encoding NF-$AT_c$ are provided. The characteristics of the cloned sequences are given, including the nucleotide and predicted amino acid sequence in FIG. 1. Polynucleotides comprising these sequences can serve as templates for the recombinant expression of quantities of NF-$AT_c$ polypeptides, such as human NF-$AT_c$ and murine NF-$AT_c$. Polynucleotides comprising these sequences can also serve as probes for nucleic acid hybridization to detect the transcription and mRNA abundance of NF-$AT_c$ mRNA in individual lymphocytes (or other cell types) by in situ hybridization, and in specific lymphocyte populations by Northern blot analysis and/or by in situ hybridization (Alwine et al. (1977) *Proc. Natl. Acad. Sci. U.S.A.* 74: 5350) and/or PCR amplification and/or LCR detection. Such recombinant polypeptides and nucleic acid hybridization probes have utility for in vitro screening methods for immunomodulatory agents and for diagnosis and treatment of pathological conditions and genetic diseases, such as transplant rejection reactions, T cell-mediated immune responses, lymphocytic leukemias (e.g., T cell leukemia or lymphoma) wherein NF-AT activity contributes to disease processes, autoimmune disease, arthritis, and the like.

In one embodiment, candidate immunomodulatory agents are identified by their ability to block the binding of a NF-$AT_c$ polypeptide to other components of NF-AT (e.g., AP-1) and/or to block the binding of NF-AT to DNA having an NF-AT recognition site. The DNA preferably includes one or more NF-AT binding sites at which a NF-AT protein complex specifically binds. One means for detecting binding of a NF-AT protein comprising NF-$AT_c$ to DNA is to immobilize the DNA, such as by covalent or noncovalent chemical linkage to a solid support, and to contact the immobilized DNA with a NF-AT protein complex comprising a NF-$AT_c$ polypeptide that has been labeled with a detectable marker (e.g., by incorporation of radiolabeled amino acid). Such contacting is typically performed in aqueous conditions which permit binding of a NF-AT protein to a target DNA containing a NF-AT binding sequence. Binding of the labeled NF-AT to the immobilized DNA is measured by determining the extent to which the labeled NF-$AT_c$ polypeptide is immobilized as a result of a specific binding interaction. Such specific binding may be reversible, or may be optionally irreversible if a cross-linking agent is added in appropriate experimental conditions.

In one aspect, candidate immunomodulatory agents are identified as being agents capable of inhibiting (or enhancing) intermolecular binding between NF-$AT_c$ and other polypeptides which compriss a NF-AT complex (e.g., AP-1, JunB, etc.). The invention provides methods and compositions for screening libraries of agents for the capacity to interfere with binding of NF-$AT_c$ to other NF-AT polypeptide species under aqueous binding conditions. Typically, at least either NF-$AT_c$ and/or another NF-AT polypeptide species is labeled with a detectable label and intermolecular binding between NF-$AT_c$ and other NF-AT polypeptide species is detected by the amount of labeled species captured in NF-AT complexes and the like.

Based at least in part on the observation that NF-AT polypeptides comprise nuclear localization sequences, which allow NF-AT polypeptides to translocate to the nucleus in the presence of intracellular calcium, but which are shielded by forming intramolecular associations with other domains in the NF-AT polypeptide in the absence of calcium, the invention also provides methods for modulating the activity of NF-AT, by modulating translocation of NF-AT, such as by modulating intramolecular associations and shielding of a nuclear localization sequence (NLS). In addition, since the NLS of NF-AT form an intramolecular association with a phosphorylated domain of NF-AT, the invention provides methods for modulating NF-AT activity, comprising modulating NF-AT phosphorylation. Furthermore, since, as disclosed herein, NF-AT is phosphorylated by protein kinase A (PKA) and glycogen synthase kinase-3 (GSK-3), and dephosphorylated by calcineurin, the state of phosphorylation and thus activation of NF-AT, can be modulated by modulating the activity of these kinases and/or phosphatase. Also within the scope of the invention are compounds which modulate nuclear translocation of NF-AT, as well as screening assays for identifying additional compounds.

In one aspect, the present invention provides a method for identifying an agent that modulates phosphorylation of an NFAT, comprising contacting test agent with a mixture including GSK-3 kinase activity with an NFAT polypeptide, or portion thereof which is a substrate of the GSK-3 kinase activity, and determining the ability of the test agent to modulate the interaction of the GSK-3 kinase activity with the NFAT polypeptide and/or phosphorylation of the NFAT polypeptide by the GSK-3 kinase activity.

The subject assay can be carried out in as a cell-based assay, e.g., employing a recombinant GSK-3 kinase, NF-AT substrate and/or reporter gene, or in a cell-free format, e.g., using purified or semi-purified preparations of GSK-3 and the NF-AT substrate. The assay can be a simple competitive binding assay, or a kinase activity assay which detects the rate of phosphorylation of the substrate, or a nuclear translocation assay which detects the rate of nuclear localization of the substrate. In preferred embodiments, the subject method includes a further step of formulating a pharmaceutical preparation including one or more compounds identified in the subject assay.

Another aspect of the present invention provides a method for modulating NFAT phosphorylation, comprising contacting a cell expressing NFAT with an agent that modulates the phosphorylation of NFAT by GSK-3, e.g., using a GSK-3 inhibitor, especially an inhibitor which inhibits NFAT nuclear translocation.

Still another aspect of the present invention relates to peptide or peptidomimetic agents for modulating nuclear translocation of an NFAT protein, which agent corresponds to a portion of an NFAT protein involved in intramolecular association of nuclear localization signals. The present invention also provides a method for identifying compounds that modulate nuclear translocation of NFAT, comprising contacting a test agent with a an NFAT polypeptide, or portion thereof which includes a nuclear localization signal, and determining the ability of the test agent to bind to the nuclear localization sequence and/or alter the tertiary structure of a phosphorylated form of the nuclear localization sequence. As above, such assays can be carried out in cell-based and cell-free formats, e.g., as competitive binding assays or nuclear translocation assays. In one embodiment, changes in the conformation of the protein which are dependent on phosphorylation of the NLS sequences can be detected photometrically, such as by CD/ORD or other means for determining changes in tertiary structure The invention also provides antisense polynucleotides complementary to NF-ATC sequences which are employed to inhibit transcription and/or translation of the cognate mRNA species and thereby effect a reduction in the amount of the respective NF-$AT_c$ protein in a cell (e.g., a T lymphocyte of a patient). Such antisense polynucleotides can function as immunomodulatory drugs by inhibiting the formation of NF-AT protein required for T cell activation.

In a variation of the invention, polynucleotides of the invention are employed for diagnosis of pathological conditions or genetic disease that involve T cell neoplasms or T cell hyperfunction of hypofunction, and more specifically conditions and diseases that involve alterations in the structure or abundance of NF-$AT_c$ polypeptide, NF-$AT_c$ polynucleotide sequence, or structure of the NF-$AT_c$ gene or flanking region(s).

The invention also provides antibodies which bind to NF-$AT_c$ with an affinity of about at least $1\times10^7$ $M^{-1}$ and which lack specific high affinity binding for other proteins present in activated T cells. Such antibodies can be used as diagnostic reagents to identify T cells (e.g., activatable T cells) in a cellular sample from a patient (e.g., a lymphocyte sample, a solid tissue biopsy) as being cells which contain an increased amount of NF-$AT_c$ protein determined by standardization of the assay to be diagnostic for activated T cells. Frequently, anti-NF-$AT_c$ antibodies are included as diagnostic reagents for immunohistopathology staining of cellular samples in situ. Additionally, anti-NF-$AT_c$ antibodies may be used therapeutically by targeted delivery to T cells (e.g., by cationization or by liposome/immunoliposome delivery).

The invention also provides NF-$AT_c$ polynucleotide probes for diagnosis of neoplasia or immune status by detection of NF-$AT_c$ mRNA in cells explanted from a patient, or detection of a pathognomonic NF-$AT_c$ allele (e.g., by RFLP or allele-specific PCR analysis). A pathognomonic NF-$AT_c$ allele is an allele which is statistically correlated with the presence of a predetermined disease or propensity to develop a disease. Typically, the detection will be by in situ hybridization using a labeled (e.g., $^{32}$P, $^{35}$S, $^{14}$C, $^3$H, fluorescent, biotinylated, digoxigeninylated) NF-$AT_c$ polynucleotide, although Northern blotting, dot blotting, or solution hybridization on bulk RNA or poly $A^+$ RNA isolated from a cell sample may be used, as may PCR amplification using NF-$AT_c$-specific primers. Cells which contain an increased amount of NF-$AT_c$ mRNA as compared to standard control values for cells or cell types other than activated T cells or activatable T cells will be thereby identified as activated T cells or activatable T cells. Similarly, the detection of pathognomonic rearrangements or amplification of the NF-$AT_c$ locus or closely linked loci in a cell sample will identify the presence of a pathological condition or a predisposition to developing a pathological condition (e.g., cancer, genetic disease).

The present invention also provides a method for diagnosing T cell hypofunction of hyperfunction in a human patient, wherein a diagnostic assay (e.g., immunohistochemical staining of fixed lymphocytic cells by an antibody that specifically binds human NF-$AT_c$) is used to determine if a predetermined pathognomonic concentration of NF-$AT_c$ protein or NF-$AT_c$ mRNA is present in a biological sample from a human patient; if the assay indicates the presence of NF-$AT_c$ protein or NF-$AT_c$ mRNA at or above such predetermined pathognomonic concentration, the patient is diagnosed as having T cell hyperfunction or hypofunction condition, or transplant rejection and the like. Alternatively, T cell hypofunction or immunosuppression can be diagnosed by determining the level of nuclear and/or cytoplasmic NF-AT in a subject and comparing the level with that of a normal subject. In one embodiment, the level of nuclear and/or cytoplasmic NF-AT is determined after incubation of lymphocytes of a subject with a T cell activator. A lower level of nuclear NF-AT relative to the normal subject indicates that the subject is immunosuppressed. A similar method can be used to monitor the state of immunosuppression in a subject who is being treated with an immunosuppressive drug, e.g., cyclosporin A. This allows more optimal dosages of the immunosuppressive drug to be administered to the subject.

All publications and patent applications herein are incorporated by reference to the same extent as if each individual publication or patent application was specifically and individually indicated to be incorporated by reference.

BRIEF DESCRIPTION OF THE DRAWINGS

FIGS. 1A–1E shows the nucleotide sequence of the human NF-$AT_c$ cDNA (SEQ ID NO: 45) and the deduced amino acid seqeunce (SEQ ID NO: 46). N inicates that a seqeunce ambiguity is present.

FIGS. 4A–C shows homology in the Rel homology domain between NF-$AT_c$, NF-$AT_p$, and Rel family members. The protein sequences of murine NF-$AT_p$ and the Rel proteins Dorsal (the Drosophila axis-determining protein) (SEQ ID NO: 47), human c-Rel (SEQ ID NO: 48), NF-κB p50 (SEQ ID NO: 49), and NF-κB p65 (SEQ ID NO: 50) are aligned to the sequence of NF-$AT_c$ (SEQ ID NO: 51) and NF-ATp (SEQ ID NO: 52). Numbering is with respect to NF-$AT_c$. Identity to NF-$AT_c$, open boxes; similarity in known residue function or structure, shaded areas. Stars indicate regions in which NF-$AT_c$ has: 1) a charge reversal relative to the majority of other Rel proteins, or has 2) replaced a potential salt bridge residue with a histidine or other chelating residue. Lower portion shows a schematic of NF-$AT_c$ and NF-$AT_p$.

DETAILED DESCRIPTION OF THE INVENTION

Figure 2:
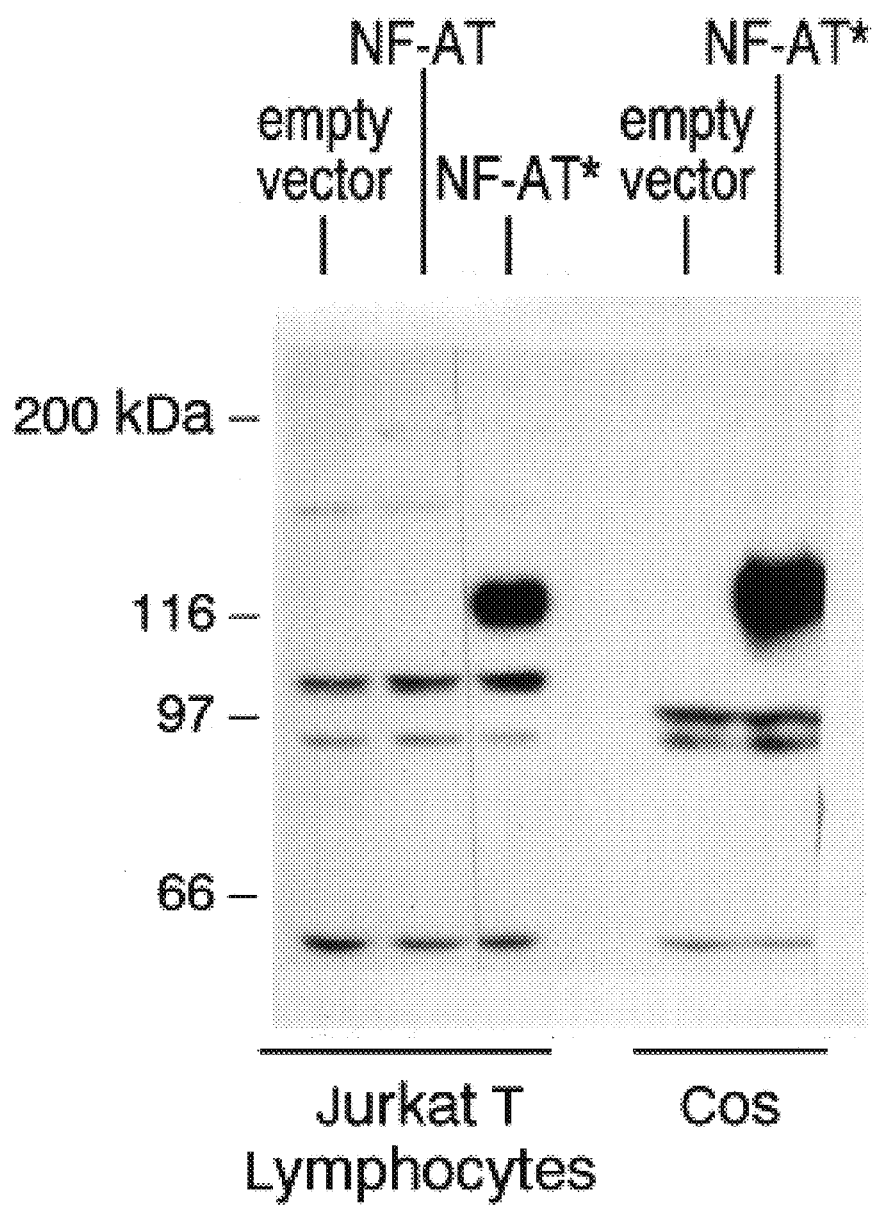
FIG. 2 shows the expression of NF-$AT_c$ protein in T cells (Jurkat) and non-T cells (Cos).

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. HA Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; PCR, eds. McPherson, Quirkes, and Taylor, IRL Press, Oxford; and U.S. Pat. No. 4,683,202, which are incorporated herein by reference).

Commonly assigned application U.S. Ser. No. 07/749,385 filed Aug. 22, 1991 is incorporated herein by reference.

1. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis*, 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction, sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparision; a reference sequence may be a subset of a larger sequence, for example, as a segment of a full-length cDNA or gene sequence given in a sequence listing, such as a polynucleotide sequence of FIG. 1, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (*U.S.A.*) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparision (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length human NF-AT$_c$ polynucleotide sequence shown in FIG. 1 or the full-length murine or bovine NF-AT$_c$ cDNA sequence.

As applied to polypeptides, a degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the NF-ATc sequences of the present invention. The term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "NF-AT$_c$ native protein" and "full-length NF-AT$_c$ protein" as used herein refers to a a naturally-occurring NF-AT$_c$ polypeptide corresponding to the deduced amino acid sequence shown in FIG. 1 or corresponding to the deduced amino acid sequence of a cognate full-length cDNA. Also for example, a native NF-AT$_c$ protein present in naturally-occurring lymphocytes which express the NF-AT$_c$ gene are considered full-length NF-AT$_c$ proteins.

The term "NF-AT$_c$ fragment" as used herein refers to a polypeptide that has an amino-terminal and/or carboxy-terminal deletion, but where the remaining amino acid sequence is identical to the corresponding positions in the NF-AT$_c$ sequence deduced from a full-length cDNA sequence (e.g., the cDNA sequence shown in FIG. 1). NF-AT$_c$ fragments typically are at least 14 amino acids long, preferably at least 20 amino acids long, usually at least 50 amino acids long or longer.

The term "NF-AT$_c$ analog" as used herein refers to polypeptides which are comprised of a segment of at least 25 amino acids that has substantial identity to a portion of the deduced amino acid sequence shown in FIG. 1, and which has at least one of the following properties: (1) binding to other polypeptides under suitable binding conditions including (a) other NF-AT proteins (e.g., AP-1); (b) a kinase, such as GSK-3 and PKA; (c) a phosphatase, such as calcineurin; (d) NF-AT polypeptides, in particular portions thereof, such as an NLS, SRR, SP1, SP2, and/or SP3; (2) binding to a nucleic acid; (3) ability to localize to the nucleus upon T cell activation; and (4) the ability to translocate from the nucleus to the cytoplasm after termination of the stimulatory signal. Typically, NF-AT$_c$ analog polypeptides comprise a conservative amino acid substitution (or addition or deletion) with respect to the naturally-occurring sequence. NF-AT$_c$ analogs typically are at least 20 amino acids long, preferably at least 50 amino acids long or longer, most usually being as long as full-length naturally-occurring NF-AT$_c$ (e.g., as shown in FIG. 1). Some NF-AT$_c$ analogs may lack biological activity but may still be employed for various uses, such as for raising antibodies to NF-AT$_c$ epitopes, as an immunological reagent to detect and/or purify α-NF-AT$_c$ antibodies by affinity chromatography, or as a competitive or noncompetitive agonist, antagonist, or partial agonist of native NF-AT$_c$ protein function.

The term "NF-AT$_c$ polypeptide" which is used herein interchangeably with the term "NF-AT" polypeptide, is used herein as a generic term to refer to native protein, fragments, or analogs of NF-AT$_c$. Hence, native NF-AT$_c$, fragments of NF-AT$_c$, and analogs of NF-AT$_c$ are species of the NF-AT$_c$ polypeptide genus. Preferred NF-AT$_c$ polypeptides include: the human full-length NF-AT$_c$ protein comprising the polypeptide sequence shown in FIG. 1 (which is also referred to as "NF-ATc1"), or polypeptides consisting essentially of a sequence shown in Table II. Thus, the genus NF-ATc includes all NF-AT polypeptides identified so far as well as those that have not yet been identified and which could be identified, e.g., by low stringency hybridization. In addition to the NF-ATc having SEQ ID NO: 38, which is also referred to as NF-ATc1, and homologs of other species, the NF-ATc genus includes NF-ATc2 (also termed NF-ATp), NF-ATc3 (also termed NF-AT4 or NF-ATx), NF-ATc4 (also termed NF-AT3), and splice variants thereof The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class I-restricted antigen recognition. Thus, the cognate murine gene to the human NF-AT$_c$ gene is the murine gene which encodes an expressed protein which has the greatest degree of sequence identity to the human NF-AT$_c$ protein and which exhibits an expression pattern similar to that of the human NF-AT$_c$ (e.g., expressed in T lineage cells). Preferred cognate NF-AT$_c$ genes are: rat NF-AT$_c$, rabbit NF-AT$_c$, canine NF-AT$_c$, nonhuman primate NF-AT$_c$, porcine NF-AT$_c$, bovine NF-AT$_c$, and hamster NF-AT$_c$.

The term "NF-AT$_c$-dependent gene" is used herein to refer to genes which: (1) have a NF-AT binding site (a site which can be specifically footprinted by NF-AT under suitable binding conditions) within about 10 kilobases of the first coding sequence of said gene, and (2) manifest an altered rate of transcription, either increased or decreased, from a major or minor transcriptional start site for said gene, wherein such alteration in transcriptional rate correlates with the presence of NF-AT$_c$ polypeptide in NF-AT complexes, such as in an activated T cell.

The term "altered ability to modulate" is used herein to refer to the capacity to either enhance or inhibit a biological activity, e.g., transcription of a gene; such enhancement or inhibition may be contingent on the occurrence of a specific event, such as T cell stimulation. For example, this alteration may be manifest as an inhibition of the transcriptional enhancement of the IL-2 gene that normally ensues following T cell stimulation. The altered ability to modulate transcriptional enhancement or inhibition may affect the inducible transcription of a gene, such as in the just-cited IL-2 example, or may effect the basal level transcription of a gene, or both.

The term "agent" is used to denote a chemical compound, a mixture of chemical compounds, a biological macromolecule, or an extract made from biological materials such as bacteria, plants, fungi, or animal (particularly mammalian) cells or tissues. Agents are evaluated for potential activity as immunomodulatory agents (e.g., immunosuppressants) by inclusion in screening assays described hereinbelow.

The term "candidate imunomodulatory agent" is used herein to refer to an agent which is identified by one or more screening method(s) of the invention as a putative immuomodulatory agent. Some candidate immunomodulatory agents may have therapeutic potential as drugs for human use.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, 35S, 125I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein the terms "pathognomonic concentration", "pathognomonic amount", and "pathognomonic staining pattern" refer to a concentration, amount, or localization pattern, respectively, of a NF-AT$_c$ protein or mRNA in a sample, that indicates the presence of a hypofunctional or hyperfunctional T cell condition or a predisposition to developing a disease, such as graft rejection. A pathognomonic amount is an amount of a NF-AT$_c$ protein or NF-AT$_c$ mRNA in a cell or cellular sample that falls outside the range of normal clinical values that is established by prospective and/or retrospective statistical clinical studies. Generally, an individual having a neoplastic disease (e.g., lymphocytic leukemia) or T cell-mediated immune response will exhibit an amount of NF-AT$_c$ protein or mRNA in a cell or tissue sample that is higher than the range of concentrations that characterize normal, undiseased individuals; typically the pathognomonic concentration is at least about one standard deviation above the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

2. NF-AT$_c$ Polynucleotides

Genomic or cDNA clones encoding NF-AT$_c$ may be isolated from clone libraries (e.g., available from Clontech, Palo Alto, Calif.) using hybridization probes designed on the basis of the nucleotide sequences shown in FIG. 1 and using conventional hybridization screening methods (e.g., Benton W D and Davis R W (1977) *Science* 196: 180; Goodspeed et al. (1989) *Gene* 76: 1;

Dunn et al. (1989) *J. Biol. Chem.* 264: 13057). Where a cDNA clone is desired, clone libraries containing cDNA derived from T cell mRNA is preferred. Alternatively, synthetic polynucleotide sequences corresponding to all or part of the sequences shown in FIG. 1 may be constructed by chemical synthesis of oligonucleotides. Additionally, polymerase chain reaction (PCR) using primers based on the sequence data disclosed in FIG. 1 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIG. 1 and a second primer that is not based on that sequence data may be used. For example, a second primer that is homologous to or complementary to a polyadenylation segment may be used. In an embodiment, a polynucleotide comprising the 2742 nucleotide long sequence of FIG. 1 can also be readily constructed by those of skill in the art by using the degeneracy of the genetic code. Polynucleotides encoding amino acids 418 to 710 of the NF-ATc sequence of FIG. 1 can also be constructed by those of skill in the art.

It is apparent to one of skill in the art that nucleotide substitutions, deletions, and additions may be incorporated into the polynucleotides of the invention. Nucleotide sequence variation may result from sequence polymorphisms of various NF-AT$_c$ alleles, minor sequencing errors, and the like. However, such nucleotide substitutions, deletions, and additions should not substantially disrupt the ability of the polynucleotide to hybridize to one of the polynucleotide sequences shown in FIG. 1 under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide having the sequence in FIG. 1), wherein the probe preferentially hybridizes to the specific target such that, for example, a single band corresponding to NF-AT$_c$ mRNA (or bands corresponding to multiple alternative splicing products of the NF-AT$_c$ gene) can be identified on a Northern blot of RNA prepared from a suitable cell source (e.g., a T cell expressing NF-AT$_c$). Polynucleotides of the invention and recombinantly produced NF-AT$_c$, and fragments or analogs thereof, may be prepared on the basis of the sequence data provided in FIG. 1 according to methods known in the art and described in Maniatis et al., *Molecular Cloning: A Laboratory Manual*, 2nd Ed., (1989), Cold Spring Harbor, N.Y. and Berger and Kimmel, *Methods in Enzymology. Volume* 152, *Guide to Molecular Cloning Techniques* (1987), Academic Press, Inc., San Diego, Calif., which are incorporated herein by reference.

NF-AT$_c$ polynucleotides may be short oligonucleotides (e.g., 25-100 bases long), such as for use as hybridization probes and PCR (or LCR) primers. NF-AT$_c$ polynucleotide sequences may also comprise part of a larger polynucleotide (e.g., a cloning vector comprising a NF-AT$_c$ clone) and may be fused, by polynucleotide linkage, in frame with another polynucleotide sequence encoding a different protein (e.g., glutathione S-transferase or β-galactosidase) for encoding expression of a fusion protein. Typically, NF-AT$_c$ polynucleotides comprise at least 25 consecutive nucleotides which are substantially identical to a naturally-occurring NF-AT$_c$ sequence (e.g., FIG. 1), more usually NF-AT$_c$ polynucleotides comprise at least 50 to 100 consecutive nucleotides which are substantially identical to a naturally-occurring NF-AT$_c$ sequence. However, it will be recognized by those of skill that the minimum length of a NF-AT$_c$ polynucleotide required for specific hybridization to a NF-AT$_c$ target sequence will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

For example but not limitation, suitable hybridization probes for detecting and/or quantifying the presence of NF-AT$_c$ mRNA in a sample generally comprise at least one, preferably at least two, and more preferably all of the following human NF-AT$_c$ sequences shown in Table I, or their complements:

TABLE I

Selected Human NF-AT Polynucleotide Sequences

5'-TTC CTC CGG GGC GCG CGG CGT GAG CCC GGG GCG AGG-3';      (SEQ ID NO: 1)

5'-CAG CGC GGG GCG GCC ACT TCT CCT GTG CCT CCG CCC GCT GCT-3';  (SEQ ID NO: 2)

5'-GCC GCG CGG ATG CCA AGC ACC AGC TTT CCA GTC CCT TCC AAG-3';  (SEQ ID NO: 3)

5'-CCA ACG TCA GCC CCG CCC TGC CGC TCC CCA CGG CGC ACT CCA-3';  (SEQ ID NO: 4)

5'-TTC AGA CCT CCA CAC CGG GCA TCA TCC CGC CGG CGG-3';       (SBQ ID NO: 5)

5'-GCC ACA CCA GGC CTG ATG GGG CCC CTG CCC TGG AGA GTC CTC-3';  (SEQ ID NO: 6)

5'-AGT CTG CCC AGC CTG GAG GCC TAC AGA GAC CCC TCG TGC CTG-3';  (SEQ ID NO: 7)

5'-GTG TCT CCC AAG ACC ACG GAC CCC GAG GAG GGC TTT CCC-3';    (SEQ ID NO: 8)

5'-AGC TGG CTG GGT GCC CGC TCC TCC AGA CCC GCG TCC CCT TGC-3';  (SEQ ID NO: 9)

5'-TAC AGC CTC AAC GGC CGG CAG CCG CCC TAC TCA CCC CAC CAC-3';  (SEQ ID NO: 10)

5'-GAC CAC CGA CAG CAG CCT GGA CCT GGG AGA TGG CGT CCC TGT-3';  (SEQ ID NO: 11)

5'-CCT GGG CAG CCC CCC GCC CCC GGC CGA CTT CGC GCC CGA AGA-3';  (SEQ ID NO: 12)

5'-GCT CCC CTA CCA GTG GCG AAG CCC AAG CCC CTG TCC CCT ACG-3';  (SBQ ID NO: 13)

5'-CTT CGG ATT GAG GTG CAG CCC AAG TCC CAC CAC CGA GCC CAC-3';  (SEQ ID NO: 14)

5'-CAT GGC TAC TTG GAG AAT GAG CCG CTG ATG CTG CAG CTT TTC-3';  (SEQ ID NO: 15)

5'-AAG ACC GTG TCC ACC ACC AGC CAC GAG GCT ATC CTC TCC AAC-3';  (SEQ ID NO: 16)

5'-TCA GCT CAG GAG CTG CCT CTG GTG GAG AAG CAG AGC ACG GAC-3';  (SEQ ID NO: 17)

5'-AAC GCC ATC TTT CTA ACC GTA AGC CGT GAA CAT GAG CGC G-3';   (SEQ ID NO: 18)

TABLE I-continued

Selected Human NF-AT Polynucleotide Sequences

5'-AGA AAC GAC GTC GCC GTA AAG CAG CGT GGC GTG TGG CA-3';  (SEQ ID NO: 19)

and

5'-GCA TAC TCA GAT AGT CAC GGT TAT TTT GCT TCT TGC GAA TG-3'. (SEQ ID NO: 20).

Also for example but not limitation, the following pair of PCR primers (amplimers) may be used to amplify murine or human NF-AT$_c$ sequences (e.g., by reverse transcriptase initiated PCR of RNA from NF-AT$_c$ expressing cells):
(forward)
5'-AGGGCGCGGGCACCGGGGCGCGGGCAGGG CTCGGAG-3' (SEQ ID NO: 21)
(reverse)
5'-GCAAGAAGCAAAATAACCGTGACTATCTGA GTATGC-3' (SEQ ID NO: 22)
If desired, PCR amplimers for amplifying substantially full-length cDNA copies may be selected at the discretion of the practioner. Similarly, amplimers to amplify single NF-AT$_c$ exons or portions of the NF-AT$_c$ gene (murine or human) may be selected.

Each of these sequences may be used as hybridization probes or PCR amplimers to detect the presence of NF-AT$_c$ mRNA, for example to diagnose a disease characterized by the presence of an elevated NF-AT$_c$ mRNA level in lymphocytes, or to perform tissue typing (i.e., identify tissues characterized by the expression of NF-AT$_c$ mRNA), and the like. The sequences may also be used for detecting, genomic NF-AT$_c$ gene sequences in a DNA sample, such as for forensic DNA analysis (e.g., by RFLP analysis, PCR product length(s) distribution, etc.) or for diagnosis of diseases characterized by amplification and/or rearrangements of the NF-AT$_c$ gene.

Disclosure of the full coding sequence for human NF-AT$_c$ shown in FIG. 1 makes possible the construction of isolated polynucleotides that can direct the expression of NF-AT$_c$, fragments thereof or analogs thereof Further, the sequences in FIG. 1 make possible the construction of nucleic acid hybridization probes and PCR primers that can be used to detect RNA and DNA sequences encoding NF-AT$_c$.

NF-AT polynucleotides of the invention include full-length NF-AT polynucleotides or portions thereof In one embodiment, the NF-AT polynucleotide is at least about 60%, 70%, 75%, 80%, 85%, 90%, 95%, more preferably at least about 98% and most preferably at least about 99% identical to a nucleotide sequence shown in FIG. 1 and set forth in SEQ ID NO: 45 or of a portion thereof Accordingly, the invention comprises polynucleotides encoding NF-ATc family members other than NF-ATc having SEQ ID NO: 38, which is referred to herein as NF-ATc1. Such family members include NF-ATc2 (also referred to as NF-ATp), NF-ATc3 (also referred to as NF-AT4 or NF-ATx), and NF-ATc4 (also referred to as NF-AT3) as well as differentially spliced forms thereof as described, e.g., in U.S. Pat. No. 5,612,455 issued to Hoey on Mar. 18, 1997 and U.S. Pat. No. 5,656,452, issued to Rao et al., on Aug. 12, published PCT WO 95/02035 by Arai et al. and WO 94/15964 by Rao et al.

Preferred portions or fragments of NF-ATc polynucleotides include those comprising one or more specific domains. At least the following NF-ATc domains have been identified: a DNA-binding domain, corresponding essentially to the Rel Homology Domain (RHD) or Rel Similary Domain (RSD), a domain interacting with another protein, e.g., AP-1 or a target site of PKA or GSK-3; a nuclear localization sequence (NLS), e.g., comprising amino acids 265–267 of SEQ ID NO: 38 (N-terminal NLS) or amino acids 681–685 of SEQ ID NO: 38 (C-terminal NLS), or a domain interacting with an NLS, e.g., SRR (amino acids 172–194 of SEQ ID NO: 38), SPI (amino acids 199–219 of SEQ ID NO: 38), SP2 (amino acids 233–252 of SEQ ID NO: 38), and SP3 (amino acids 278–301 of SEQ ID NO: 38). Other potential domains can be identified as further described herein. Accordingly, the invention provides NF-ATc polynucleotides encoding portions of NF-ATc polypeptides capable of exercising (agonists) or inhibiting (antagonists) at least one biological activity of NF-ATc, e.g., binding to another molecule, such as DNA or another protein, translocating across the nuclear membrane of a cell, or inhibiting translocation across a nuclear membrane of a cell. Assays for confirming, that an NF-AT polypeptide is an agonist or an antagonist of a specific biological activity of NF-AT are further described herein.

Other preferred nucleic acids of the invention encode an NF-ATc polypeptide or portion thereof, e.g., a portion corresponding to a certain domain or having a specific biological activity and polypeptides which are at least about 60%, 70%, 75%, 80%, 85%, 90%, 95%, more preferably at least about 98% and most preferably at least about 99% identical or similar to a portion of human NF-ATc set forth in SEQ ID NO: 38. For example, a preferred nucleic acid of the invention encodes an NF-AT polypeptide which is capable of modulating translocation across the nuclear membrane. The NF-AT polypeptide can include an NLS or a region of NF-ATc interacting therewith, such as a domain selected from the group consisting of SRR, SP1, SP2, and SP3. Furthermore, the polynucleotides of the invention can encode wild-type of mutated forms of NF-ATc polypeptides, such as those described in the Examples. For example, preferred polynucleotides encode an NF-ATc polypeptide having one or more serine that has been substituted with another amino acid, e.g., an alanine, to thereby prevent its phosphorylation. Preferred polypeptides encoded by the nucleic acids of the invention are further described herein, e.g., in the section pertaining to NF-AT polypeptides. Polynucleotides encoding full-length NF-AT$_c$ or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual,* 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a NF-AT$_c$ polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

A preferred NF-AT$_c$ polynucleotide encodes a NF-AT$_c$ polypeptide that comprises at least one of the following amino acids sequences:

-NAIFLTVSREHERVGC-(SEQ ID NO: 25);
-LHGYLENEPLNLQLFIGT-(SEQ ID NO: 26);
-PSTSPRASVTEESWLG-(SEQ ID NO: 27);
-GPAPRAGGTMKSAEEEHYG-(SEQ ID NO: 28);
-ASAGGHPIVQ-(SEQ ID NO: 29);
-NTRVRLVFRV-(SEQ ID NO: 30);
-AKTDRDLCKPNSLVVEIPPFRN-(SEQ ID NO: 31);
-EVQPKSHHRAHYETEGSR-(SEQ ID NO: 32);
-SPRVSVTDDSWLGNT-(SEQ ID NO: 33);
-SHHRAHYETEGSRGAV-(SEQ ID NO: 34);
-LRNSDIELRKGETDIGR-(SEQ ID NO: 35); and
-TLSLQVASNPIEC-(SEQ ID NO: 36).

The degeneracy of the genetic code gives a finite set of polynucleotide sequences encoding these amino acid sequences; this set of degenerate sequences may be readily generated by hand or by computer using commercially available software (Wisconsin Genetics Software Package Relaes 7.0). Thus, isolated polynucleotides typically less than approximately 10,000 nucleotides in length and comprising sequences encoding each of the following amino acid sequences:

-NAIFLTVSREHERVGC-(SEQ ID NO: 25);
-LHGYLENEPLMLQLFIGT-(SEQ ID NO: 26);
-PSTSPRASVTEESWLG-(SEQ ID NO: 27);
-GPAPRAGGTMKSAEEEHYG-(SEQ ID NO: 28);
-ASAGGHPIVQ-(SEQ ID NO: 29);
-NTRVRLVFRV-(SEQ ID NO: 30);
-AKTDRDLCKPNSLVVEIPPFRN-(SEQ ID NO: 31);
-EVQPKSHHRAHYETEGSR-(SEQ ID NO: 32);
-SPRVSVTDDSWLGNT-(SEQ ID NO: 33);
-SHHRAHYETEGSRGAV-(SEQ ID NO: 34);
-LRNSDIELRKGETDIGR-(SEQ ID NO: 35); and
-TLSLQVASNPIEC-(SEQ ID NO: 36).

are provided and may be used for, among other uses, the expression of a NF-AT$_c$ polypeptide which can be used as an imnmunogen, immunological reagent, and the like. Such polynucleotides typically comprise an operably linked promoter for driving expression in a suitable prokaryotic or eukaryotic host cell. One exemplification of such a polynucleotide is the human NF-AT$_c$ cDNA sequence of FIG. 1 cloned in operable linkage to the mammalian expression vector pSRα, many alternative embodiments will be apparent to those of skill in the art, including the use of alternative expression vectors (e.g., pBC12BI and p91023(B); Hanahan J (1983) *J. Mol. Biol.* 166: 577; Cullen et al. (1985) *J. Virol.* 53: 515; Lomedico PT (1982) *Proc. Natl. Acad. Sci. (U.S.A.)* 79: 5798; Morinaga et al. (1984) *Bio/Technology* 2: 636).

Additionally, where expression of a polypeptide is not desired, polynucleotides of this invention need not encode a functional protein. Polynucleotides of this invention may serve as hybridization probes and/or PCR primers (amplimers) and/or LCR oligomers for detecting NF-AT$_c$ RNA or DNA sequences.

Alternatively, polynucleotides of this invention may serve as hybridization probes or primers for detecting RNA or DNA sequences of related genes, such genes may encode structurally or evolutionarily related proteins. For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to the NF-AT$_c$ sequence is retained.

Specific hybridization is defined hereinbefore, and can be roughly summarized as the formation of hybrids between a polynucleotide of the invention (which may include substitutions, deletions, and/or additions) and a specific target polynucleotide such as human NF-AT$_c$ mRNA so that a single band is identified corresponding to each NF-AT$_c$ isoform on a Northern blot of RNA prepared from T cells (i.e., hybridization and washing conditions can be established that permit detection of discrete NF-AT$_c$ mRNA band(s)). Thus, those of ordinary skill in the art can prepare polynucleotides of the invention, which may include substantial additions, deletions, substitutions, or transpositions of nucleotide sequence as compared to sequences shown in FIG. 1 and determine whether specific hybridization is a property of the polynucleotide by performing a Northern blot using RNA prepared from a T lymphocyte cell line which expresses NF-AT$_c$ mRNA and/or by hybridization to a NF-AT$_c$ DNA clone (cDNA or genomic clone).

Specific amplification is defined as the ability of a set of PCR amplimers, when used together in a PCR reaction with a NF-AT$_c$ polynucleotide, to produce substantially a single major amplification product which corresponds to a NF-AT$_c$ gene sequence or mRNA sequence. Generally, human genomic DNA or mRNA from NF-AT$_c$ expressing human cells (e.g., Jurkat cell line) is used as the template DNA sample for the PCR reaction. PCR amplimers that exhibit specific amplification are suitable for quantitative determination of NF-AT$_c$ mRNA by quantitative PCR amplification. NF-AT$_c$ allele-specific amplification products, although having sequence and/or length polymorphisms, are considered to constitute a single amplification product for purposes of this definition.

Generally, hybridization probes comprise approximately at least 25 consecutive nucleotides of a sequence shown in FIG. 1 (for human and murine NF-AT$_c$ detection, respectively), preferably the hybridization probes contain at least 50 consecutive nucleotides of a sequence shown in FIG. 1, and more preferably comprise at least 100 consecutive nucleotides of a sequence shown in FIG. 1. PCR amplimers typically comprise approximately 25 to 50 consecutive nucleotides of a sequence shown in FIG. 1, and usually consist essentially of approximately 25 to 50 consecutive nucleotides of a sequence shown in FIG. 1 with additional nucleotides, if present, generally being at the 5' end so as not to interfere with polymerase-mediated chain extension. PCR amplimer design and hybridization probe selection are well within the scope of discretion of practioners of ordinary skill in the art.

3. Antisense Polynucleotides

Additional embodiments directed to modulation of T cell activation include methods that employ specific antisense polynucleotides complementary to all or part of the sequences shown in FIG. 1, as well as ribozymes and molecules forming triplex structures. Such complementary antisense polynucleotides may include nucleotide substitutions, additions, deletions, or transpositions, so long as specific hybridization to the relevant target sequence corresponding to FIG. 1 is retained as a functional property of the polynucleotide. Complementary antisense polynucleotides include soluble antisense RNA or DNA oligonucleotides which can hybridize specifically to NF-AT$_c$ mRNA species and prevent transcription of the mRNA species and/or translation of the encoded polypeptide (Ching et al. (1989) *Proc. Natl. Acad. Sci. U.S.A.* 86: 10006; Broder et al. (1990) *Ann. Int. Med.* 113: 604; Loreau et al. (1990) *FEBS Letters* 274: 53; Holcenberg et al., WO91/11535; U.S. Ser. No. 07/530,165 (U.S. Pat. No. 5,256,643); WO91/09865; WO91/04753; WO90/13641; and EP 386563, each of which is incorporated herein by reference). The antisense polynucleotides therefore inhibit production of NF-AT$_c$ polypeptides. Since NF-AT$_c$ protein expression is associated with T lymphocyte activation, antisense polynucleotides that prevent transcription and/or translation of mRNA corresponding to NF-AT$_c$ polypeptides may inhibit T cell activation and/or reverse the the activated phenotype of T cells. Compositions containing a therapeutically effective dosage of NF-AT$_c$ antisense polynucleotides may be administered for treatment of immune diseases, including lymphocytic leukemias, and for inhibition of transplant rejection reactions, if desired. Antisense polynucleotides of various lengths may be produced, although such antisense polynucleotides typically comprise a sequence of about at least 25 consecutive nucleotides which are substantially identical to a naturally-occurring NF-AT$_c$ polynucleotide sequence, and typically which are identical to a sequence shown in FIG. 1.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in the culture medium in vitro or in the circulatory system or interstitial fluid itt vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see *Antisense RNA and DNA*, (1988), D. A. Melton, Ed., Cold Spring Harbor Laboratory, Cold Spring Harbor, N.Y.).

4. Isolation of the Cognate Human NF-AT$_c$ Gene

The human homolog of the NF-AT$_c$ cDNA is identified and isolated by screening a human genomic clone library, such as a human genomic library in yeast artificial chromosomes, cosmids, or bacteriophage λ (e.g., λ Charon 35), with a polynucleotide probe comprising a sequence of about at least 24 contiguous nucleotides (or their complement) of the cDNA sequence shown in FIG. 1. Typically, hybridization and washing conditions are performed at high stringency according to conventional hybridization procedures. Positive clones are isolated and sequenced. For illustration and not for limitation, a full-length polynucleotide corresponding to the sequence of FIG. 1 may be labeled and used as a hybridization probe to isolate genomic clones from a human or murine genomic clone libary in λEMBL4 or λGEM11 (Promega Corporation, Madison, Wis.); typical hybridization conditions for screening plaque lifts (Benton and Davis (1978) *Science* 196: 180) can be: 50% formamide, 5×SSC or SSPE, 1–5×Denhardt's solution, 0.1–1% SDS, 100–200 μg sheared heterologous DNA or tRNA, 0–10% dextran sulfate, $1 \times 10^5$ to $1 \times 10^7$ cpm/ml of denatured probe with a specific activity of about $1 \times 10^8$ cpm/μg, and incubation at 42° C. for about 6–36 hours. Prehybridization conditions are essentially identical except that probe is not included and incubation time is typically reduced. Washing conditions are typically 1–3× SSC, 0.1–1% SDS, 50–70° C. with change of wash solution at about 5–30 minutes.

Nonhuman NF-AT$_c$ cDNAs and genomic clones (i.e., cognate nonhuman NF-AT$_c$ genes) can be analogously isolated from various nonhuman cDNA and genomic clone libraries available in the art (e.g., Clontech, Palo Alto, Calif.) by using probes based on the sequences shown in FIG. 1, with hybridization and washing conditions typically being less stringent than for isolation of human NF-AT$_c$ clones, Polynucleotides comprising sequences of approximately at least 30–50 nucleotides, preferably at least 100 nucleotides, corresponding to or complementary to the nucleotide sequences shown in FIG. 1 can serve as PCR primers and/or hybridization probes for identifying and isolating germline genes corresponding to NF-AT$_c$. These germline genes may be human or may be from a related mammalian species, preferably rodents or primates. Such germline genes may be isolated by various methods conventional in the art, including, but not limited to, by hybridization screening of genomic libraries in bacteriophage λ or cosmid libraries, or by PCR amplification of genomic sequences using primers derived from the sequences shown in FIG. 1. Human genomic libraries are publicly available or may be constructed de novo from human DNA.

Genomic clones of NF-AT$_c$, particularly of the murine cognate NF-ATc gene, may be used to construct homologous targeting constructs for generating cells and transgenic nonhuman animals having at least one functionally disrupted NF-AT$_c$ allele, preferably homozygous for knocked out NF-AT$_c$ alleles. Guidance for construction of homologous targeting constructs may be found in the art, including: Rahemtulla et al. (1991) *Nature* 353: 180; Jasin et al. (1990) *Genes Devel* 4: 157; Koh et al. (1992) *Science* 256: 1210; Molina et al. (1992) *Nature* 357: 161; Grusby et al. (1991) *Science* 253: 1417; Bradley et al. (1992) *Bio/Technology* 10: 534, incorporated herein by reference). Homologous targeting can be used to generate so-called "knockout" mice, which are heterozygous or homozygous for an inactivated NF-AT$_c$ allele. Such mice may be sold commercially as research animals for investigation of immune system development, neoplasia, T cell activation, signal transduction, drug sreening, and other uses.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference. Embryonicstem cells are manipulated according to published procedures (*Teratocarcinomas and Embryonic Stem Cells: A Practical Approach*, E. J. Robertson, ed., IRL Press, Washington, D.C. (1987); Zjilstra et al. (1989) *Nature* 342:435; and Schwartzberg et al. (1989) *Science* 246: 799, each of which is incorporated herein by reference).

Additionally, a NF-AT$_c$ cDNA or genomic gene copy may be used to construct transgenes for expressing NF-AT$_c$ polypeptides at high levels and/or under the transcriptional control of transcription control sequences which do not naturally occur adjacent to the NF-AT$_c$ gene. For example but not limitation, a constitutive promoter (e.g., a HSV-tk or pgk promoter) or a cell-lineage specific transcriptional regulatory sequence (e.g., a CD4 or CD8 gene promoter/enhancer) may be operably linked to a NF-AT$_c$-encoding polynucleotide sequence to form a transgene (typically in combination with a selectable marker such as a neo gene expression cassette). Such transgenes can be introduced into cells (e.g., ES cells, hematopoietic stem cells) and transgenic cells and transgenic nonhuman animals may be obtained according to conventional methods. Transgenic cells and/or transgenic nonhuman animals may be used to screen for antineoplastic agents and/or to screen for potential immunomodulatory agents, as overexpression of NF-$AT_c$ or inappropriate expression of NF-$AT_c$ may result in a hyperimmune state or enhance graft rejection reactions.

5. Expression of NF-$AT_c$ Polynucleotides

The nucleic acid sequences of the present invention capable of ultimately expressing the desired NF-$AT_c$ polypeptides can be formed from a variety of different polynucleotides (genomic or cDNA, RNA, synthetic oligonucleotides, etc.) as well as by a variety of different techniques.

As stated previously, the DNA sequences will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline resistance or hygromycin resistance, to permit detection and/or selection of those cells transformed with the desired DNA sequences (see, e.g., U.S. Pat. No. 4,704,362, which is incorporated herein by reference).

*E. coli* is one prokaryotic host useful particularly for cloning the DNA sequences of the present invention. Other microbial hosts suitable for use include bacilli, such as *Bacillus subtilis*, and other Enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, "From Genes to Clones," VCH Publishers, New York, N.Y. (1987), which is incorporated herein by reference). Eukaryotic cells are actually preferred, because a number of suitable host cell lines capable of secreting intact human proteins have been developed in the art, and include the CHO cell lines, various COS cell lines, HeLa cells, myeloma cell lines, Jurkat cells, etc. Expression vectors for these cells can include expression control sequences, such as an origin of replication, a promoter, an enhancer (Queen et al. (1986) *Immunol. Rev.* 89: 49, which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papillomavirus, and the like. The vectors containing the DNA segments of interest (e.g., polypeptides encoding a NF-$AT_c$ polypeptide) can be transferred into the host cell by well-known methods, which vary depending on the type of cellular host. For example, $CaCl$ transfection is commonly utilized for prokaryotic cells, whereas $CaPO_4$ treatment or electroporation may be used for other cellular hosts. (See, generally, Maniatis, et al., *Molecular Cloning: A Laboratory Manual*, Cold Spring Harbor Press, (1982), which is incorporated herein by reference). Usually, vectors are episomes and are maintained extrachromosomally.

Expression of recombinant NF-ATc protein in cells, particularly cells of the lymphopoietic lineage, may be used to identify and isolate genes that are transcriptionally modulated, either positively or negatively, by the presence of NF-$AT_c$ protein. Such genes are typically initially identified as cDNA clones isolated from subtractive cDNA libraries, wherein RNA isolated from cells expressing recombinant NF-ATc and RNA isolated from control cells (i.e., not expressing recombinant NF-ATc) are used to generate the subtractive libraries and screening probes. In such a manner, NF-$AT_c$-dependent genes may be isolated. NFAT-dependent genes (or their regulatory sequences operably linked to a reporter gene) may be used as a component of an in vitro transcription assay employing a NF-$AT_c$ polypeptide as a necessary component for efficient transcription; such transcription assays may be used to screen for agents which inhibit NF-$AT_c$-dependent gene transcription and are thereby identified as candidate immunomodulatory agents.

6. NF-$AT_c$ Polypeptides

The nucleotide and amino acid sequences shown in FIG. 1 enable those of skill in the art to produce polypeptides corresponding to all or part of the full-length human NF-$AT_c$ polypeptide sequence. Such polypeptides may be produced in prokaryotic or eukaryotic host cells by expression of polynucleotides encoding NF-$AT_c$, or fragments and analogs thereof Alternatively, such polypeptides may be synthesized by chemical methods or produced by iii vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.

Fragments or analogs of NF-$AT_c$ may be prepared by those of skill in the art. Preferred amino- and carboxy-termini of fragments or analogs of NF-$AT_c$ occur near boundaries of functional domains. For example, but not for limitation, such functional domains include: (1) domains conferring the property of binding to other NF-AT components (e.g., AP-1), (2) domains conferring the property of nuclear localization in stimulated T lymphocytes, and (3) domains conferring the property of enhancing activation of T cells when expressed at sufficient levels in such cells. Additionally, such functional domains might include: (1) domains conferring the property of binding to RNA polymerase species, (2) domains having the capacity to directly alter local chromatin structure, which may comprise catalytic activities (e.g., topoisomerases, endonucleases) and/or which may comprise structural features (e.g., zinc fingers, histone-binding moieties), and (3) domains which may interact with accessory proteins and/or transcription factors.

One method by which structural and functional domains may be identified is by comparison of the nucleotide and/or amino acid sequence data shown in FIG. 1 to public or proprietary sequence databases. Preferably, computerized comparison methods are used to identify sequence motifs or predicted protein conformation domains that occur in other proteins of known structure and/or function, such as the zinc fingers. For example, the NAD-binding domains of dehydrogenases, particularly lactate dehydrogenase and malate dehydrogenase, are similar in conformation and have amino acid sequences that are detectably homologous (*Proteins, Structures and Molecular Principles*, (1984) Creighton (ed.), W.H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the NF-AT$_c$ sequences of the invention. ne example of a domain is the rel similarity region from amino acid 418 to amino acid 710 of the NF-AT$_c$ polypeptide sequence of FIG. 1.

Additionally, computerized comparison of sequences shown in FIG. 1 to existing sequence databases can identify sequence motifs and structural conformations found in other proteins or coding sequences that indicate similar domains of the NF-AT$_c$ protein. For example but not for limitation, the programs GAP, BESTFIT, FASTA, and TFASTA in the Wisconsin Genetics Software Package (Genetics Computer Group, 575 Science Dr., Madison, Wis.) can be used to identify sequences in databases, such as GenBank/EMBL, that have regions of homology with a NF-AT$_c$ sequences. Such homologous regions are candidate structural or functional domains. Alternatively, other algorithms are provided for identifying such domains from sequence data. Further, neural network methods, whether implemented in hardware or software, may be used to: (1) identify related protein sequences and nucleotide sequences, and (2) define structural or functional domains in NF-AT$_c$ polypeptides (Brunak et al. (1991) *J. Mol. Biol.* 220: 49, which is incorporated herein by reference). For example, the 13-residue repeat motifs -SPRASVTEESWLG-(SEQ ID NO: 23) and -SPRVSVTDDSWLG-(SEQ ID NO: 24) are examples of structurally related domains.

Fragments or analogs comprising substantially one or more functional domain may be fused to heterologous polypeptide sequences, wherein the resultant fusion protein exhibits the functional property(ies) conferred by the NF-AT$_c$ fragment. Alternatively, NF-AT$_c$ polypeptides wherein one or more functional domain have been deleted will exhibit a loss of the property normally conferred by the missing fragment.

By way of example and not limitation, the domain conferring the property of nuclear localization and/or interaction with AP-1 may be fused to β-galactosidase to produce a fusion protein that is localized to the nucleus and which can enzymatically convert a chromogenic substrate to a chromophore.

Although one class of preferred embodiments are fragments having amino- and/or carboxy-termini corresponding to amino acid positions near functional domains borders, alternative NF-AT$_c$ fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs of NF-AT$_c$ can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to the native NF-AT$_c$ protein. However, NF-AT$_c$ analogs must comprise a segment of amino acids that has substantial similarity to a portion of the amino acid sequence shown in FIG. 1, respectively, and which has at least one of the requisite functional properties enumerated in the Definitions (supra). Preferred amino acid substitutions are those which: (1) reduce susceptibility to proteolysis, (2) reduce susceptibility to oxidation, (3) alter post-translational modification of the analog, possibly including phosphorylation, and (4) confer or modify other physicochemical or functional properties of such analogs, possibly including interaction with calcineurin or phophorylation or dephosphorylation thereby. NF-AT$_c$ analogs include various muteins of a NF-AT$_c$ sequence other than the naturally-occurring peptide sequence. For example, single or multiple amino acid substitutions (preferably conservative amino acid substitutions) may be made in the naturally-occurring NF-AT$_c$ sequence (preferably in the portion of the polypeptide outside the functional domains).

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles*, (1984) Creighton (ed.), W.H. Freeman and Company, New York; *Introduction to Protein Structure*, (1991), C. Branden and J. Tooze, Garland Publishing, New York, N.Y.; and Thornton et al. (1991) *Nature* 354: 105; which are incorporated herein by reference).

The invention further provides phosphorylated NF-AT polypeptides. Preferred phosphorylated polypeptides comprise at least one phosphoserine, which can be selected from the group consisting of serines located in the region from about amino acid 172 to about amino acid 301. Even more preferred NF-AT polypeptides comprise a phosphorylated serine in SRR, SP1, SP2, and/or SP3. Preferred serines in SRR include those at residues 172, 175, 176, 178, 179, 181, 184, 187,188, 192, and 194 of SEQ ID NO: 38. Preferred serines in SP I include those at residues 199, 203, 207, and 211 of SEQ ID NO: 38. Preferred serines in SP2 include those at residues 233, 327, and 245 of SEQ ID NO: 38. Preferred serines in SP3 include those at residues 278, 282, 286, 290, and 299 of SEQ ID NO: 38. Another preferred NF-AT polypeptide has a phosphoserine at position 269.

The invention also provides peptides and peptidomimetics, e.g., for use in modulating nuclear translocation of an NF-AT protein. In a preferred embodiment, the agent comprises a portion of an NF-AT protein that is involved in translocation of an NF-AT polypeptide across the nuclear membrane of a cell, e.g., a portion of an NF-AT polypeptide that forms an intramolecular association. In an even more preferred embodiment, the portion of NF-AT comprises a nuclear localization signal or sequence (NLS), such as the amino acid sequence KRKK (SEQ ID NO: 56) or KRKR (SEQ ID NO: 65) (referred to herein as KRKK/R (SEQ ID NO: 66)), corresponding to amino acids 682 to 685 of NF-ATc1 (SEQ ID NO: 38), or the amino acid sequence GKRKK/R (SEQ ID NO: 67), corresponding to amino acids 681–685 of SEQ ID NO: 38 or homologous sequences in other NF-ATc family members. In fact, this C-terminal NLS, is also found in the other NF-ATc family members (see, e.g., Hoey et al. (1995) Immunity 2:461): NF-ATp (NF-ATc2) C-terminal NLS has the sequence NGKRKRS (SEQ ID NO: 68) (see FIG. 4); NF-ATc3 (NF-AT4) C-terminal NLS has the sequence NGKRKKS (SEQ ID NO: 69); and NF-ATc4 (NF-AT3) C-terminal NLS has the sequence NGRRKRS (SEQ ID NO: 70) (see Hoey et al., supra). Accordingly, the invention provides peptides or peptidomimetics comprising these NLS. In another embodiment, the invention provides peptides and peptidomimetics comprising a nuclear localization signal including the amino acid sequence KRK, corresponding to amino acids 265–267 of NF-ATc1 (SEQ ID NO: 38). Alternatively, the peptide comprises the amino acid sequence CNKRKYSLN (SEQ ID NO: 53), corresponding to amino acids 263–271 of SEQ ID NO: 38.

The presence in a cell expressing NF-AT of a peptide comprising an NF-AT NLS will competitively inhibit the interaction of the endogenous NF-AT NLS with the SRR, SP1, SP2 and/or SP3 regions of NF-AT$_c$ thereby uncovering the NLS and allowing NF-AT to be translocated to the nucleus. Thus, the NF-AT NLS peptides of the invention constitute specific activators of NF-AT. In view of the sequence similarities between the NF-ATc family members, the intramolecular interaction between NLSs and other domains of the NF-ATc1 molecule set forth herein, are believed to occur in the other NF-ATc family members and to regulate their translocation across a nuclear membrane. The effect of these activators in a cell can be reversed by, e.g., introducing into the cell a peptide that is capable of interacting with an NF-AT NLS. For example, if a peptide comprising the NLS KRKK/R (SEQ ID NO: 66) is administered to a subject, the administration of a peptide capable of binding to this NLS will inhibit the activator.

Accordingly, the invention also provides peptides and peptidomimetics that are capable of interacting with an NLS in an NF-ATc molecule. Such peptides can be used, e.g., to stimulate translocation of NF-AT from the nucleus to the cytoplasm, by interacting with, and thereby shielding, the NLS of NF-AT molecules. Preferred peptides include N-terminal peptides, e.g., peptides located in the region from about amino acid 172–301 of SEQ ID NO: 38. Even more preferred peptides comprise one or more sequence from the group consisting of SRR, SP1, SP2, and SP3. In one embodiment, such a peptide comprises an amino acid sequence of an SRR sequence, e.g., corresponding to about amino acids 172–194 of SEQ ID NO: 38. Shorter peptides can also be used so long as they are capable of interacting with the NLS. Other peptides that can be used for this purpose include peptides comprising one or more sequences selected from the group consisting of SP1, SP2 and SP3, e.g., peptides comprising about amino acids 199–219 of SEQ ID NO: 38 (corresponding to SP1), about amino acids 233–252 of SEQ ID NO: 38 (SP2), and/or amino acids 278–301 of SEQ ID NO: 38 (SP3). Other peptides comprising amino acid sequence that are homologous (at least about 80%, 85%, 90%, 95%, or preferably at least about 98% or 99% identical or similar) to the SRR, SP1, SP2, and SP3 sequences set forth above are also within the scope of the invention. In particular, peptides from NF-ATc2, NF-ATc3 and NF-ATc5 that are capable of forming intramolecular interactions with an NLS are part of the invention. SP1, SP2 and SP3 sequences are homologous in all NF-ATc family members (see, e.g., Hoey et al., supra).

The NF-AT peptides comprising one or more sequences selected from the group of SRR, SP1, SP2, and SP3 preferably comprise phosphoserines. Each serine of the peptide can be phosphorylated. However, as indicated in the Examples, it is only necessary to have some serines phosphorylated (see FIG. 12) so that the peptide will interact with an NLS. Thus, preferred peptides of the invention are NF-AT peptides having a number of phosphoserines sufficient to allow the peptide to interact with an NLS of NF-AT. A peptide of interest can be phosphorylated in vitro according to the method described in the Examples or according to in vitro phosphorylation assays known in the art.

The invention also provides NF-AT peptides comprising an NLS or one or more of the repeats SRR, SP1, SP2 and SP3 which are homologs, variants, derivatives or peptidomimtics of sequences set forth in SEQ ID NO: 38. Preferred homologs, variants, derivatives, or peptidomimetics are capable of interacting with a portion of an NF-AT polypeptide. Peptides or peptidomimetics can be screened for those that interact with a portion of NF-AT using a binding assay, e.g., the binding assay described in the Examples.

Also within the scope of the invention are NF-AT polypeptides which are constitutively active. Such NF-T polypeptides can be useful since they are not dependent on the presence of calcium to be activated, but rather they can be activated in a regulated manner of choice, as further described below. As shown in the examples, the mutation of certain amino acids in NF-AT result in constitutive nuclear localization and thus constitutive activity. Preferred constitutively active NF-AT polypeptides have at least one amino acid deletion, addition or substitution (generally referred to as "peptide modification") that interferes in the intramolecular interactions in NF-AT. Even more preferred NF-AT polypeptides have a peptide modification located in one or more of the SRR, SP1, SP2 or SP3 sequences of an NF-AT molecule, such that the ability of an NF-AT polypeptide to form an intramolecular association is decreased or inhibited. The peptide modification can be a substitution of one or more of the serines in one or more of the repeats. For example, a constitutively active NF-AT peptide can have a substitution of all the serines located in the SRR region (amino acid 172 to amino acid 194 of SEQ ID NO: 38). Alternatively, a constitutively active peptide can have a substitution of the serines at positions 184, 187 and 188 of SEQ ID NO: 38; a substitution of the serines at positions 172, 175, and 176 of SEQ ID NO: 38; a substitution of the serines at position 178, 179, and 181 of SEQ ID NO: 38; or a substitution of the serines at position 184, 187, and 188 of SEQ ID NO: 38. Constitutively active NF-AT polypeptides can also be obtained by the substitution of one or more serine in the SP1, SP2, and/or SP3 domains. In particular, constitutive NF-AT peptides can comprise a substitution of the four serines in SP1 (corresponding to amino acids 199–219 of SEQ ID NO: 38); substitution of the serines at position 233 and 237 of SP2 (corresponding to amino acids 233–252 of SEQ ID NO: 38); or substitution of serines at 278, 282, 286, and 299 in SP3 (corresponding to amino acids 278–301 of SEQ ID NO: 38). The one or more serines can be substituted with any amino acid so long as the substitution reduces intramolecular interactions, and is preferably an amino acid which cannot be phosphorylated, e.g., an alanine. Mutations that must be made in an NF-AT polypeptide to render it constitutively active can also be identified by screening a library of peptides. For example, one can produce a library of degenerate peptides, e.g., peptides comprising amino acids 172–188 of SEQ ID NO: 38, in which one or more serines or other amino acid is randomly mutated. This library can then be screened for those peptides which fail to interact with an NF-AT NLS, such as by passing the library of degenerate peptides over a column containing an excess of NF-AT NLS peptides. The amino acid sequence of the peptides in the flow-through of the column can then be determined. Alternatively, individual peptides in a library can be tagged, and their identity determined by detecting and identifying the tag.

Constitutively active NF-AT polypeptides can nevertheless be regulated, e.g., by having the gene encoding the constitutively active NF-AT polypeptide under the control of an inducible promoter. Alternatively, the NF-AT polypeptide can be fused to another peptide which can be regulated. For example, a constitutively active NF-AT polypeptide can be fused to a ligand binding domain. Control of the activity of this NF-AT protein can be obtained by further expressing in the cell a fusion protein comprising a ligand binding domain and a cytoplasmic retention domain, such that in the presence of a dimerizer molecule permitting cross-hybridization between the two fusion proteins, the NF-AT fusion protein is retained in the cytoplasm. Translocation to the nucleus is then induced by eliminating the dimerizer.

Alternatively, a constitutively active NF-AT polypeptide can be obtained by fusing the NF-AT polypeptide to an additional NLS, in particular a heterologous NLS, e.g, a viral NLS, such as the SV40 large T antigen NLS. An NF-AT polypeptide can also be fused with two or more NLS. The one or more NLS can be fused to the N-terminus of the NF-AT polypeptides. As shown in Example 10, an NF-AT polypeptide that is covalently linked to one or two copies of a heterologous NLS results in constitutive nuclear localization.

An NLS of NF-AT can also be used to direct a protein, in particular a heterologous protein to the nucleus. As shown in Example 11, the addition of a peptide having the amino acid sequence from amino acid 263–271 of SEQ ID NO: 38 (N-terminal NLS) or a peptide having the amino acid sequence from amino acid 681 to 685 of SEQ ID NO: 38 (C-terminal NLS) to a heterologous polypeptide resulted in constitutive nuclear localization of the polypeptide. Thus, the NLSs from NF-AT are sufficient to direct a polypeptide to the nucleus. Accordingly, also within the scope of the invention are peptides comprising an NLS from NF-AT$_c$ in particular, a peptide comprising the amino acid sequence KRK, or preferably CNKRKYSLN (SEQ ID NO: 53) (amino acids 263–271 of SEQ ID NO: 38), or even more preferably SPCNKRKYSLNGR (SEQ ID NO: 71) (amino acids 261–273 of SEQ ID NO: 38) and/or the amino acid sequence KRKKIR (SEQ ID NO: 66), or preferably GKRKK/R (SEQ ID NO: 67) (amino acids 681–685 of SEQ ID NO: 38), or even more preferably CNGKRKK/RSQ (SEQ ID NO: 72) (amino acids 679–687 of SEQ ID NO: 38).

A dominant negative NF-AT$_c$ or constitutively inactive NF-AT$_c$ can be produced by, e.g., mutating one, or preferably both NLS, such that the NF-AT polypeptide is incapable of translocating from the cytoplasm to the nucleus. An NF-AT polypeptide having one or more mutated NLS can act as a dominant negative mutant since, the polypeptide is still capable of interacting with calcineurin and thus, will compete for calcineurin, thereby prohibiting calcineurin to interact with the endogenous NF-AT molecules and activating them. The N-terminal NLS can be mutated, e.g, by substituting residues 265 to 268 (KRK) of SEQ ID NO: 38.

For example, these residues can be changed to QIL. The C-terminal NLS can be mutated, e.g, by substituting residues 682–685 (KRKK/R (SEQ ID NO: 66)) of SEQ ID NO: 38. For example, these residues can be changed to TRTG (SEQ ID NO: 55). Other mutations are also within the scope of the invention an can be identified, e.g, by performing assays, as described in the examples. Such assays can also be used to screen libraries of mutated NLS sequences.

Particularly preferred variants are structural mimetics of a dominant negative NF-AT$_c$ mutants, such as a polypeptide consisting essentially of amino acids 1–418 of FIG. 1 and substantially lacking amino acids carboxy-terminal to residue 418. Such mimetics of dominant-negative mutant polypeptides can have substantial activity as antagonists or partial agonists of NF-AT activation (and hence T cell activation).

Still another aspect of the present invention relates to peptide and peptidomimetic inhibitors, derived from the NLS sequence, which inhibit glucan synthase kinases, e.g., GSK-3.

Native NF-AT$_c$ proteins, fragments thereof, or analogs thereof can be used as reagents in DNA binding assays and/or in vitro transcription assays for identifying agents that interfere with NF-AT function, said agents are thereby identified as candidate drugs which may be used, for example, to block T cell activation or treat T cell lymphocytic leukemias. Typically, in vitro DNA binding assays that measure binding of NF-AT to DNA employ double-stranded DNA that contains an array of one or more NF-AT recognition sites (as defined by specific footprinting of native NF-AT protein). The DNA is typically linked to a solid substrate by any of various means known to those of skill in the art, such linkage may be noncovalent (e.g., binding to a highly charged surface such as Nylon 66) or may be by covalent bonding (e.g., typically by chemical linkage involving a nitrogen position in a nucleotide base, such as diazotization). NF-AT$_c$ polypeptides are typically labeled by incorporation of a radiolabeled amino acid. The labeled NF-AT$_c$ polypeptide, usually reconstituted with an NF-AT nuclear component (e.g., AP-1 activity) to form an NF-AT complex, is contacted with the immobilized DNA under aqueous conditions that permit specific binding in control binding reactions with a binding affinity of about $1 \times 10^6$ M$^{-1}$ or greater (e.g., 10–250 mM NaCl or KCl and 5–100 mM Tris HCl pH 5–9, usually pH 6-8), generally including Zn$^{+2}$ and/or Mn$^{+2}$ and/or Mg$^{+2}$ in the nanomolar to micromolar range (1 nM to 999 $\mu$M). Specificity of binding is typically established by adding unlabeled competitor at various concentrations selected at the discretion of the practitioner. Examples of unlabeled protein competitors include, but are not limited to, the following: unlabeled NF-AT$_c$ polypeptide, bovine serum albumin, and nuclear protein extracts. Binding reactions wherein one or more agents are added are performed in parallel with a control binding reaction that does not include an agent. Agents which inhibit the specific binding of NF-AT$_c$ polypeptides to DNA, as compared to a control reaction, are identified as candidate immunomodulatory drugs. Also, agents which prevent transcriptional modulation by NF-AT in vitro are thereby identified as candidate immunomodulatory drugs.

As set forth above, in addition to NF-AT$_c$ polypeptides consisting only of naturally-occuring amino acids, NF-AT$_c$ peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as human NF-AT$_c$, but have one or more peptide linkages optionally replaced by a linkage selected from the group consisting of —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 (—CH$_2$NH—, CH$_2$CH$_2$—); Spatola, A. F. et al., *Life Sci* (1986) 38:1243–1249 (—CH$_2$S); Hann, M. M., *J Chem Soc Perkin Trans I* (1982) 307–314 (—CH—CH—, cis and trans); Almquist, R. G. et al., *J Med Chem* (1980) 23: 1392–1398 (—COCH$_2$—); Jennings-White, C. et al., *Tetrahedron Lett* (1982) 23:2533 (—COCH$_2$—); Szelke, M. et al., European Appln. EP 45665 (1982) CA: 97:39405 (1982) (—CH(OH)CH$_2$—); Holladay, M. W. et al., *Tetrahedron Lett* (1983) 24:4401–4404 (—C(OH)CH$_2$—); and Hruby, V. J., *Life Sci* (1982) 31:189–199 (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labelling) of peptidomimetics should not substantially interfere with the desired biological or pharmacological activity of the peptidomimetic. Peptidomimetics of NF-AT$_c$ may be used as competitive or noncompetitive agonists or antagonists of NF-AT$_c$ function. For example, a NF-AT$_c$ peptidomimetic administered to a stimulated T cell containing NF-AT$_c$ and may compete with the naturally-occurring NF-AT$_c$ and reduce NF-AT activity. Alternatively, an NF-AT$_c$ peptidomimetic administerd to a T cell lacking NF-AT$_c$ may induce T cell activation or the like.

Systematic substitution of one or more amino acids of a consensus sequence with a D-amino acid of the same type (e.g., D-lysine in place of L-lysine) may be used to generate more stable peptides. In addition, constrained peptides (including cyclized peptides) comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide.

The amino acid sequences of NF-AT$_c$ polypeptides identified herein will enable those of skill in the art to produce polypeptides corresponding to NF-AT$_c$ peptide sequences and sequence variants thereof Such polypeptides may be produced in prokaryotic or eukaryotic host cells by expression of polynucleotides encoding a NF-AT$_c$ peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology, Volume 152, Guide to Molecular Cloning Techniques* (1987), Academic Press, Inc., San Diego, Calif.; Merrifield, J. (1969) *J. Am. Chem. Soc.* 91: 501; Chaiken I. M. (1981) *CRC Crit. Rev. Biochem.* 11: 255; Kaiser et al. (1989) *Science* 243: 187; Merrifield, B. (1986) *Science* 232: 342; Kent, S. B. H. (1988) *Ann. Rev. Biochem.* 57: 957; and Offord, R. E. (1980) *Semisynthetic Proteins*, Wiley Publishing, which are incorporated herein by reference).

7. Production and Applications of α-NF-AT$_c$ Antibodies

Native NF-AT$_c$ proteins, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see Antibodies: *A Laboratory Manual*, (1988) E. Harlow and D. Lane, Cold Spring Harbor Laboratory, Cold Spring Harbor, N.Y., which is incorporated herein by reference.

For example but not for limitation, a recombinantly produced fragment of human NF-AT$_c$ can be injected into a rat along with an adjuvant following immunization protocols known to those of skill in the art so as to generate an immune response. Typically, approximately at least 1–50 μg of a NF-AT$_c$ fragment or analog is used for the initial immunization, depending upon the length of the polypeptide. Alternatively or in combination with a recombinantly produced NF-AT$_c$ polypeptide, a chemically synthesized peptide having a NF-AT$_c$ sequence (e.g., peptides exemplified in Table II, infra) may be used as an immunogen to raise antibodies which bind a NF-AT$_c$ protein, such as the native human NF-AT$_c$ polypeptide having the sequence shown essentially in FIG. 1 or the native human NF-AT$_c$ polypeptide isoform. Immunoglobulins which bind the recombinant fragment with a binding affinity of at least $1\times10^7$ M$^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells The bank of hybridomas can be screened for clones that secrete immunoglobulins which bind the recombinantly produced NF-AT$_c$ polypeptide (or chemically synthesized NF-AT$_c$ polypeptide) with an affinity of at least $1\times10^6$ M$^{-1}$. Animals other than mice and rats may be used to raise antibodies; for example, goats, rabbits, sheep, and chickens may also be employed to raise antibodies reactive with a NF-AT$_c$ protein. Transgenic mice having the capacity to produce substantially human antibodies also may be immunized and used for a source of α-NF-AT$_c$ antiserum and/or for making monoclonal-secreting hybridomas.

Bacteriophage antibody display libraries may also be screened for binding to a NF-AT$_c$ polypeptide, such as a full-length human NF-AT$_c$ protein, a NF-AT$_c$ fragment (e.g., a peptide having a sequence shown in Table II, infra), or a fusion protein comprising a NF-AT$_c$ polypeptide sequence of at least 14 contiguous amino acids as shown in FIG. 1 or a polypeptide sequence of Table II (infra). Combinatorial libraries of antibodies have been generated in bacteriophage lambda expression systems which may be screened as bacteriophage plaques or as colonies of lysogens (Huse et al. (1989) Science 246: 1275; Caton and Koprowski (1990) Proc. Natl. Acad. Sci. (U.S.A.) 87: 6450; Mullinax et al (1990) Proc. Natl. Acad. Sci. (U.S.A.) 87: 8095; Persson et al. (1991) Proc. Natl. Acad. Sci. (U.S.A.) 88: 2432). Various embodiments of bacteriophage antibody display libraries and lambda phage expression libraries have been described (Kang et al. (1991) Proc. Natl. Acad. Sci. (U.S.A.) 88: 4363; Clackson et al. (1991) Nature 352: 624; McCafferty et al. (1990) Nature 348: 552; Burton et al. (1991) Proc. Natl. Acad. Sci. (U.S.A.) 88: 10134; Hoogenboom et al. (1991) Nucleic Acids Res 19: 4133; Chang et al. (1991) J. Immunol. 147: 3610; Breitling et al. (1991) Gene 104: 147; Marks et al. (1991) J. Mol. Biol. 222: 581; Barbas et al. (1992) Proc. Natl. Acad. Sci. (U.S.A.) 89: 4457; Hawkins and Winter (1992) J. Immunol. 22: 867; Marks et al. (1992) Biotechnology 10: 779; Marks et al. (1992) J. Biol. Chem. 267: 16007; Lowman et al (1991) Biochemistry 30: 10832; Lerner et al. (1992) Science 258: 1313, incorporated herein by reference). Typically, a bacteriophage antibody display library is screened with a NF-AT$_c$ polypeptide that is immobilized (e.g., by covalent linkage to a chromatography resin to enrich for reactive phage by affinity chromatography) and/or labeled (e.g., to screen plaque or colony lifts).

NF-AT$_c$ polypeptides which are useful as immunogens, for diagnostic detection of α-NF-AT$_c$ antibodies in a sample, for diagnosic detection and quantitation of NF-AT$_c$ protein in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other proteins of humans, mice, or other contaminants. Preferred immunogens comprise at least one NF-AT$_c$ polypeptide sequence shown in Table II, either as a discrete peptide or as part of a fusion polypeptide (e.g., with a β-galactosidase or glutathione S-transferase sequence). NF-AT$_c$ immunogens comprise at least one, typically several of such immunogenic epitopes.

For some applications of these antibodies, such as identifying immunocrossreactive proteins, the desired antiserum or monoclonal antibody(ies) is/are not monospecific. In these instances, it may be preferable to use a synthetic or recombinant fragment of NF-AT$_c$ as an antigen rather than using the entire native protein. More specifically, where the object is to identify immunocrossreactive polypeptides that comprise a particular structural moiety, such as a DNA-binding domain, it is preferable to use as an antigen a fragment corresponding to part or all of a commensurate structural domain in the NF-AT$_c$ protein. Production of recombinant or synthetic fragments having such defined amino- and carboxy-termini is provided by the NF-AT$_c$ sequences shown in FIG. 1.

If an antiserum is raised to a NF-AT$_c$ fusion polypeptide, such as a fusion protein comprising a NF-AT$_c$ immunogenic epitope fused to β-galactosidase or glutathione S-transferase, the antiserum is preferably preadsorbed with the non-NF-AT$_c$ fusion partner (e.g, β-galactosidase or glutathione S-transferase) to deplete the antiserum of antibodies that react (i.e., specifically bind to) the non-NF-AT$_c$ portion of the fusion protein that serves as the immunogen. Monoclonal or polyclonal antibodies which bind to the human and/or murine NF-AT$_c$ protein can be used to detect the presence of human or murine NF-AT$_c$ polypeptides in a sample, such as a Western blot of denatured protein (e.g., a nitrocellulose blot of an SDS-PAGE) obtained from a lymphocyte sample of a patient. Preferably quantitative detection is performed, such as by denistometric scanning and signal integration of a Western blot. The monoclonal or polyclonal antibodies will bind to the denatured NF-AT$_c$ epitopes and may be identified visually or by other optical means with a labeled second antibody or labeled Staphylococcus aureus protein A by methods known in the art.

Frequently, denatured NF-AT$_c$ will be used as the target antigen so that more epitopes may be available for binding.

TABLE II

Selected Human NF-AT Antigen Peptides

| | |
|---|---|
| -NAIFLTVSREHERVGC-; | (SEQ ID NO: 25) |
| -LHGYLENEPLMLQLFIGT-; | (SEQ ID NO: 26) |
| -PSTSPRASVTEESWLG-; | (SEQ ID NO: 27) |
| -GPAPRAGGTMKSAEEEHYG-; | (SEQ ID NO: 28) |
| -ASAGGHPIVQ-; | (SEQ ID NO: 29) |
| -NTRVRLVFRV-; | (SEQ ID NO: 30) |
| -AKTDRDLCKPNSLVVEIPPFRN-; | (SEQ ID NO: 31) |
| -EVQPKSHHIRAHYETEGSR-; | (SEQ ID NO: 32) |
| -SPRVSVTDDSWLGNT-; | (SEQ ID NO: 33) |
| -SHHRAHYETEGSRGAV-; | (SEQ ID NO: 34) |
| -LRNSDIELRKGETDIGR-; | (SEQ ID NO: 35) |
| and | |
| -TLSLQVASNPIEC-. | (SEQ ID NO: 36) |

Such NF-AT$_c$ sequences as shown in Tables II may be used as an immunogenic peptide directly (e.g., to screen bacteriophage antibody display libraries or to immunize a rabbit), or may be conjugated to a carrier macromolecule (e.g., BSA) or may compose part of a fusion protein to be used as an immunogen. A preferred NF-AT$_c$ polypeptide comprises the following amino acids sequences:

-NAIFLTVSREHERVGC-(SEQ ID NO: 25);
-PSTSPRASVTEESWLG-(SEQ ID NO: 27);
-SPRVSVTDDSWLGNT-(SEQ ID NO: 33); and
-SHHRAHYETEGSRGAV-(SEQ ID NO: 34);

and may comprise other intervening and/or terminal sequences; generally such polypeptides are less than 1000 amino acids in length, more usually less than about 500 amino acids in length; often spacer peptide sequences or terminal peptide sequences, if present, correspond to naturally occurring polypeptide sequences, generally mammalian polypeptide sequences. One application of the preferred NF-AT$_c$ polypeptide just recited is as a commercial immunogen to raise α-NF-AT$_c$ antibodies in a suitable animal and/or as a commercial immunodiagnostic reagent for quantitative ELISA (e.g., competitive ELISA) or competitive RIA in conjunction with the anti-NF-AT$_c$ antibodies provided by the invention, such as for calibration of standardization of such immunoassays for staging or diagnosis of NF-AT$_c$-expressing lymphocytic leukemias in humans or cell typing or identification of T cells (such as activated T cells and/or activatable T cells). The preferred NF-AT$_c$ polypeptide just recited will find many other uses in addition to serving as an immunogen or immunological reagent. One or more of the above-listed sequences may be incorporated into a fusion protein with a fusion partner such as human serum albumin, GST, etc. For such fusion proteins in excess of 1000 amino acids, deletions in the fusion partner (albumin) moiety may be made to bring the size to about 1000 amino acids or less, if desired.

In some embodiments, it will be desirable to employ a polyvalent NF-AT$_c$ antigen, comprising at least two NF-AT$_c$ immunogenic epitopes in covalent linkage, usually in peptide linkage. Such polyvalent NF-AT$_c$ antigens typically comprise multiple NF-AT$_c$ antigenic peptides from the same species (e.g., human or mouse), but may comprise a mix of antigenic peptides from NF-AT$_c$ proteins of different species (i.e., an interspecies NF-AT$_c$ polyvalent antigen). Frequently, the spatial order of the antigenic peptide sequences in the primary amino acid sequence of a polyvalent antigen occurs in the same orientation as in the naturally occurring NF-AT$_c$ protein (i.e., a first antigenic peptide sequence that is amino-terminal to a second antigenic peptide sequence in a naturally occurring NF-AT$_c$r protein will be amino-terminal to said second antigenic peptide sequence in a polyvalent antigen. Frequently, spacer peptide sequences will be used to link antigenic peptide sequences in a polyvalent antigen, such spacer peptide sequences may be predetermined, random, or psuedorandom sequences. Spacer peptide sequences may correspond to sequences known to be non-immunogenic to the animal which is to be immunized with the polyvalent antigen, such as a sequence to which the animal has been tolerized. Although many examples of such polyvalent antigens may be given, the following embodiment is provided for illustration and not limitation:
-NAIFLTVSREHERVGC-(aa1) (SEQ ID NO: 25)-AKTDRDLCKPNSLVVEIPPFRN-(aa2) (SEQ ID NO: 31)-GILKLRNSDIELRKGETD-(SEQ ID NO: 37)
  where (aa1) and (aa2) are peptide spacers of at least one amino acid and less than 1000 amino acids, aa1 is a peptide sequence selected independently from the aa2 peptide sequence; the length of aa1 (which may be composed of multiple different amino acids) is independent of the length of aa2 (which may be composed of multiple different amino acids).

Immunogenic NF-AT$_c$ peptides may be used to immunize an animal to raise anti-NF-AT$_c$ antibodies and/or as a source of spleen cells for making a hybridoma library from which to select hybridoma clones which secrete a monoclonal antibody which binds to a NF-AT$_c$ protein with an affinity of $1 \times 10^7$ M$^{-1}$ or greater, preferably at least $1 \times 10^8$ M$^{-1}$ to $1 \times 10^9$ M$^{-1}$. Such immunogenic NF-AT$_c$ peptides can also be used to screen bacteriophage antibody display libraries directly.

One use of such antibodies is to screen cDNA expression libraries, preferably containing cDNA derived from human or murine mRNA from various tissues, for identifying clones containing cDNA inserts which encode structurally-related, immunocrossreactive proteins, that are candidate novel transcription factors or chromatin proteins. Such screening of cDNA expression libraries is well known in the art, and is further described in Young et al., *Proc. Natl. Acad. Sci. U.S.A.* 80:1194–1198 (1983), which is incorporated herein by reference] as well as other published sources. Another use of such antibodies is to identify and/or purify immunocrossreactive proteins that are structurally or evolutionarily related to the native NF-AT$_c$ protein or to the corresponding NF-AT$_c$ fragment (e.g., functional domain; DNA-binding domain) used to generate the antibody. It is believed that such antibodies will find commercial use as such reagents for research applications, just as other antibodies (and biological reagents—such as restriction enzymes and polymerases) are sold commercially.

Various other uses of such antibodies are to diagnose and/or stage leukemias or other immunological disease states, and for therapeutic application (e.g., as cationized antibodies or by targeted liposomal delivery) to treat neoplasia, hyperimmune function, graft rejection, and the like.

An example of an NF-ATc polypeptide is a polypeptide having the sequence:
MPSTSFPVPSKFPLGPAAAVFGRGETLG-PAPRAGGTMKSAEEEHYGYASSNVSPALPLPTAHS TLPAPCHNLQTSTPGIIPPADHPSGYGA-ALDGCPAGYFLSSGHTRPDGAPALESPRIEITSCL GLYHNNNQFFHDVEVEDVLPSSKRSP-STATLSLPSLEAYRDPSCLSPASSLSSRSCNSEASSY ESNYSYPYASPQTSPWQSPCVSPKTTD-PEEGFPRGLGACTLLGSPQHSPSTSPRASVTEESWL GARSSRPASPCNKRKYSLNGRQP-PYSPHHSPTPSPHGSPRVSVT-DDSWLGNTTQYTSSAIVAA INALTTDSSLD-LGDGVPVKSRKTTLEQPPSVALKVEPVGEDLGS PPPPADFAPEDYSSFQHIR KGGFCDQYLAVPQH-PYQWAKPKPLSPTSYMSPTLPALDWQLP-SHSGPYELRIEVQPKSHHRAH YETEGSR-GAVKASAGGHPIVQLHGYLENEPLMLQLFIGTA DDRLLRPHAFYQVH RITGKTVST TSHEAILSNT-KVLEIPLLPENSMRAVIDCACILKLRNS-DIELRKGETDIGRKNTRVRLVFRVH VPQPS-GRTLSLQVASNPIECSQRSAQELPLVEKQSTDSY PVVGGKKMVLSGH NFLQDSKVIFV EKAPDGHH-VWEMEAKTDRDLC KPNSLVVEIPPFRN-QRITSPVHVSFYVCNGKRKRSQYQRFTY LPANG-NAIFLTVSREHERVGCFF (SEQ ID NO: 38).

Other preferred antigens for preparing antibodies include phosphorylated NF-AT polypeptides or domains thereof. For example, the invention provides antibodies binding specifically to phosphorylated NF-ATc polypeptides, and not to those that are not phosphorylated.

The NF-ATc polypeptide can be phosphorylated on a serine, such as a serine located in SRR, SP1, SP2, SP3 or which is located between these repetitive sequences. Such antibodies can be used to hide or shield these phosphorylated domains from NLSs thereby favoring NF-ATc localization in the nucleus of a cell. Alternatively, such antibodies can be used to specifically detect the phosphorylated form, e.g., in diagnostics.

8. Identification and Isolation of Proteins That Bind NF-AT$_c$

Proteins that bind to NF-AT$_c$ and/or a NFAT-DNA complex are potentially important transcriptional regulatory proteins. Such proteins may be targets for novel immunomodulatory agents. These proteins are referred to herein as accessory proteins. Accessory proteins may be isolated by various methods known in the art.

One preferred method of isolating accessory proteins is by contacting a NF-AT$_c$ polypeptide to an antibody that binds the NF-AT$_c$ polypeptide, and isolating resultant immune complexes. These immune complexes may contain accessory proteins bound to the NF-AT$_c$ polypeptide. The accessory proteins may be identified and isolated by denaturing the immune complexes with a denaturing agent and, preferably, a reducing agent. The denatured, and preferably reduced, proteins can be electrophoresed on a polyacrylamide gel. Putative accessory proteins can be identified on the polyacrylamide gel by one or more of various well known methods (e.g., Coomassie staining, Western blotting, silver staining, etc.), and isolated by resection of a portion of the polyacrylamide gel containing the relevant identified polypeptide and elution of the polypeptide from the gel portion.

A putative accessory protein may be identified as an accessory protein by demonstration that the protein binds to NF-AT$_c$ and/or a NFAT-DNA complex. Such binding may be shown in vitro by various means, including, but not limited to, binding assays employing a putative accessory protein that has been renatured subsequent to isolation by a polyacrylamide gel electrophoresis method. Alternatively, binding assays employing recombinant or chemically synthesized putative accessory protein may be used. For example, a putative accessory protein may be isolated and all or part of its amino acid sequence determined by chemical sequencing, such as Edman degradation. The amino acid sequence information may be used to chemically synthesize the putative accessory protein. The amino acid sequence may also be used to produce a recombinant putative accessory protein by: (1) isolating a cDNA clone encoding the putative accessory protein by screening a cDNA library with degenerate oligonucleotide probes according to the amino acid sequence data, (2) expressing the cDNA in a host cell, and (3) isolating the putative accessory protein. Alternatively, a polynucleotide encoding a NF-AT$_c$ polypeptide may be constructed by oligonucleotide synthesis, placed in an expression vector, and expressed in a host cell.

Putative accessory proteins that bind NF-AT$_c$ and/or NFAT-DNA complex in vitro are identified as accessory proteins. Accessory proteins may also be identified by crosslinking in vivo with bifunctional crosslinking reagents (e.g., dimethylsuberimidate, glutaraldehyde, etc.) and subsequent isolation of crosslinked products that include a NF-ATc polypeptide. For a general discussion of crosslinking, see Kunkel et al. (1981) *Mol. Cell. Biochem.* 34: 3, which is incorporated herein by reference. Preferably, the bifunctional crosslinking reagent will produce crosslinks which may be reversed under specific conditions after isolation of the crosslinked complex so as to facilitate isolation of the accessory protein from the NF-AT$_c$ polypeptide. Isolation of crosslinked complexes that include a NF-AT$_c$ polypeptide is preferably accomplished by binding an antibody that binds a NF-ATc polypeptide with an affinity of at least $1 \times 10^7$ M$^{-1}$ to a population of crosslinked complexes and recovering only those complexes that bind to the antibody with an affinity of at least $1 \times 10^7$ M$^{-1}$. Polypeptides that are crosslinked to a NF-AT$_c$ polypeptide are identified as accessory proteins.

Screening assays can be developed for identifying candidate immunomodulatory agents as being agents which inhibit binding of NF-AT$_c$ to an accessory protein (e.g. AP-1) under suitable binding conditions (see infra).

10. Yeast Two-Hybrid Screening Assays

Yeast two-hybrid systems may be used to screen a mammalian (typically human) cDNA expression library, wherein cDNA is fused to a GAL4 DNA binding domain or activator domain, and a NF-AT$_c$ polypeptide sequence is fused to a GAL4 activator domain or DNA binding domain, respectively. Such a yeast two-hybrid system can screen for cDNAs encoding proteins which bind to NF-AT$_c$ sequences.

For example, a cDNA library can be produced from mRNA from a human mature T cell line or other suitable cell type. Such a cDNA library cloned in a yeast two-hybrid expression system (Chien et al. (1991) *Proc. Natl. Acad. Sci. (U.S.A.)* 88: 9578 or Cell 72: 233) can be used to identify cDNAs which encode proteins that interact with NF-AT$_c$ and thereby produce expression of the GAL4-dependent reporter gene. Polypeptides which interact with NF-AT$_c$ can also be identified by immunoprecipitation of NF-AT$_c$ with antibody and identification of co-precipitating species. Further, polypeptides that bind NF-AT$_c$ can be identified by screening a peptide library (e.g., a bacteriophage peptide display library, a spatially defined VLSIPS peptide array, and the like) with a NF-AT$_c$ polypeptide.

10. Exemplary Methods of the Invention

The invention provides methods for modulating the activity of NF-AT in a cell. In one embodiment, the activity of NF-AT is modulated by modulating its interaction with another molecule, such as another protein or a nucleic acid. In particular, the activity of NF-AT can be modulated by modulating the interaction between NF-ATc and AP-1 or other basic domain/leucine zipper proteins. In another embodiment, the interaction of NF-ATc with DNA, i.e., the NF-ATc binding site, can be modulated.

In a preferred embodiment, the method modulates the translocation of NF-AT through the nuclear membrane. For example, certain methods of the invention stimulate or inhibit translocation of NF-AT proteins from the cytoplasm to the nucleus. Other methods of the invention stimulate or inhibit translocation of NF-AT molecules from the nucleus to the cytoplasm. For example, the translocation of NF-AT from the cytoplasm into the nucleus of a cell can be stimulated or induced by introducing into the cell a compound which inhibits the interaction of at least one NLS with another part of the NF-AT molecule, thereby unshielding at least one NF-AT NLS, allowing the NF-AT molecule to translocate into the nucleus. A compound which inhibit the interaction between an NLS and another portion of the NF-AT protein can be a small molecule, a peptide, peptidomimetic, a nucleic acid or derivatives thereof A preferred compound is peptide or peptidomimetic comprising an NF-AT NLS, or homolog thereof, which is capable of forming an intramolecular association with another portion of the NF-AT molecule, such as with one or more of the repeats, e.g, SRR, SP1, SP2, or SP3. Such compounds are further described herein. Another preferred compound is a nucleic acid which encodes such a peptide. Accordingly, the nucleic acid is introduced into a cell expressing NF-AT and expressed in the cell. In another embodiment, the compound is a small molecule, which can be isolated as described herein by screening libraries of small molecules. The compound is preferably small and able to cross the cytoplasmic membrane.

In another embodiment, the invention provides a method for inhibiting the translocation of NF-AT from the cytoplasmic to the nucleus, thereby inhibiting NF-AT dependent biologic activities. This can be achieved, e.g., by stabilizing the intramolecular association of at least one NLS with another portion of an NF-AT molecule. Methods may include introducing into a cell a compound which stabilizes the interaction of an NLS with at least one portion of NF-AT selected from the group consisting of SRR, SP1, SP2 and SP3. The compound is preferably a small molecule, which can be obtained as described herein.

In yet another embodiment, the invention provides a method for stimulating the translocation of NF-AT from the nucleus to the cytoplasm of a cell, thereby blocking activation of NF-AT dependent biological activities. This can be achieved, e.g., by shielding one or more of the NLSs in NF-AT molecules. In an illustrative embodiment, an NLS sequence in an NF-AT molecule in a cell is shielded by introducing into the cell a compound which interacts with the NLS sequence. A preferred compound is a peptide or peptidomimetic, e.g., a peptide comprising an amino acid sequence selected from the group consisting of the SRR, SP1, SP2, or SP3 sequence of NF-AT. In a preferred embodiment, two compounds are introduced into a cell, i.e., a first compound which interacts with the NLS KRK (amino acids 265–267 of SEQ ID NO: 38) and a second compound which interacts with the NLS KRKK/R (SEQ ID NO: 66) (amino acids 682–685 of SEQ ID NO: 38). For example, a peptide comprising the amino acid sequence of SRR and a peptide comprising the amino acid sequence of at least one of SP1, SP2 and SP3 can be administered to a cell.

Furthermore, also within the scope of the invention are methods for inhibiting the translocation of NF-AT molecules from the nucleus to the cytoplasm of a cell, thereby maintaining or prolonging NF-AT dependent biological activities. Such methods can comprise introducing into the nucleus of a cell comprising NF-AT molecules in the nucleus a compound which prevents one or more of the NLSs to form an intramolecular association. This can be achieved, e.g., by introducing into the cell a compound which interacts with a portion of NF-AT which is capable of interacting with an NLS. For example, the compound can be an NLS peptide or derivative thereof, which is capable of binding to a portion of an NF-AT molecule, e.g., an SRR, SP1, SP2 and/or SP3 repeat. Based at least on the sequence homologies between the NF-ATc family members, a single peptide could interact with at least two NF-ATc family members. Other compounds that can be used for this purpose include nucleic acids encoding such peptides and small molecules.

Other methods for modulating translocation of an NF-ATc polypeptide comprise modulating phosphorylation of NF-ATc, such as the phosphorylation of serines located in the region from about amino acid 1 to about amino acid 418 of SEQ ID NO: 38, or even more preferably from about amino acid 170 to about amino acid 301 of SEQ ID NO: 38. Even more preferably, the method comprises phosphorylation of serines located in SRR, SP1, SP2, and/or SP3, and/or in regions located between these repeats.

Phosphorylation of NF-ATc polypeptides can be modulated by a variety of methods. In one embodiment, phosphorylation is modulated by modulating the activity of a kinase which phosphorylates NF-ATc, such as PKA, GSK-3α and GSK-3β. Another kinase whose activity can be phosphorylated include JNK (jun kinase), e.g., JNK-1 or JNK-2. The activity of a kinase can be modulated by modulating the protein level of the kinase. For example, increasing the activity of a kinase can be accomplished by increasing the endogenous protein level of the kinase, such as by increasing transcription of the kinase. Alternatively, the activity of a kinase can be increased by introducing a kinase into a cell, such as by introducing a nucleic acid encoding the kinase. In fact, as shown herein, overexpression of GSK-3 in T cells inhibited translocation of NF-AT to the nucleus, and increased nuclear export of NT-ATc. Stimulation of translocation of NF-AT from the cytoplasm to the nucleus can be achieved by inhibiting the activity of a kinase which phosphorylates NF-ATc, such as by inhibiting transcription or translation of the kinase, e.g., by using antisense technology. The activity of the kinase can also be inhibited by introducing into the cell an agent which inhibits its activity, such as an NF-AT peptide, capable of binding to the kinase.

In another embodiment, phosphorylation is modulated by modulating the activity of a phosphatase, such as calcineurin. This can be achieved by modulating its phosphorylation capacity, by, e.g., contacting it with an NF-AT peptide with which calcineurin is capable of interacting. Alternatively, the level of calcineurin in a cell can be modulated, such as by modulating its expression or by introducing exogenous calcineurin in the cell or by introducing antisense nucleic acids inhibiting calcineurin mRNA translation.

In still another embodiment, the present invention provides compounds which inhibit either the phosphorylation of an NF-AT protein by a glucan synthase kinase like GSK-3, or dephosphorylation of NF-AT by a phosphatase such as calcineurin. In this regard, the application provides drug screening assays based on monitoring the rate of phosphorylation of NF-AT, e.g., a particularly significant residues, by GSK-3 in the presence of absence of a test compound. Likewise, the application describes drug screening assays based on monitoring the rate of

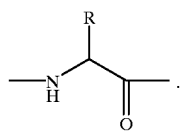

dephosphorylation of NF-AT, e.g., a particularly significant residues, by calcineurin in the presence of absence of a test compound.

On salient feature to our discovery that GSK-3 is a specific phosphatase for NF-AT proteins, and the elucidation of particular residues (e.g., the NLS sites) as substrates for GSK-3, the present invention also provides peptide and peptidimimetic inhibitors of GSK-3. Such inhibitors can correspond to 4 or more residues of NF-AT$_c$ and can be in the range of 4–25, more preferably 4–15 and even more preferably 4–10. The inhibitors preferably have Ki's for inhibition of GSK-3 phosphorylation of an NF-AT of 1 $\mu$M or less, more preferably of 100 mM or less, and even more preferably of 1 nM or less.

Preferably, the peptide or peptidimimetic inhibitor of GSK-3 includes a phosphoserine residue, or, even more preferably, an analog thereof The phosphoserine moiety can be represented by the general formula, where R is selected from a group consisting of wherein i is zero or an integer in the range of 1 to 6; X is absent or represents O, S, or N; D, represents O or S; $D_2$ represents $N_3$, $SH_2$, $NH_2$, or $NO_2$; and $R_{15}$ and $R_{16}$ each independently represent hydrogen, a lower alkyl, or a pharmaceutically acceptable salt, or $R1_5$ and $R_{16}$ taken together with the O-P-O, O-B-O, O-V-O or O-As-O atoms to which they are attached complete a heterocyclic ring having from 5 to 8 atoms in the ring structure. In a preferred embodiment, the phosphoserine is a non-hydrolyzable phosphoserine analog.

For illustrative purposes, peptide analogs of the present invention can be generated using benzodiazepines, substituted gama lactam rings (Garvey et al. in *Peplides: Chemistry and Biology*, G. R. Marshall ed., ESCOM Publisher: Leiden, Netherlands, 1988, p123), C-7 mimics (Huffman et al. in *Peptides: Chemistry and Biology*, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett*

26:647; and Sato et al. (1986) *J Chem Soc Perkin Trans* 1:1231), β-aminoalcohols (Gordon et al. (1985) *Biochem Biophys Res Commun*126:419; and Dann et al. (1986) *Biochem Biophys Res Commun* 134:71), diaminoketones (Natarajan et al. (1984) *Biochem Biophys Res Commun* 124:141), and methyleneamino-modifed (Roark et al. in *Peptides: Chemistry and Biology*, G. R. Marshall ed., ESCOM Publisher: Leiden, Netherlands, 1988, p134). Also, see generally, Session III: Analytic and synthetic methods, in in *Peptides: Chemistry and Biology*, G. R. Marshall ed., ESCOM Publisher: Leiden, Netherlands, 1988).

In other exemplary embodiments, the peptidomimetic can be derived as a retro-inverso

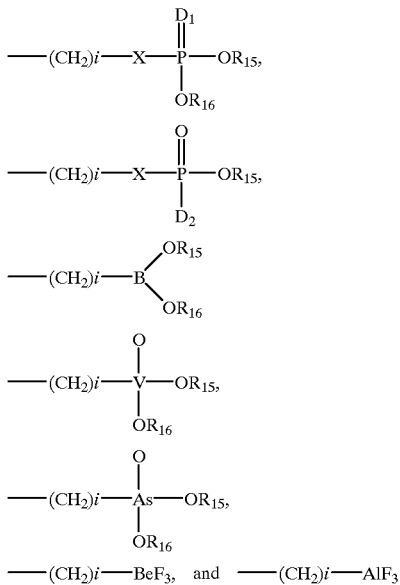

analog of a peptide sequence, such as that described by the Sisto et al. U.S. Pat. No. 4,522,752, as a retro-enatio analog of the peptide, as a trans-olefin derivatives such as can be synthesized according to the method of Y. K. Shue et al. (1987) *Tetrahedron Letters* 28:3225, or as a phosphonate derivative, such as can be adapted from such synthesis schemes as, Loots et al. in *Peptides: Chemistry and Biology*, (Escom Science Publishers, Leiden, 1988, p. 118); Petrillo et al. in *Peptides: Structure and Function* (Proceedings of the 9th American Peptide Symposium, Pierce Chemical Co. Rockland, Ill., 1985).

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The phrase "therapeutically-effective amount" as used herein means that amount of a compound, material, or composition comprising a peptide or peptidomimetic of the present invention which is effective for producing some desired therapeutic effect by inhibiting an NF-AT dependent signaling pathway in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject peptidomimetic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The invention also provides methods for providing activation of NF-AT dependent biological activities by introducing into a cell a constitutively active NF-AT, e.g., an NF-AT polypeptide in which the NLS cannot form intramolecular interactions with other parts of the protein, thereby resulting in an NF-AT protein which constitutively translocates to the nucleus. Such NF-AT proteins can, e.g., have substitutions of serines in the SRR, SP1, SP2, and/or SP3 regions of the NF-AT protein, such that at least one NLS of the NF-AT is "unshielded". Thus, the activity of a constitutively active NF-AT protein can be modulated by modulating the expression of a gene encoding the protein. For example, the gene encoding the constitutively active NF-AT can be placed under the control, e.g., transcriptional control, of an inducible regulatory element.

Another constitutively active NF-AT polypeptide that can be used according to the methods of the invention comprises one or more additional NLS. These can be NF-AT NLS or heterologous NLSs, such as the SV40 large T antigen NLS.

Alternatively, NF-AT dependent biological activities can be modulated as follows. An NF-AT polypeptide that is mutated so that it is constitutively active, is fused to a ligand binding domain and expressed in a cell which further expresses a cytoplasmic retention domain fused to a ligand binding domain, such that in the presence of a dimerizer, the two fusion proteins are cross-linked and the NF-AT protein is retained in the cytoplasm. Translocation of the NF-AT protein into the nucleus can be induced by the absence of, or removal of, the dimerizer.

In yet another embodiment, the invention provides a method for regulating the expression of NF-AT by regulating the expression of a dominant negative mutant of NF-AT. In one embodiment, a dominant negative mutant is an NF-AT protein that is incapable of translocating to the nucleus, e.g., an NF-AT polypeptide in which at least one, but preferably two NLSs are inactivated, e.g, by mutation. Such mutant NF-AT polypeptides are still capable of interacting with calcineurin, and will thereby compete away calcineurin from endogenous NF-AT molecules.

In yet another embodiment, the invention provides a method for regulating translocation of a heterologous polypeptide across the nuclear membrane that is not dependent on intracellular calcium. Accordingly, a heterologous polypeptide is fused an NLS of NF-AT, e.g., the C-terminal NLS, and to an NF-AT portion selected from the group consisting of SRR, SP1, SP2, and SP3. Preferably, the NF-AT portion is an SRR. The cellular localization of a heterologous polypeptide fused to these portions of NF-AT in a cell will depend on the presence of calcium. Thus, in normal conditions, it is expected that the protein will be located in the cytoplasm of the cell and that, in the presence of a calcium ionophore, the polypeptide will translocate to the nucleus. Alternatively, a heterologous polypeptide can be fused to an NLS only and its intracellular location modulated by addition to the cell of a compound, e.g, a peptide that interacts with the NLS.

Moreover, GSK-3 has been shown to be involved in dorsal-ventral pattern formation in Xenopus (He et al., *Nature.* 374, 617 (1995)) and in segment polarity determination in Drosophila, where it was discovered as zest white 3 or shaggy (Bourouis et al., *EMBO, J.* 9, 2877 (1990); Siegfried et al., *Nature* 345, 825 (1990)). GSK-3 is a negative regulator of the wnt signaling pathway and it has been shown that loss of function and dominant negative mutations in GSK-3 beta lead to activation of the wnt pathway in Drosophila and Xenopus. Furthermore, the Wingless signaling pathway to GSK-3 is conserved in mammals (Cook et al., *EMBO, J.* 15, 4526 (1996); Stambolic et al., *Curr. Biol.* 6, 1664 (1996)) and the wnt signaling pathway plays a central role in the development of invertebrates and vertebrates. Thus, it is likely that the Wingless signaling pathway controls the nuclear export of NF-AT family members in the tissues where these genes are coexpressed. Accordingly, the invention also provides methods for regulating NF-AT translocation in a cell, comprising contacting the cell with a compound which modulates the Wingless signaling pathway. For example. translocation of NF-AT from the cytoplasm to the nucleus can be stimulated with activators of the wnt signaling pathway. In yet another embodiment, the invention provides a method for modulating the Wingless signaling pathway, comprising, e.g., modulating the activity of GSK-3. In one embodiment, the activity of GSK-3 is inhibited with an NF-AT peptide capable of binding to GSK-3, thereby activating the Wnt signaling pathway.

11. Exemplary Therapeutic Methods of the Invention

The methods of the invention can be used for treating or preventing in a subject a disease or condition that is associated with abnormal or aberrant T cell activation. Diseases or conditions involving, i.e., caused by or contributed to by, an excessive T cell activation include cancers, such as leukemias, inflammation, or autoimmune diseases. Alternatively, the methods of the invention can also be used to immunosuppress a subject, e.g., a recipient of a graft such as an organ or bone marrow transplant patient. Diseases or conditions involving an abnormally low T cell activation include immunosuppressed states, e.g., AIDS or conditions in which a subject has an infection. Thus, for example, a subject having a viral or bacterial infection can be treated by administering to the subject a compound which activates NF-ATc thereby activating the T cells of the subject and stimulating the immune system of the subject for fighting against the infection. For example, one can administer, either locally or systemically to the subject a pharmaceutically effective amount of a compound which increases NF-ATc localization in the nucleus, such as a compound which inhibits the intramolecular interaction between an NLS in NF-ATc and another portion of the NF-AT molecule. On the contrary, where a subject has an autoimmune disease, it is desirable to inhibit or reduce T cell activation. Thus, in this situation, one can administer to the subject a pharmaceutically effective amount of a compound which increases NF-ATc localization in the cytoplasm, e.g., a compound which shields the NLS of NF-ATc. Alternatively, a compound that activates GSK-3 and/or PKA activity and NF-AT phosphorylation can be administered to the subject.

Furthermore, since the Wingless signaling pathway involves GSK-3, the invention provides methods for treating diseases or disorders associated with the Wingless signaling pathway, such as cancer, e.g., breast cancer. For example, a disease can be treated or prevented by administering to a subject having such a disease a compound which is capable of inhibiting GKS-3, e.g, an NF-AT peptide capable of binding to GSK-3.

13. Exemplary Diagnostic and Prognostic Methods of the Invention

The invention provides diagnostic and prognostic methods, including methods for determining the state of immunosuppression in a subject and for determining an appropriate dose of immunosuppressant.

In one preferred embodiment of the invention, hybridization probes that specifically identify the NF-AT$_c$ gene may be used in methods for diagnosing genetic disease. For example, but not for limitation, the genetic disease thus diagnosed may involve a lesion in the relevant NF-AT$_c$ structural or regulatory sequences, or may involve a lesion in a genetic locus closely linked to the NF-AT$_c$ locus and which can be identified by restriction fragment length polymorphism or DNA sequence polymorphism at the linked NF-AT$_c$ locus. In a further preferred embodiment, NF-AT$_c$ gene probes are used to diagnose or identify genetic disease involving predisposition to immunological disease, wherein the amount or functionality of endogenous NF-AT$_c$ is sufficient for the individual to exhibit an increased probability of developing an immune disease, particularly an immune deficiency, arthritis, or autoimmune disease.

The invention also provides a method for determining the state of immunosuppression of a subject. In one embodiment, the method comprises determining the level of cytoplasmic and/or nuclear NF-AT polypeptide in a cell, preferably a lymphocyte, of a subject. The method can comprise obtaining a blood sample from a subject, and determining the amount of cytoplasmic and/or nuclear NF-AT, such as by immunohistochemistry using an antibody that binds specifically to NF-AT, as further described herein. In a preferred embodiment, the method comprises incubating the blood cells of the subject with a T cell activating compound and/or calcium ionophore prior to determining the cellular localization of NF-AT. In fact, if a patient is immunosuppressed, stimulation of lymphocytes of the patient will not result in significant translocation of NF-AT into the nucleus. A preferred T cell activator is a polyclonal activator, including lectins, concanavalin-A (Con-A) and phytohemagglutinin (PHA). Other activators include antibodies binding to invariable framework epitopes on the T cell receptor or CD3.

A preferred method for detecting NF-AT is by immunoflurorescence, using an antibody that binds specifically to one or more NF-ATc proteins. A preferred monoclonal antibody is the 7A6 antibody, described in Northrop et al.(1994) Nature 369:497.

In a preferred embodiment, the test is carried out on an enriched population of cells from the subject, such as a blood sample enriched in mononuclear cells. Peripheral blood mononuclear cells can be obtained, e.g., by separating the cells from a blood sample on a buffy coat, according to methods known in the art.

The level of nuclear and/or cytoplasmic NF-AT in lymphocytes of a subject can then be compared to the level of nuclear and/or cytoplasmic NF-AT in a control individual. A "control" or "normal" subject refers to a subject which has no known disease or condition involving NF-AT activation, e.g., inflammation, or autoimmune disease and which are not subjected to any treatment at the time the cell sample was obtained. Normal standards can be established from analysis of several cell samples from normal subjects. Samples from patients can then be analyzed and compared to this set of standards.

In a preferred embodiment, this diagnostic method can be used to monitor the state of immunosuppression in a subject who is receiving an immunosuppressive treatment, e.g., cyclosporin A. In one embodiment, cells are obtained from a subject, and the cellular localization of NF-AT is determined prior to and/or after incubation of the cells with a T cell activator, e.g., PHA. If the analysis reveals that the patient contains a high number of lymphocytes having nuclear NF-AT, i.e., activated lymphocytes, the patient should be given additional immunosuppressive drugs. Thus, a patient can be followed and an adequate amount of immunosuppressive drug can be administered to the patient, so that the patient does not receive excessive amounts of immunosuppressants, but received enough immunosuppressant to maintain him in an immunosuppressed state.

In another embodiment, the invention provides a method for determining the sensitivity of a subject to a particular immunosuppressive agent, e.g, cyclosporin A. In one embodiment, lymphocytes are obtained from a subject, the lymphocytes are incubated in vitro in the presence of various amounts of the immunosuppressive drug and for various times, and the cellular location of NF-AT is determined. The comparison of the results of this analysis with those obtained from the same analysis of lymphocytes from one or more normal subjects will indicate whether the subject is more, or alternatively, less sensitive, to the immunosuppressive drug than an average person. This analysis can also be performed in vivo. For example, a certain dose of immunosuppressive agent is administered to a subject and the cellular localization of NF-AT in lymphocytes of the subject is then determined at various time points and compared to that of a normal subject. Standards of normal subjects can also be obtained before hand and the results of the analysis can then be compared to these standards. Thus, based on the results of such tests, a physician can more appropriately predict the effective dose of immunosuppressant to administer to a subject, thereby avoiding administering an excessive of amount of immunosuppressant that could have toxic effects in the subject.

12. Methods for Rational Drug Design and Screening Assays

NF-AT$_c$ polypeptides, especially those portions which form direct contacts in NF-AT complexes, can be used for rational drug design of candidate NFAT-modulating agents (e.g., antineoplastics and immunomodulators). The substantially purified NF-AT$_c$ and the identification of NF-AT$_c$ as capable of forming intermolecular associations, e.g., with AP-1 and with DNA, as well as forming intermolecular associations, as provided herein, permits production of substantially pure NF-AT polypeptide complexes and computational models which can be used for protein X-ray crystallography or other structure analysis methods, such as the DOCK program (Kuntz et al. (1982) *J. Mol. Biol.* 161 269; Kuntz ID (1992) *Science* 257: 1078) and variants thereof Potential therapeutic drugs may be designed rationally on the basis of structural information thus provided. In one embodiment, such drugs are designed to prevent formation of a NF-AT$_c$ polypeptide: AP-1 polypeptide complex. In another embodiment, such drugs are designed to prevent the formation of intramolecular interactions in NF-AT. Thus, the present invention may be used to design drugs, including drugs with a capacity to inhibit binding of NF-AT$_c$ to form an NF-AT complex.

The invention further provides screening assays for identifying compounds which modulate the activity of NF-AT. The screening assays can be in vivo or in vitro and can be cell based or based on a cell free format. In a preferred embodiment, the assays allow the identification of compounds which modulate NF-AT translocation across the nuclear membrane. In an even more preferred embodiment, the screening assay comprises contacting an NF-AT NLS with an NF-AT molecule or portion thereof which is sufficient for binding to the NLS and with a test compound or a library of test compounds. In one embodiment, the NLS comprises the amino acid sequence CNKRKYSLN (SEQ ID NO: 53) (N-terminal NLS). In another embodiment, the NLS comprises the amino acid sequence GKRKK/R (SEQ ID NO: 67) (C-terminal NLS). The other component of the screening assay can be a peptide comprising the SRR, SP1, SP2, and/or SP3 of an NF-AT molecule. In a preferred embodiment, the screening assay comprises an N-terminal NLS and a peptide comprising the SRR region, which is phopshorylated. In another embodiment, the screening assay comprises a C-terminal NLS and a peptide comprising SP1, SP2 and/or SP3 regions which are phosphorylated.

In another embodiment of the screening assay, one component of the assay is an NF-AT polypeptide of portion thereof sufficient for binding to calcineurin and the other component is calcineurin or a portion thereof sufficient for binding to NF-AT. A portion of NF-AT can be an N-terminal portion, e.g., amino acids 1–418 of SEQ ID NO: 38. Thus, in one embodiment, the screening assay comprises contacting an NF-AT polypeptide with calcineurin and a test compound in conditions under which, but for the presence of the test compound, the NF-AT polypeptide are capable of interacting. The comparison of the binding of the two components of the assay in the presence and in the absence of a test compound will indicate whether the test compound inhibits, or alternatively stimulates, the interaction between NF-AT and calcineurin.

The above-described screening assays can generally be performed as follows. In this description, one component is NF-AT or a portion thereof and the other component is generally termed NF-AT binding partner, which can be, e.g., an NF-AT molecule or portion thereof, a kinase, or a phosphatase such as calcineurin. Thus, an exemplary screening assay of the present invention includes the steps of (a) forming a reaction mixture including: (i) an NF-AT polypeptide, (ii) an NF-AT binding partner, and (iii) a test compound; and (b) detecting interaction of the NF-AT and the NF-AT binding protein. The NF-AT polypeptide and NF-AT binding partner can be produced recombinantly, purified from a source, e.g., a cell extract, or chemically synthesized, as described herein. A statistically significant change (potentiation or inhibition) in the interaction of the NF-AT and NF-AT binding protein in the presence of the test compound, relative to the interaction in the absence of the test compound, indicates a potential agonist (mimetic or potentiator) or antagonist (inhibitor) of NF-AT bioactivity for the test compound. The compounds of this assay can be contacted simultaneously. Alternatively, an NF-AT protein can first be contacted with a test compound for an appropriate amount of time, following which the NF-AT binding partner is added to the reaction mixture. The efficacy of the compound can be assessed by generating dose response curves from data obtained using various concentrations of the test compound. Moreover, a control assay can also be performed to provide a baseline for comparison. In the control assay, isolated and purified NF-AT polypeptide or binding partner is added to a composition containing the NF-AT binding partner or NF-AT polypeptide, and the formation of a complex is quantitated in the absence of the test compound.

Complex formation between an NF-AT protein and an NF-AT binding partner may be detected by a variety of techniques. Modulation of the formation of complexes can be quantitated using, for example, detectably labeled proteins such as radiolabeled, fluorescently labeled, or enzymatically labeled NF-AT proteins or NF-AT binding partners, by immunoassay, or by chromatographic detection.

Typically, it will be desirable to immobilize either NF-AT or its binding partner to facilitate separation of complexes from uncomplexed forms of one or both of the proteins, as well as to accommodate automation of the assay. Binding of NF-AT to an NF-AT binding partner, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/NF-AT (GST/NF-AT) fusion proteins can be adsorbed onto glutathione sepharose beads (Sigma Chemical, St. Louis, Mo.) or glutathione derivatized microtitre plates, which are then combined with the NF-AT binding partner, e.g. an $^{35}$S-labeled NF-AT binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of NF-AT protein or NF-AT binding partner found in the bead fraction quantitated from the gel using standard electrophoretic techniques such as described in the appended examples.

Other techniques for immobilizing proteins on matrices are also available for use in the subject assay. For instance, either NF-AT or its cognate binding partner can be immobilized utilizing conjugation of biotin and streptavidin. For instance, biotinylated NF-AT molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with NF-AT can be derivatized to the wells of the plate, and NF-AT trapped in the wells by antibody conjugation. As above, preparations of an NF-AT binding protein and a test compound are incubated in the NF-AT presenting wells of the plate, and the amount of complex trapped in the well can be quantitated. Exemplary methods for detecting such complexes, in addition to those described above for the GST-immobilized complexes, include immunodetection of complexes using antibodies reactive with the NF-AT binding partner, or which are reactive with NF-AT protein and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the NF-AT binding partner. To illustrate, the NF-AT binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habib et al (1974) J Biol Chem 249:7130).

For processes which rely on immunodetection for quantitating one of the proteins trapped in the complex, antibodies against the protein, such as anti-NF-AT antibodies, can be used. Alternatively, the protein to be detected in the complex can be "epitope tagged" in the form of a fusion protein which includes, in addition to the NF-AT sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharmacia, N.J.).

An interaction between molecules, in particular between NF-AT and an NF-AT binding partner, can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the NF-AT protein, functional fragment thereof, NF-AT analog or NF-AT binding partner is then flown continuously over the sensor surface. A change in the resonance angle as shown on a signal recording, indicates that an interaction has occurred. This technique is further described, e.g., in BIAtechnology Handbook by Pharmacia.

Another screening assay that can be used targets the identification of compounds which interact with an NF-AT molecule, or binding partner. An illustrative example of such an assay includes the steps of contacting an NF-AT protein or functional fragment thereof or an NF-AT binding partner with a test compound or library of test compounds and detecting the formation of complexes. For detection purposes, the molecule can be labeled with a specific marker and the test compound or library of test compounds labeled with a different marker. Interaction of a test compound with an NF-AT protein or fragment thereof or NF-AT binding partner can then be detected by determining the level of the two labels after an incubation step and a washing step. The presence of two labels after the washing step is indicative of an interaction.

The invention also provides screening assays for identifying compounds which modulate phosphorylation or depohosphorylation of an NF-AT molecule. In one embodiment, the assay is an in vitro assay. In one embodiment, the assay comprises contacting a non phosphorylated, or partially phosphorylated NF-AT polypeptide with a cell extract, or with one or more purified kinases, such as GSK-3 and PKA, and other necessary components of an in vitro kinase assay, including a source of phosphate and with or without a test compound and under conditions under which phosphorylation of NF-AT occurs. The comparison of the state of phosphorylation of NF-AT in the presence and in the absence of a test compound will indicate whether the test compound decreases or inhibits, or alternatively increases or stimulates, the phosphorylation of NF-AT. The kinase assay and preparation of a cellular extract can be performed as described in the Examples. When the NF-At polypeptide is partially phosphorylated prior to use in the kinase assay, this can be achieved, e.g., by prior incubation of a non-phosphorylated NF-AT with PKA. An NF-AT phosphorylated with PKA can be use as a component of an assay for identifying compounds which inhibit phosphorylation by GSK-3, since GSK-3 phosphorylates peptides which have been phosphorylated by PKA. Non phosphorylated or partially phosphorylated NF-AT can also be obtained from cells containing active, e.g., nuclear NF-AT. Thus, NF-AT substrate for use in this assay can be obtained from or consist in a nuclear extract of activated T cell.

In another embodiment, the kinase assay is an in vivo kinase assay. The assay can comprise incubating a cell expressing non phophorylated or partially phosphorylated NF-AT, e.g, an activated T cell, with a test compound and comparing the state of phosphorylation of NF-AT in the presence and in the absence of the test compound. A variation in the state of phosphorylation will indicate that the test compound is capable of modulation phosphorylation of NF-AT. The state of phosphorylation of NF-AT can be determined by, e.g., by performing the incubation of the cells in the presence of labeled, e.g., radioactive, phosphate (e.g, ATP), and determining the amount of label present in an immunoprecipitate with an NF-AT specific antibody. Alternatively, the state of phosphorylation can be performed by Western blot analysis, optionally coupled with immuno-precipitations.

In another embodiment, the invention provides screening assays for identifying compounds which modulate dephosphorylation of NF-AT. In one embodiment, the assay comprises incubating a phosphorylated NF-AT polypeptide with a cell extract or with one or more phosphatases, e.g, calcineurin, in conditions under which the NF-AT polypeptide is phosphatased, and a test compound. NF-AT can be phosphorylated in vitro with PKA and optionally GSK-3, or NF-AT can be phosphorylated with a cell extract. NF-AT can also be isolated from or present in a cell extract. The comparison of the state of phosphorylation of NF-AT after a phospatase reaction in the presence and in the absence of a test compound will indicate whether the test compound is capable of modulating dephosphorylation of NF-AT. A higher level of phosphorylated NF-AT in the presence of the test compound relative to the level of phosphorylation in the absence of the test compound indicates that the compound is an inhibitor of NF-AT dephosphorylation. A lower level indicates that the test compound is a stimulator of dephosphorylation. The state of phosphorylation of NF-AT can be determined as described above.

The identification of compounds which modulate dephosphorylation of NF-AT can also be identified in vivo assays. For example, a cell containing phosphorylated NF-AT, e.g., a resting T cell, is incubated in the presence or absence of a test compound and the state of phosphorylation of NF-AT is determined as described above.

Since it has been shown herein that GSK-3 and PKA phosphorylate NF-AT$_c$ the invention also provide screening assays for identifying modulators of GSK-3 and PKA. Such screening assays may comprise identifying compounds which specifically interact with GSK-3 or PKA and thereby modify their activity. Screening assays may also comprise incubating GSK-3 or PKA with a GSK-3 or PKA binding partner, respectively, and a test compound and determining whether the test compound influences the interaction between the proteins. These assays can be conducted as further described herein. Modulators of GSK-3 and PKA can also be identified in in vivo screening assays.

In yet another embodiment, the invention provides an in vivo screening assay for identifying compounds which modulate nuclear translocation of NF-AT comprising incubating or treating a cell with or without a test compound and determining the localization of NF-AT in the cell, i.e., whether NF-AT is present in the cytoplasm and/or in the nucleus of the cell. In one embodiment, a cell containing NF-AT in the cytoplasm, e.g., a resting T cell or a Jurkat cell, is incubated with a test compound and the cellular localization of NF-AT is determined. The presence of NF-AT in the nucleus indicates that the test compound stimulates the translocation of NF-AT from the cytoplasm to the nucleus. In another embodiment, a cell containing NF-AT in the cytoplasm is incubated with a test compound and an agent which activates NF-AT, i.e., an agent which stimulates its translocation to the nucleus and the cellular localization of NF-AT is determined. If more NF-AT is localized in the cytoplasm of the cell incubated with the test compound relative to a cell that was not treated with the test compound, the test compound inhibits the translocation of NF-AT from the cytoplasm to the nucleus and is thus an NF-AT inhibitor. Alternatively, is more NF-AT is present in the nucleus of the cell incubated with the test compound, relative to the cell that was not incubated with the test compound, the test compound is a stimulator or activator of NF-AT.

In another embodiment, the screening assay comprises incubating a cell containing nuclear NF-AT, e.g., an activated T cell such as a T cell treated with ionomycin, is contacted with a test compound and the cellular localization of NF-AT is determined. If more NF-AT is localized in the nucleus in the cell treated with the test compound versus the cell that was not treated with the test compound, the test compound is a compound which is capable of maintaining NF-AT in an activated state, i.e., in the nucleus. If more NF-AT is localized in the cytoplasm in the cell treated with the test compound relative to the cell that was not treated with the test compound, the test compound is capable of deactivating NF-AT, i.e., to stimulate its translocation to the cytoplasm.

The cellular localization of an NF-AT molecule can be determined, by, e.g., detecting its localization within a cell using an antibody or other agent capable of specifically interacting with NF-AT. For example, NF-AT can be detected by immunfluorescence, such as described in the Examples. In another embodiment, the cell can be transfected with a nucleic acid encoding an NF-AT polypeptide that is fused to a tag or marker, that can be detected. For example, the cell can be made to express an NF-AT polypeptide that is fused to a myc tag and the NF-AT fusion polypeptide can then be detected with an antibody binding specifically with a myc tag.

A person of skill in the art will recognize that any of the above described screening assays can easily be adapted for use in screening libraries of compounds. The compounds identified using any of the screening assays of the invention are also within the scope of the invention, as well as pharmaceutical compositions and kits comprising such.

13. Kits

The compounds of the invention can be provided in the form of kits, for use in treating, preventing, or diagnosing diseases or conditions in which one desires to modulate the activity of T cells. For example, the invention provides kits for activating NF-ATc in a subject, comprising a compound which is capable of inhibiting intramolecular interaction of an NLS in NF-AT, or which is capable of inhibiting GSK-3 and/or PKA.

In a preferred embodiment of the invention, the kit of the invention provides reagents for determining the level of immunosuppression of a subject, such as a subject who is undergoing a treatment with an immunosuppressive drug. In one embodiment, the kit comprises a reagent for determining the cellular localization of NF-AT, such as an antibody that specifically binds to NF-AT. Other reagents that can be included in the kit are control reagents or standards, against which the results of the test can be compared. In some embodiments, the standard is a table or curve indicating values in normal, e.g., non immunosuppressed, individuals. The kit may also contain other reagents, such as a secondary reagent, e.g., fluorescein labeled antibody and any buffer. In addition to monitoring the extent of immunosuppression of a subject, the kit of the invention can also be used to predict the sensitivity of a subject to a certain drug, e.g., an immunosuppressive drug.

14. Methods for Forensic Identification

The NF-AT$_c$ polynucleotide sequences of the present invention can be used for forensic identification of individual humans, such as for identification of decedents, determination of paternity, criminal identification, and the like. For example but not limitation, a DNA sample can be obtained from a person or from a cellular sample (e.g., crime scene evidence such as blood, saliva, semen, and the like) and subjected to RFLP analysis, allele-specific PCR, or PCR cloning and sequencing of the amplification product to determine the structure of the NF-AT$_c$ gene region. On the basis of the NF-AT$_c$ gene structure, the individual from which the sample originated will be identified with respect to his/her NF-AT$_c$ genotype. The NF-AT$_c$ genotype may be used alone or in conjuction with other genetic markers to conclusively identify an individual or to rule out the individual as a possible perpetrator.

In one embodiment, human genomic DNA samples from a population of individuals (typically at least 50 persons from various racial origins) are individually aliquoted into reaction vessels (e.g., a well on a microtiter plate). Each aliquot is digested (incubated) with one or more restriction enzymes (e.g., EcoRI, HindIII, SmaI, BamHI, SalI, NotI, AccI, ApaI, BglII, XbaI, PstI) under suitable reaction conditions (e.g. see New England Biolabs 1992 catalog). Corresponding digestion products from each individual are loaded separately on an electrophoretic gel (typically agarose), electrophoresed, blotted to a membrane by Southern blotting, and hybridized with a labeled NF-AT$_c$ probe (e.g., a full-length human NF-ATc cDNA sequence of FIG. 1). Restriction fragments (bands) which are polymorphic among members of the population are used as a basis to discriminate NF-AT$_c$ genotypes and thereby classify individuals on the basis of their NF-AT$_c$ genotype.

Similar categorization of NF-AT$_c$ genotypes may be performed by sequencing PCR amplification products from a population of individuals and using sequence polymorphisms to identify alleles (genotypes), and thereby identify or classify individuals.

The present invention is further illustrated by the following examples which should not be construed as limiting in any way. The contents of all cited references (including literature references, issued patents, published patent applications as cited throughout this application are hereby expressly incorporated by reference. The practice of the present invention will employ., unless otherwise indicated, conventional techniques of cell biology, cell culture, molecular biology, transgenic biology, microbiology, recombinant DNA, and immunology which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. : 4,683,195; Nucleic Acid Hybridization(B. D. Hames & S. J. Higgins eds. 1984); Transcription And Translation (B. D. Haines & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986)); Manipulating the Mouse Embryo, (Cold Spring Harbor Laboratory Press, Cold Spring Harbor, N.Y., 1986).

EXPERIMENTAL EXAMPLES

Overview

We have purified two related proteins encoded by separate genes that represent the preexisting or cytosolic components of NF-AT. Expression of a full length cDNA for one of these proteins, NF-AT$_c$, activates the IL-2 promoter in non-T lymphocytes, while a dominant negative of NF-AT$_c$ specifically blocks activation of the IL-2 promoter in T lymphocytes, indicating that NF-AT$_c$ is required for IL-2 gene expression and is responsible for the restricted expression of IL-2. NF-AT$_c$ RNA expression is largely restricted to lymphoid tissues and is induced upon cell activation. The second protein, NF-AT$_p$, is highly homologous to NF-AT$_c$ over a limited domain, but exhibits wider tissue distribution and is highly expressed in tissues characterized by Ca++-dependent regulation. Together these proteins are members of a new family of DNA bindingproteins, which are distantly related to the Dorsal/Rel family (Nolan and Baltimore (1992) Current Biology Ltd. 2: 211–220). Agents that increase intracellular Ca++ or that activate protein kinase C independently produce alterations in the mobility of NF-AT$_c$, indicating that distinct signaling pathways converge on NP-ATC to regulate its function.

Since our previous work indicated that the cytosolic component of NF-AT was present at relatively low concentrations in human lymphoid cell lines (Northrop et al. (1993) *J. Biol. Chem.* 268: 2917–2923), we chose to purify NF-AT$_c$ from bovine thymus. Amino acid sequence, obtained from 6 peptides, was used to isolate two overlapping human cDNA clones spanning 2742 nucleotides (FIG. 1). The cDNA encodes a protein of 716 amino acids with a predicted molecular weight of 77,870. An in-frame stop codon upstream from the initiator methionine indicates that the entire NF-AT$_c$ protein is encoded by this cDNA. A unique repeated sequence of 13 residues was also identified. The carboxy-terminal half of NF-AT$_c$ shows limited similarity to the DNA binding and dimerization regions of the Dorsal/Rel family of transcription factors (FIG. 4, for review, Nolan and Baltimore (1992) *Current Biology, Ltd.* 2: 211-220) however, NF-AT$_c$ appears to be the most distantly related member of the group. There are a significant number of amino acid changes resulting in charge reversals between the Rel family members and NF-AT$_c$, suggesting that charge might be conserved at these positions to maintain salt bridges. Six additional peptides obtained from the purified bovine protein are derived from the bovine homolog of NF-AT$_p$, a cDNA fragment of which was reported by McCaffrey et al. (1993) *Science* 262: 750–754). Comparison of NF-AT$_c$ and NF-AT$_p$ reveals that they are products of distinct genes with 73% amino acid identity in the Rel similarity region (FIG. 4), however, there is very little similarity outside this region. A murine cDNA for NF-AT$_c$ was isolated and the predicted protein was found to be 87% identical to human NF-AT$_c$, and distinctly different from murine NF-AT$_p$.

Example 1

Determination of the Nucleotide and Amino Acid Sequence of Human NF-AT$_c$ cDNA

This example represents the isolation and purification of this novel human NF-AT protein, NF-AT$_c$, the determination of the amino acid sequence of its fragments and the isolation and sequencing of the cDNA clone encoding this protein.

The protein was purified from bovine thymus glands obtained from newborn calves. Approximately 20 bovine thymuses were homogenized to make a cytosolic extract which was then subjected sequentially to 1) ammonium sulfate precipitation, 2) sulphopropyl Sepharose chromatography, 3) heparin agarose chromatography, 4) affinity chromatography using a multimerized binding site for NF-AT, with the sequence 5'-ACGCCCAAAGAGGAAAATTTGTTTCATACA-3' (SEQ ID NO: 73) coupled to sepharose CL4B, and 5) HPLC on a reverse phase C4 column. The resulting purified protein was subjected to cleavage with LysC/ArgC and fragments isolated by HPLC. The sequences of these individual fragments were then determined by automated Edman degradation. Sequences obtained included: LRNSDIELRKGET-DIGR (SEQ ID NO: 74) and LRNADIELR.(SEQ ID NO: 75). Degenerate oligos corresponding to GETDIG (SEQ ID NO: 76) (reverse primer) and RNADIE (SEQ ID NO: 77)(forward primer) were made. The degenerate oligo PCR primers had the following sequences:
A forward: (A/C)GIAA(C/T)GCIGA(C/T)AT(A/C/T)GA(A/G) (SEQ ID NO: 78)
A reverse: ICC(A/G/T)AT(A/G)TCIGT(C/T)TCICC (SEQ ID NO: 79)

To isolate the cDNA, oligonucleotide probes were made corresponding to the determined amino acid sequence and used as PCR primers to isolate a 45 base fragment from bovine cDNA prepared from the bovine thymus. The bovine PCR product comprised the nucleotide sequence CTG CGG AAA which encodes -L-R-K-. The same 45 bp fragment can be amplified from human and mouse sources.

This bovine PCR product was then used to screen a cDNA library of the human Jurkat T cell line. Clones were isolated at frequencies of about 1 in 100,000 to 1 in 200,000. A total of five human cDNA clones of various lengths were isolated. Two overlapping clones, one containing the 5' end and one containing the 3' end were ligated together using a unique EcoRI restriction site present in each clone, to produce a full-length cDNA which corresponded in length to the messenger RNA determined by Northern blotting.

The sequence of the NF-AT$_c$ cDNA was determined by the Sanger method and the complete nucleotide and predicted amino acid sequence is shown in FIG. 1. The initiator methionine indicated in FIG. 1 (boldface, indicated) was determined by fusing this reading frame to a glutathione transferase gene and transfecting the resultant clone into bacteria. The resultant clone produced a fusion protein of the proper molecular weight, indicating that the reading frame designated with the initiator methionine is indeed the correct reading frame. The position of the stop codon was determined by a similar procedure. In addition, the stop codon corresponds to the reading frame for nine of the determined amino acid sequences.

Figure 4C:
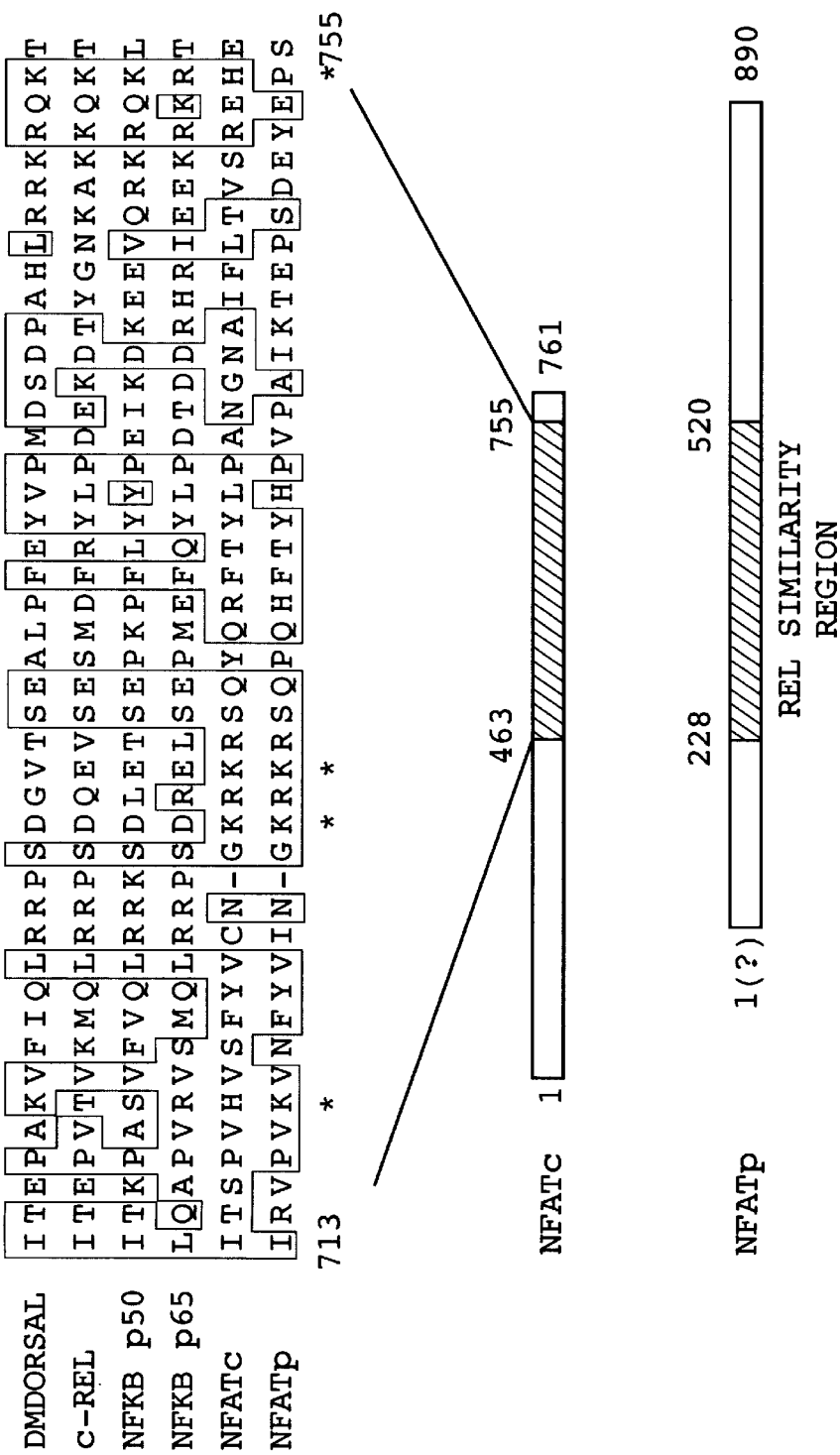

The total NF-AT$_c$ protein structure was aligned against individual Rel proteins using a MacIntosh shareware program called DOTALIGN utilizing the alignment parameters of the FASTA programs. Significant homology was observed that corresponded to the Rel domains of these proteins. Enhanced amino acid residue alignment was done using ALIGN from the same suite of programs. Alignment of the Rel similarity regions of NF-AT$_c$ and NF-AT$_p$ was done by hand with no insertions necessary, The Miyata alphabet (Miyata et al. (1979) *J. Mol. Evol.* 12: 214–236) was used to determine similar residues. FIG. 4 shows results of such sequence alignments.

Example 2

Expression of NF-AT$_c$ in T and Non-T Cells

The cDNA shown in FIG. 1 was fused to the Hemophilus influenza hemaglutinin (HA) 12 amino acid epitope tag in the determined reading frame and operably linked to the SRα promoter in the vector pBJ5 (Lin et al, 1990, Science 249:677–679). The resultant construct was transiently transfected by electroporation into Jurkat human T lymphocytes, and into Cos fibroblast cells. Expression of the epitope-tagged NF-AT$_c$ protein was determined by Western blotting of whole cell extracts prepared from the transfected cells, using an antibody (12CA5, Berkeley Antibody Co., CA) that detects the HA epitope. FIG. 2 shows that NF-AT$_c$ cDNA construct is able to express a protein of appoximately 120 kDA corresponding precisely in size to that of the purified protein, in both Jurkat T cells and Cos cells (see lanes 3 and 6 labeled NF-AT*. Lane 2 shows as control, NF-AT without the epitope tag which cannot be detected in the Western blot).

Example 3

Transfection of NF-ATc Activates Transcription in Both Cos and Jurkat Cells

The NF-ATc cDNA was operably linked to a portion of the SV40 early gene promoter and the HIV transcription regulatory regions in the pBJ vector. This expression vector was co-tranfected into Jurkat and Cos cells with either a) three copies of NF-AT binding site linked to and directing transcription of luciferase (results shown in FIGS. 3A and 3B) the entire IL-2 enhancer/promoter directing transcription of luciferase (results shown in FIG. 3B). Cytosolic extracts were prepared and luciferase assays carried out by standard procedures (de Wet et at, 1987, Mol. Cell. Biol. 7:724–837).

Figure 3A:
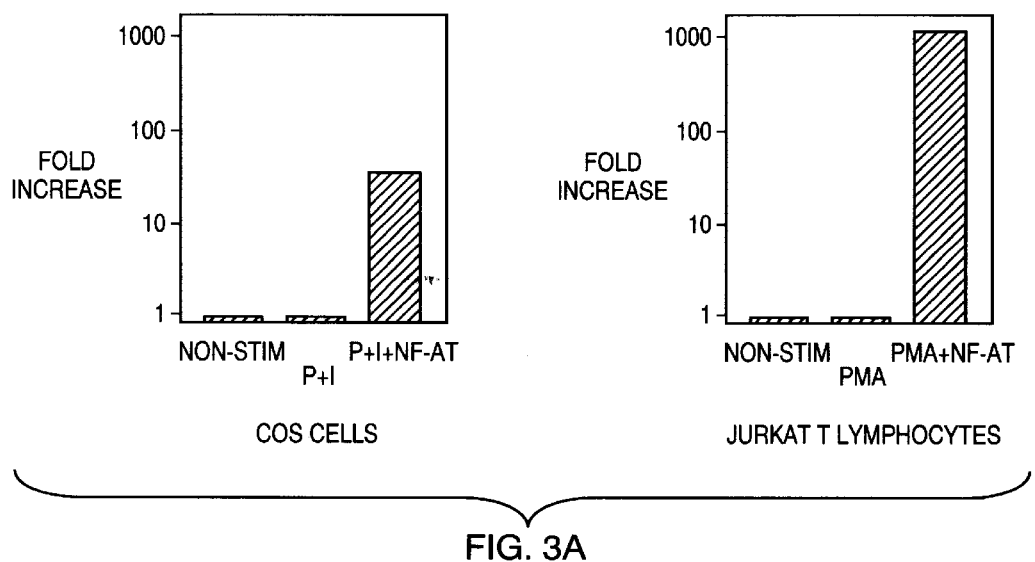
FIGS. 3A and 3B show that the NF-$AT_c$ cDNA clone encodes a protein that activates transcription from an NF-AT site and is capable of activating the IL-2 promoter in non-T cells.
Figure 3B:
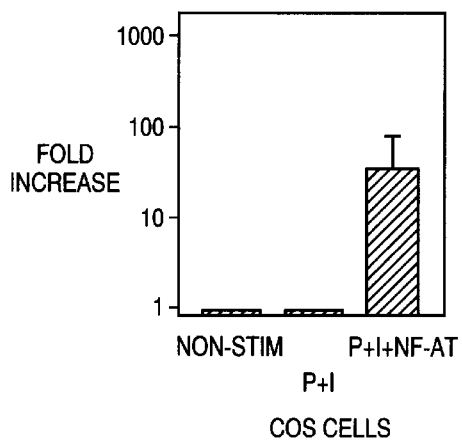

The results demonstrate that in both Cos cells and Jurkat cells, overexpression of the NF-AT$_c$ protein dramatically enhances NF-AT-dependent transcription by 50–1000 fold (see FIG. 3A). In addition, overexpression of the NF-ATc protein in Cos cells activates the IL-2 promoter, which in the absence of NF-AT$_c$ cannot otherwise be activated (see FIG. 3B).

These results indicate that the cDNA clone encodes a functional NF-AT$_c$ protein and that NF-AT$_c$ is the protein which restricts expression of interleukin-2 to T cells.

Example 4

NF-AT$_c$ mRNA and Protein Expression

Figure 5A:
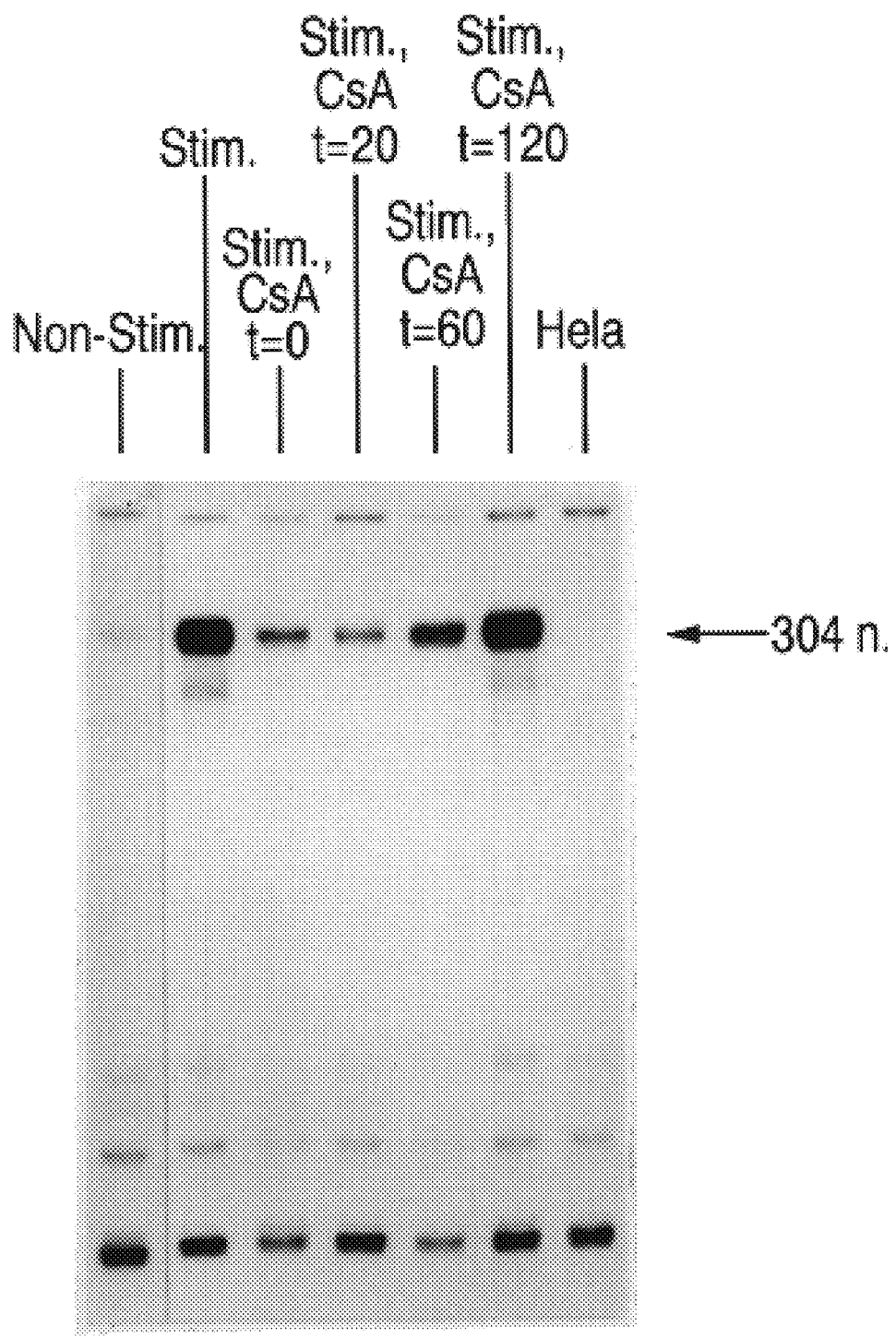
FIG. 5A shows ribonuclease protection for human NF-$AT_c$ with RNA from Jurkat cells (lanes 1–6) or Hela cells (lane 7). The expected specific ribonuclease-resistant fragment is 304 nucleotides (arrow). Hela cells were non-stimulated. Jurkat cells were either non-stimulated or stimulated with 20 ng/ml PMA and 2 uM ionomycin for 3 hours, plus or minus 100 ng/ml CsA added at the indicated times after stimulation.
Figure 5B:
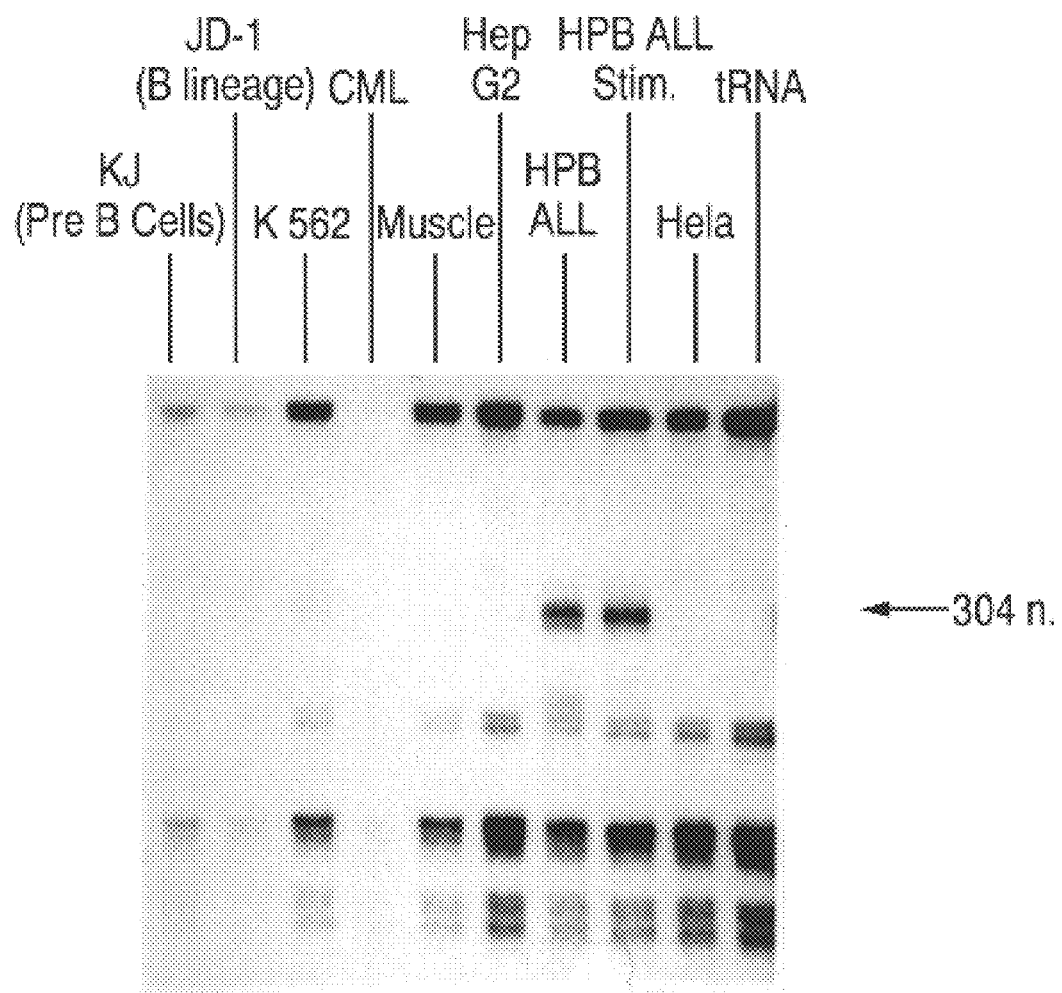
FIG. 5B shows RNA from the following human cells: KJ (preB cell ALL), JD-1 (B cell lineage ALL), K562 (erythroleukemia cell line), CML (bone marrow cells from a patient with a myeloid leukemia), human muscle tissue, Hep G2 (liver cell line), HPB ALL (T cell line, nonstimulated or stimulated with 2 ug/mi PHA and 50 ng/ml PMA for 30 minutes), and Hela cells analyzed by ribonuclease protection. A longer exposure of this gel indicates that the K562 cell line contains a small amount of NF-$AT_c$ transcript.
Figure 5C:
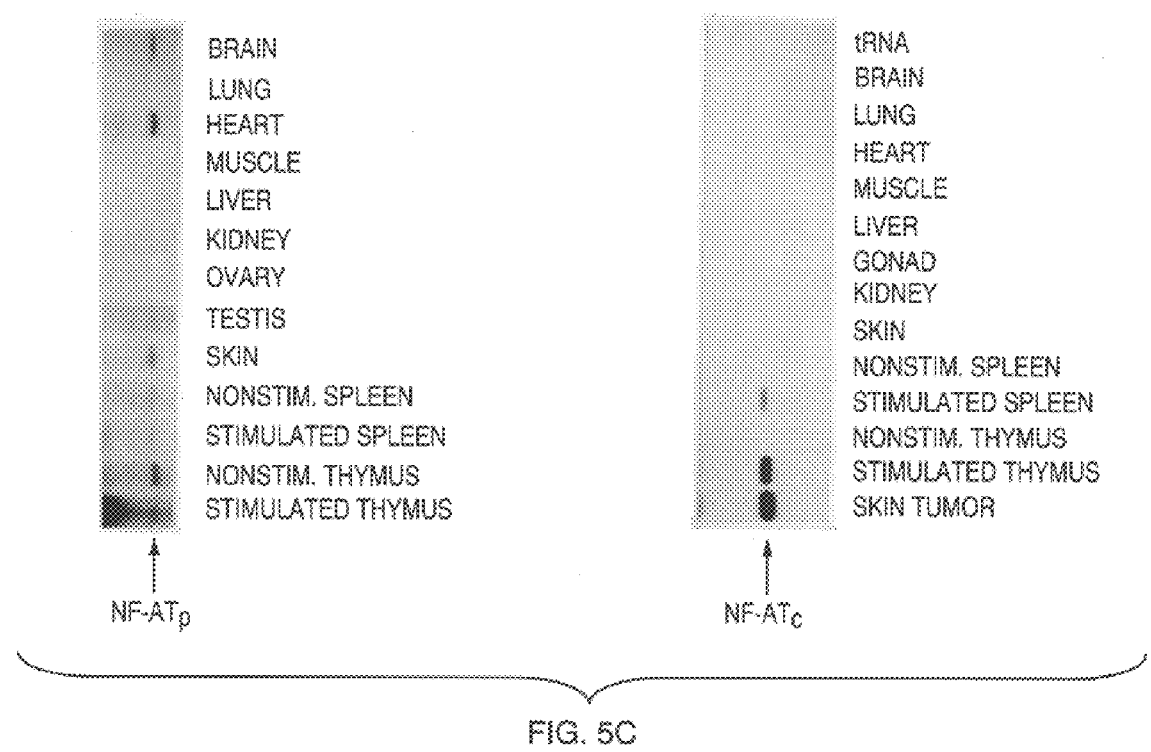
FIG. 5C shows NF-$AT_c$ (upper panel) and NF-$AT_p$ (lower panel) mRNA expression in mouse tissues and a skin tumor derived from NF-AT-Tag transgenic mice (Verweij et al. (1990) *J. Biol. Chem* 265: 15788–15795). Cells were either non-stimulated or stimulated with 20 ng/ml PMA and 2 uM Ionomycin for 3 hours. RNA was measured by quantitative ribonuclease protection using murine cDNA probes. The predicted size of the fragment homologous to the probe is indicated by the arrows.
Figure 6A:
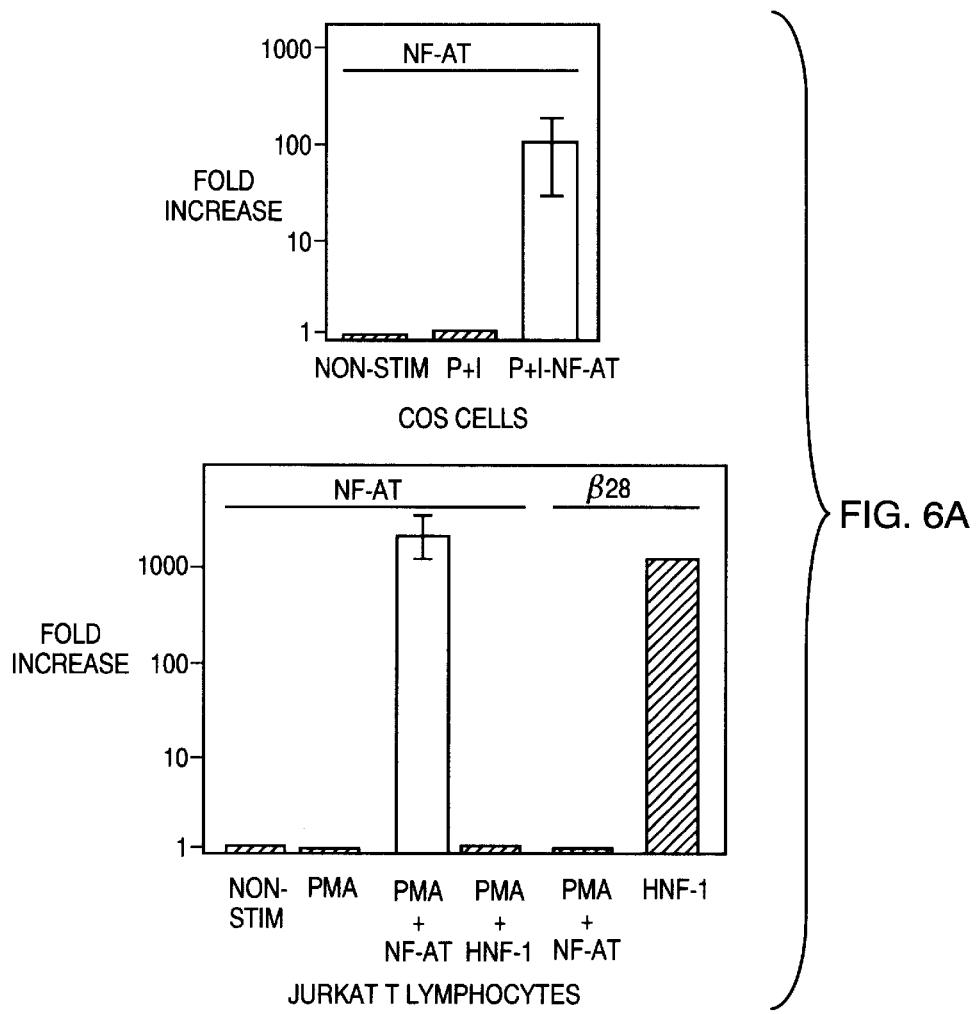
FIG. 6A shows Cos cells and Jurkat cells that were transfected with reporter constructs for NF-AT or HNF-1 (β28). Co-transfected expression vectors for NF-AT$_c$ (+NF-AT) or HNF-1α (+HNF-1) were included where indicated, otherwise empty pBJ5 vector was included. Cells were stimulated as indicated: PMA, P+I (PMA plus ionomycin).
Figure 6B:
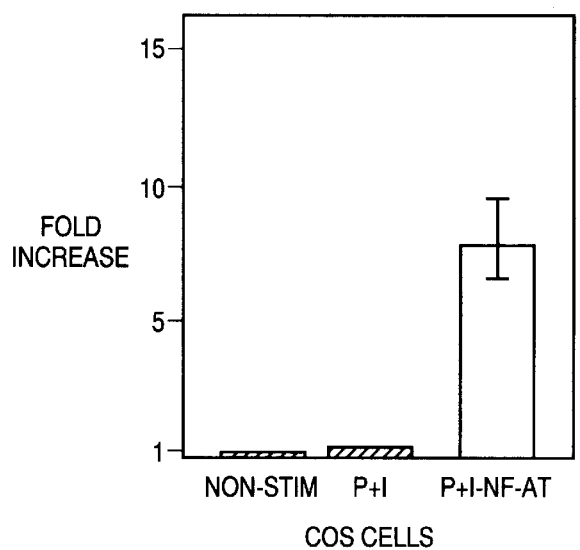
FIG. 6B shows Cos cells that were transfected with IL-2 luciferase and with expression vectors as in panel A. Stimulations were as in panel A. Data in panel A and panel B are expressed as fold induction of luciferase activity over non-stimulated value with empty pBJ5 vector. Bars represent mean and range of 2–3 independent transfections.
Figure 6C:
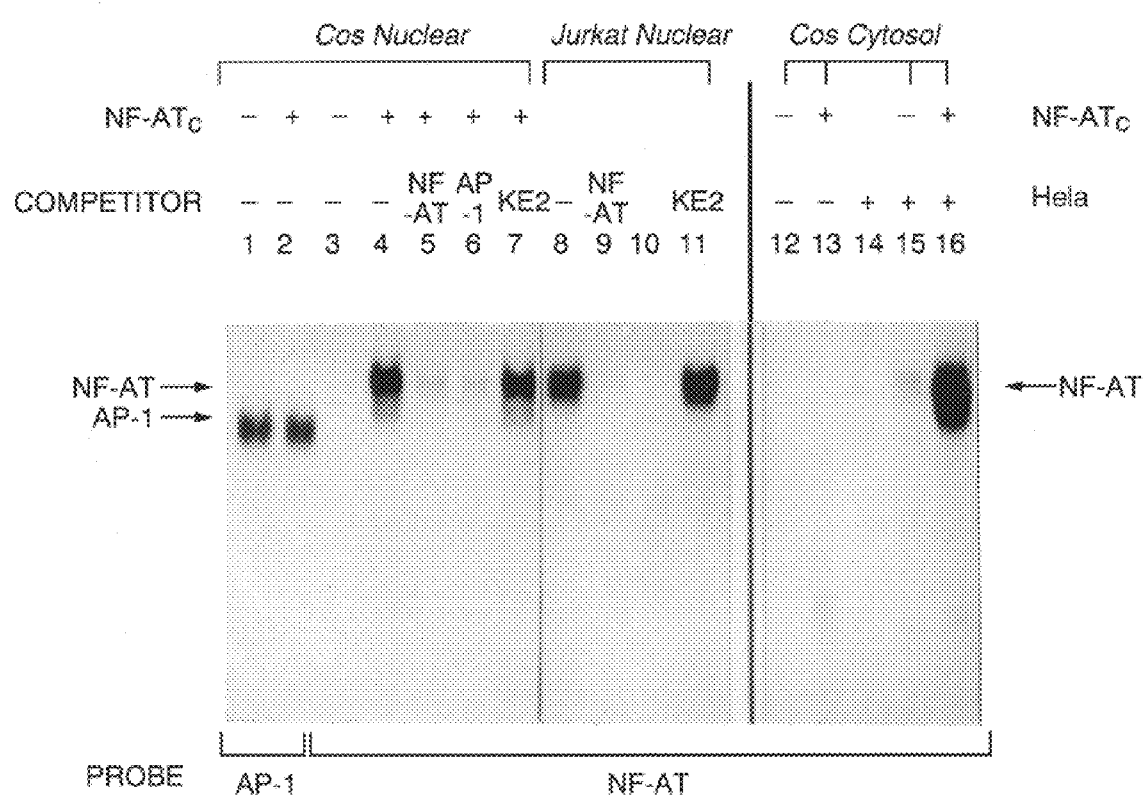
FIG. 6C shows that expression of NF-AT$_c$ in Cos cells gives rise to specific DNA binding activity. Gel mobility shifts using nuclear extracts from Cos cells transfected with pBJ5 (lanes 1 and 3), with NF-AT$_c$ (lanes 2 and 4–7), from non-transfected Jurkat cells (lanes 8–11) or using cytosols from pBJ5- or NF-AT$_c$-transfected Cos cells (lanes 12–13, 15–16) combined with Hela nuclear extract (lanes 15–16). Lane 14, Hela nuclear extract alone. Labeled AP-1 (lanes 1–2) or NF-AT (lanes 3–16) probes and cold competitor oligonucleotides are indicated. Arrows indicate specific AP-1 and NF-AT complexes.
Figure 6D:
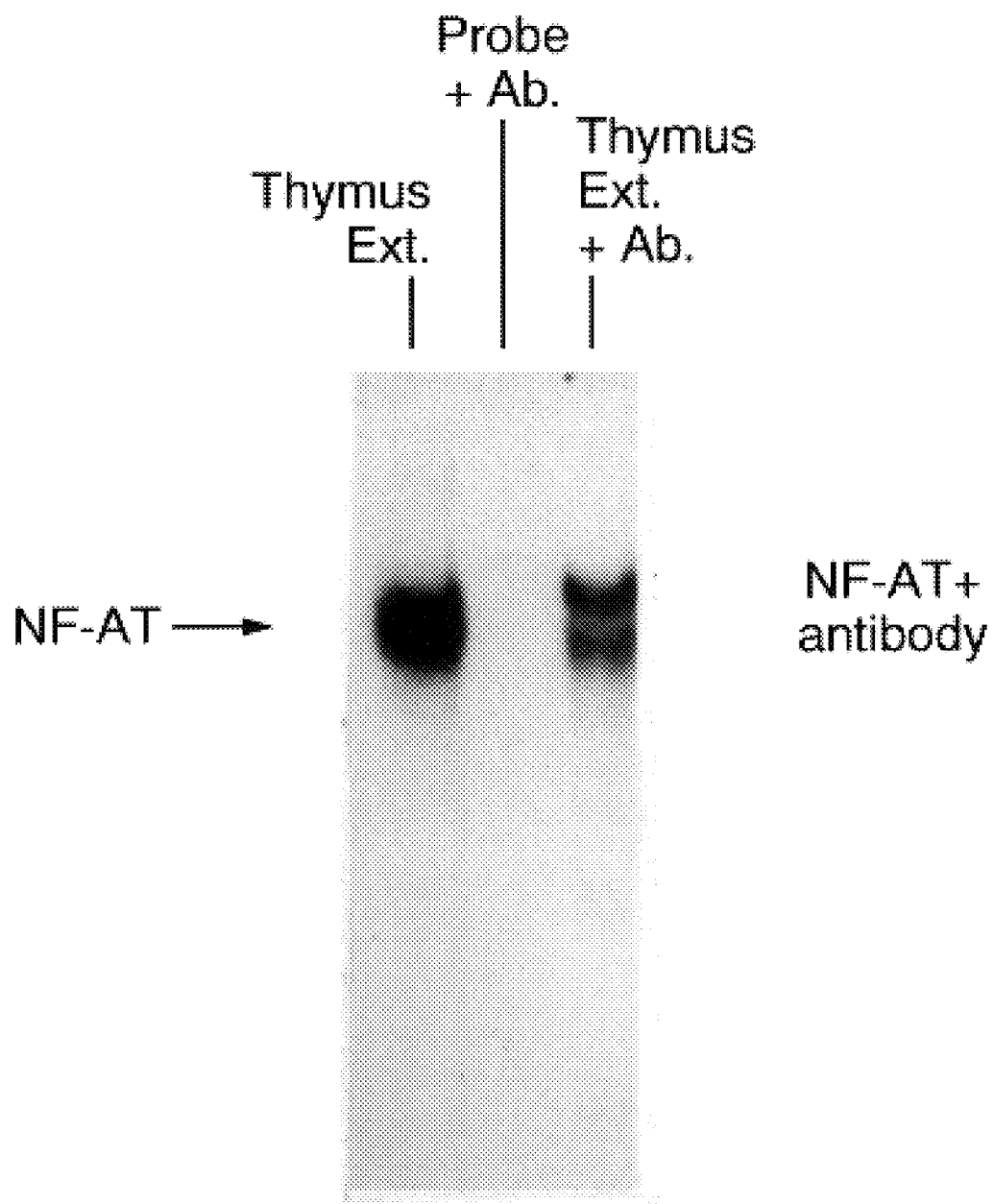
FIG. 6D shows antisera induced supershift of NF-AT NF-AT and AP-1 gel mobility shifts using nuclear extracts from stimulated Jurkat cells or murine thymocytes. Either no antisera, preimmune, or one of two different immune antisera was included as indicated. Arrows indicate specific NF-AT or API complexes or supershifted NF-AT complexes (*).

NF-AT$_c$ mRNA is absent in Hela cells (FIG. 5, panel a, lane 7), a cell line incapable of IL-2 or NF-AT-dependent transcription, but is inducible in Jurkat cells (FIG. 5, panel a). This induction is sensitive to cyclosporin A, (CsA), indicating that NF-AT$_c$ may participate in an autostimulatory loop as CsA has been shown to block its nuclear association (Flanagan et al. (1991) Nature 352: 803–807). Two B cell lines, muscle tissue, Hep G2 cells and myeloid leukemia cells do not express NF-AT$_c$ mRNA (FIG. 5, panel b). These observations are consistent with the observed T cell-restricted pattern of IL-2 transcription and NF-AT activity. Previous studies (Verweij et al. (1990) J. Biol. Chem 265: 15788–15795) revealed NF-AT-dependent transcription predominantly in spleen, thymus and skin of transgenic mice expressing an NF-AT-dependent reporter gene. Consistent with these observations, murine NF-AT$_c$ mRNA shows the same pattern of expression (FIG. 5 panel c). Small amounts of NF-AT$_c$ expression are seen in lung and heart, however, this may be due to contamination with circulating T cells. Murine NF-AT$_p$ mRNA, also assayed by quantitative ribonuclease protection, was found to be expressed at approximately equal levels in brain, heart, thymus and spleen (FIG. 5, panel c). In contrast to NF-AT$_c$, NF-AT$_p$ was not inducible by PMA and ionomycin (FIG. 5, panel c).

METHODS. Specific human or mouse NF-AT$_c$ or mouse NF-AT$_p$ cDNA fragments were used as templates for the synthesis of RNA transcripts. Ribonuclease protection was done according to Melton et al. (1984) Nucl. Acids. Res. 12: 7035–7056) using 10 μg of total RNA. Splenocytes and thymocytes were isolated and treated as described (Verweij et al. (1990) J. Biol. Chem 265: 15788–15795) before isolating RNA, otherwise whole tissue was used.

Example 5

Functional Expression of NF-AT$_c$

NF-AT luciferase and IL-2 luciferase have been described (Northrop et al. (1993) J. Biol. Chem. 268: 2917–2923). β28 luciferase was constructed by inserting a trimerized HNF-1 recognition site (β28) in place of the NF-AT recognition sites in NF-AT luciferase. The plasmid pSV2CAT (Gorman et al. (1982) Mol. Cell. Biol. 2: 1044–1050) was used as an internal control for transfection efficiency. Cells were transfected with 1.5 ug of luciferase reporter and 3 ug of expression construct as described. After 20 hours of growth, cells were stimulated for 8 hrs. with 20 ng/ml PMA plus or minus 2 uM ionomycin, and harvested for luciferase (de Wet et al. (1987) Mol. Cell. Biol. 7: 725–737) and CAT assays (Gorman et al. (1982) Mol. Cell. Biol. 2: 1044–1050).

Cos cells were transfected with epitope tagged NF-AT$_c$ as described. Cos cells, Jurkat cells, and murine thymocytes were stimulated for 3hr. with PMA and ionomycin. Hela cells were stimulated for 3 hr with PMA alone and nuclear extracts prepared as described (Fiefing et al. (1990) Genes & Dev. 4: 1823–1834). Cytosols were prepared from non-stimulated Cos cells. Gel mobility shifts were performed as previously described (Flanagan et al. (1991) Nature 352: 803–807; Northrop et al. (1993) J. Biol. Chem. 268: 2917–2923). Antisera were raised in mice immunized with bacterially expressed glutathione S-transferase fusion proteins using the vector pGEX-3× (Pharmacia) and purified on glutathione agarose. Fusion proteins contained NF-AT$_c$ residues 12 to 143 (immune-l) and 12 to 699 (immune-2).

NF-AT$_c$, expressed in non T cell lines specifically activated transcription from the NF-AT site and the IL-2 promoter, (FIG. 6 panel a (left), and FIG. 6 panel b). In transiently transfected Jurkat cells, overexpression of NF-AT$_c$ activated an NF-AT-dependent promoter but not an HNF-1 dependent promoter (FIG. 6 panel a (right)) or an AP-1-dependent promoter. Transfection of the NF-AT$_c$ cDNA gives rise to DNA binding activity that is indistinguishable from endogenous NF-AT (FIG. 6 panel c, lanes 1–4). Antibody directed against the HA epitope encoded by the transfected cDNA induces a supershift of the NF-AT complex indicating that NF-AT$_c$ participates in this activity. The nuclear NF-AT activity in transfected Cos cells comigrates with, and has the same binding specificity as, the native nuclear complex in T-cells (FIG. 6 panel c, lanes 4–11). cytosolic extracts from NF-ATc, transfected Cos cells can reconstitute NF-AT DNA binding activity when mixed with Hela nuclear extract (FIG. 6 panel c, lanes 12–16) as do cytosolic extracts from T-cells (Flanagan et al. (1991) Nature 352: 803–807; Northrop et al. (1993) J. Biol. Chem. 268: 2917–2923). Antisera raised against bacterially expressed fragments of NF-AT$_c$ that have no similarity to NF-ATP are able to induce a supershift of the endogenous NF-AT complex, but not the AP-1 complex, from Jurkat cells or thymocytes (immune-1 and immune-2 respectively, FIG. 6 panel d). Immune-2 antisera reduced the DNA-protein complex produced using murine thymic nuclear extracts significantly, consistent with the relatively equal representation of NF-AT$_c$, and NF-AT$_p$ peptides in the purified protein from bovine thymus.

Example 6

NF-AT$_c$ Dominant Negative Mutant Assayed in Transient Transfection Assays

Figure 7:
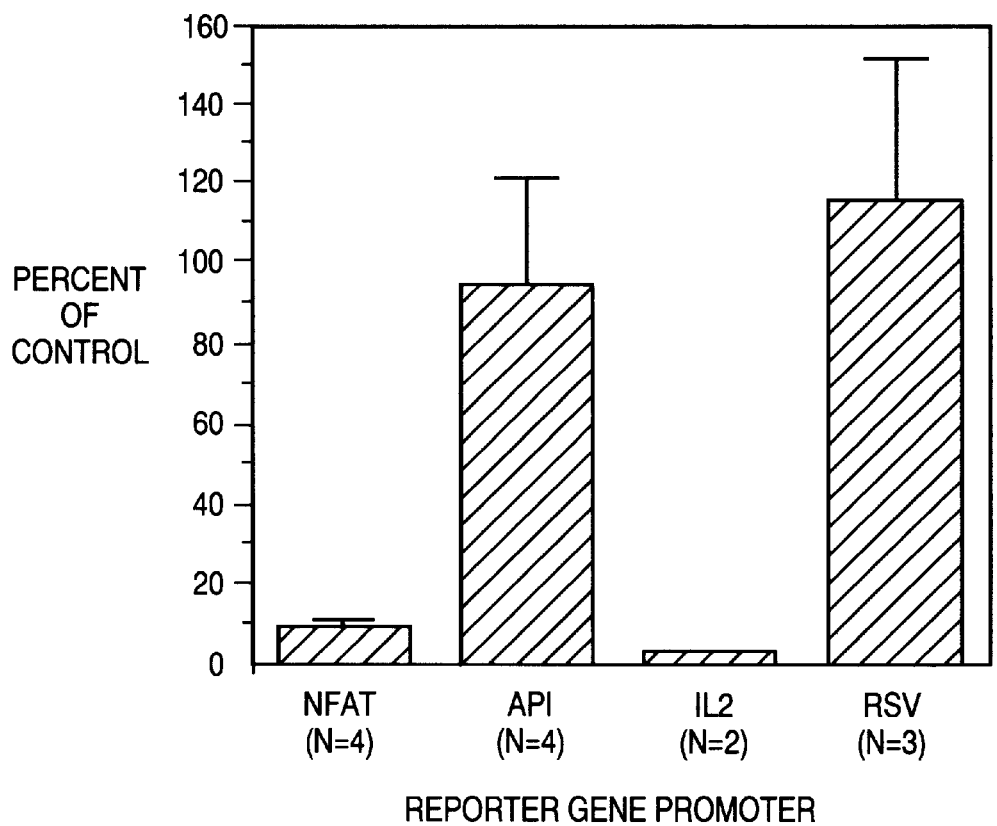
FIG. 7 shows dominant-negative NF-AT$_c$. Jurkat Tag cells were transfected with vector plasmid (control) or with the dominant negative NF-AT$_c$ plasmid, plus the indicated secreted alkaline phosphatase reporter plasmid. Transfected cells were transferred to fresh culture medium 24 hours after transfection and secreted alkaline phosphatase activity was measured (Clipstone and Crabtree (1992) Nature 357: 695–698) 16 to 24 hours later, after stimulation with 1 uM ionomycin plus 20 ng/ml PMA (NF-AT and IL-2 reporters), 20 ng/ml PMA alone (API reporter) or no stimulation (RSV reporter). Bars indicate, secreted alkaline phosphatase activity from cells transfected with the dominant negative NF-AT$_c$ as a percentage of the activity from cells transfected in parallel with control plasmid, and represent data obtained from (n) independent transfections. The dominant negative NF-AT$_c$ consists of a carboxy terminal truncation of the epitope tagged NF-AT$_c$ expression plasmid extending to the PvuI site at amino acid 463.

A dominant negative NF-AT$_c$, prepared after extensive deletion analysis of the cDNA, indicated that the amino terminal domain would block NF-AT-dependent function without affecting binding. This region of the cDNA is not found in NF-AT$_p$ and hence can be used to assess the contribution of NF-AT$_c$ to the activation of the IL-2 gene. The dominant negative NF-AT$_c$ used consists of a carboxy terminal truncation of the epitope tagged NF-AT$_c$ expression plasmid (supra) extending to the PvuII site at amino acid 463. Transfection of this dominant negative resulted in more than 90% inhibition of IL-2 promoter function as well as transcription directed by the NF-AT site (FIG. 7). This effect was highly specific since transcription directed by the AP-1 site or the RSV promoter and enhancer were relatively unaffected (FIG. 7). These results strongly indicate that NF-AT$_c$ contributes substantially to IL-2 gene expression in T cells.

Dominant-negative NF-AT$_c$ polypeptides or peptidomimetics thereof can be used as pharmaceutical antagonists of NF-AT-mediated activation of T cells. In one variation, such drugs can be used as commercial research reagents for laboratory testing and analysis of T cell activation and the like, among many other uses (e.g., immunosuppressant).

Example 7

Post-Translational Modification of NF-AT$_c$

Figure 8:
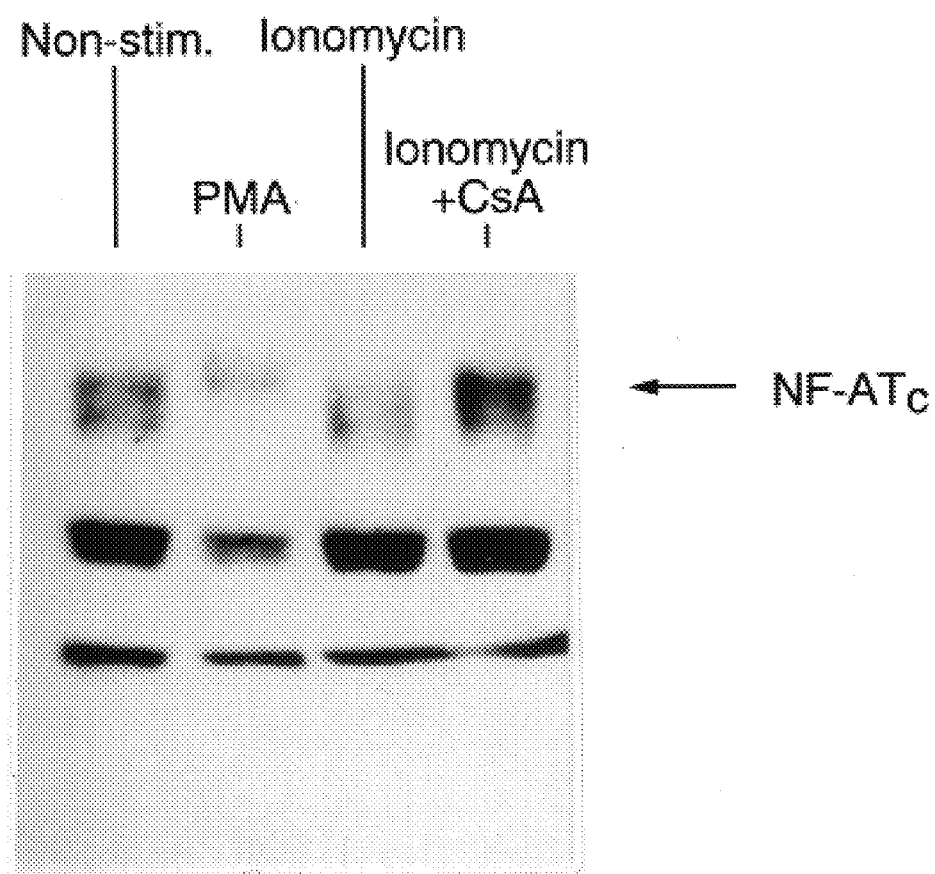
FIG. 8 shows changes in mobility of epitope tagged NF-AT$_c$ expressed in Jurkat cells. Cells were transfected with NF-AT$_c$ as in FIG. 2 and stimulated as shown for 2 hrs plus or minus 100 ng/mi CsA. Whole cell lysates were analyzed by western blotting as in FIG. 2.

Post-translational modification of NF-AT$_c$ was investigated in cells treated with agents that activate PKC or increase intracellular Ca++. Cells were transfected with NF-AT$_c$ as described in FIG. 2 and stimulated as shown for 2 hrs plus or minus 100 ng/ml CsA. Whole cell lysates were analyzed by western blotting as in FIG. 2. The bulk of NF-AT$_c$ in cells treated with ionomycin migrates faster than that in non-treated cells and this mobility shift is inhibited by CsA (FIG. 8, lanes 1, 3–4). This is consistent with a dephosphorylation event, possibly by direct action of calcineurin (Clipstone and Crabtree (1992) *Nature* 357: 695–697), however, any of a large number of processes could produce the observed mobility changes. There is evidence that NF-AT$_p$ is a substrate for calcineurin, however, the mobility shifts produced by phosphatase treatment of NF-AT$_p$ or NF-AT$_c$ are far greater than those observed in FIG. 8. These observations indicate that NF-AT$_c$ is not a direct substrate of calcineurin. PMA treatment produces a slower migrating NF-AT$_c$ (FIG. 8, lane 2); therefore, PKC-activated pathways likely contribute to NF-AT activity by modification of NF-AT$_c$ in addition to activation of the nuclear component.

Example 8

Calcineurin is the Rate-Limited for NF-ATc Nuclear Entry

Most tissues express one of the NF-AT family members. A variety of cell types, including lymphocytes and fibroblasts, support the Ca$^{2+}$-dependant nuclear localization of transfected as well as endogenous NF-ATc family members (Shibasaki et al., *Nature*, 382: 370–373). To develop an accurate assay for NF-AT translocation, NF-ATc was expressed in COS cells which, unlike lymphocytes, have abundant cytoplasm and hence allow easier assessment of cytoplasmic and nuclear localization.

COS-7 cells were maintained in Dulbecco's modified Eagle medium (DMEM; Sigma) with 10% fetal calf serum (FCS), 100 µg/ml of penicillin G. 100 µg/ml of streptomycin, and 10 mM HEPS (pH 7.4) at 37° C. in 5% CO$_2$. Cells were transfected by electroporation with 1 µg of SH160c Ho et al. (1995) *J. Biol. Chem.* 270: 19898, which encodes the FLAG epitope tag inserted at an XbaI site immediately 5' to the second codon of the human NF-ATc1 cDNA in the pBJ5 vector (*Nature*, 369:497–502)), plated on glass coverslips, and stimulated 18–14 hr post-transfection in fresh media or fresh media supplemented with ionomycin (2 µM final) plus 10 mM (final) CaCl2 for various amounts of time at 37° C. Ionomycin was obtained from Calbiochem and dissolved in DMSO. Cells were also treated with FK506 at 2 ng/ml plus ionomycin and CaCl2 or with ionomycin plus 2.5 mM EGTA for 60 min. FK506 was added at 2 ng/ml 15 min prior to addition of calcium and ionomycin. FK506 was obtained from Fukisawa (Chicago, Ill.) and dissolved in ethanol. Efficient nuclear translocation of NF-ATc in COS cells requires both ionomycin and the elevation of extracelluar calcium. The reason for this requirements for Ca$^{2+}$ may be that ionomycin stimulation of COS cells does not result in a intracellular Ca$^{2+}$ level as high as stimulated lymphocytes. Cells were then stained with the anti-FLAG antibody as follows. Cells adhering to coverslips were fixed in 4% paraformaldehyde and permeabilized in 0.1% Triton X-100. The FLAG epitope was detected by incubating with 1 µg/ml of anti-FLAG M2 antibody (Eastman Kodak Co.). The monoclonal antibody was detected by incubation with biotin-conjugated anti-mouse IgG (Caltag), followed by streptavidin-FITC and DAPI (Molecular Probes). Fluorescence was visualized with a Zeiss Axiophot fluorescence microscope. Fluorescent cells in which the nucleus and plasma membrane could be identified were scored as containing predominantly cytoplasmic staining, predominantly nuclear staining, or both cytoplasmic and nuclear staining. At least 100 cells were scored on each coverslip. Cells undergoing mitosis or with multiple nuclei were excluded. For all deletion constructs, the subcellular localization was confirmed using a confocal imaging fluorescence microscope.

Figure 9A:
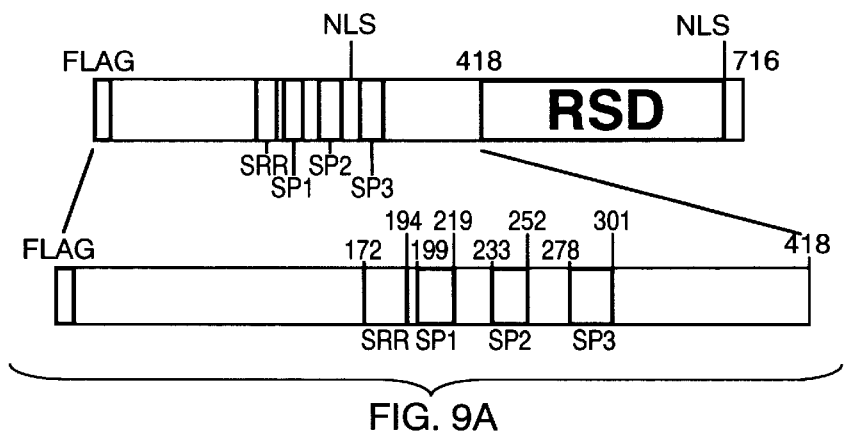
FIG. 9A is a diagram of a FLAG epitoped tagged NF-ATc1 protein indicating the respective positions in SEQ ID NO: 38 of the Rel Similarity Domain (RSD), two nuclear localization sequences (NLS), a conserved domain rich in serines (SRR), and three repeats rich is serines and prolines (SP1, SP2, SP3).
Figure 9B:
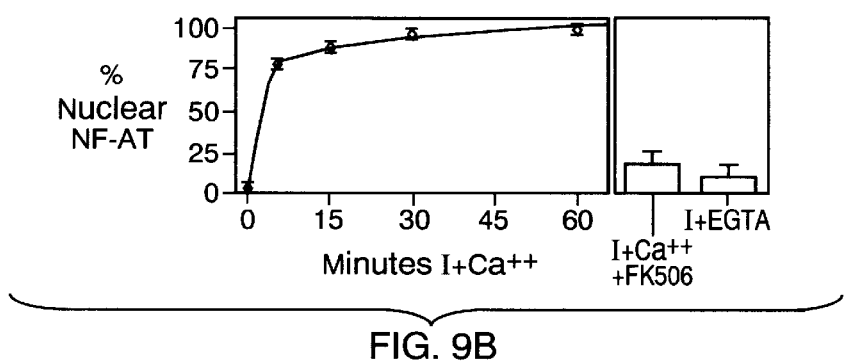
FIG. 9B is a diagram showing the percentage of Cos cells transiently transfected with NF-ATc1 (SH160c) expressing NF-ATc1 in the nucleus after various times of treatment of the cells with ionomycin and calcium (I+Ca++), or with FK506 plus (I+Ca$^{++}$+FK506) or with ionomycin plus 2.5 mM EGTA (I+EGTA) for 60 minutes.

As shown in the diagram in FIG. 9B, as with NF-ATc3(4) (Shibasaki et al., *Nature*, 382: 370–373), the amino terminus of NF-ATc1 was sufficient for Ca$^{2+}$-regulated nuclear import that was blocked by FK506. Furthermore, transfected NF-ATc1 moved into the nucleus within 5–15 min after ionomycin treatment.

Figure 9C:
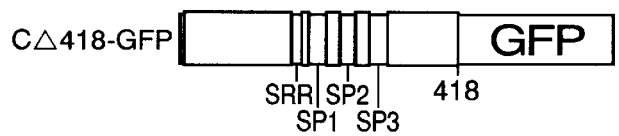
FIG. 9C is a diagram of the NF-AT fusion protein CΔ418-GFP, containing amino acids 1–418 of NF-ATc1 including the serine rich domain (SRR) and the three serine-proline rich domain (SP1, SP2, and SP3) fused to the green fluorescent protein (GFP).
Figure 9D:
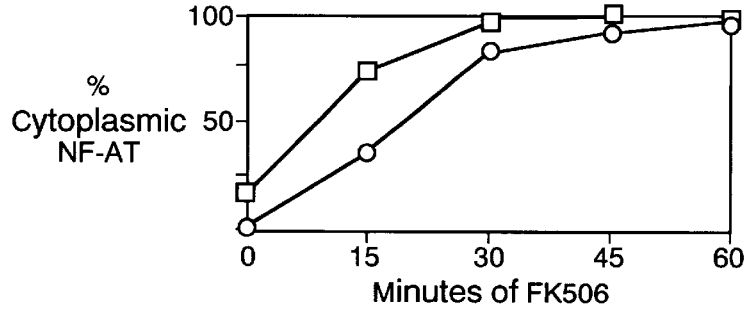
FIG. 9D shows the percentage of Cos cells transiently transfected with constructs encoding NF-ATc1 (□) or NF-AT(CΔ418)-GFP (○) having cytoplasmic NF-AT after one hour of stimulation with Ionomycin and calcium and then replacement of the medium with medium containing FK506. Cells expressing NF-ATc in the cytoplasm and those expressing NF-ATc in both cytoplasm and nucleus were added and divided by the total number of analyzed expressing cells.

Exit of NF-ATc from the nucleus was determined by stimulating transfected cells with I+Ca$^{++}$ for 1 hr and then replacing the medium with medium containing FK506. Slides were fixed at various time points, and the percentage of cells with cytoplasmic NF-ATc was determined. Cells expressing NF-ATc in the cytoplasm and those expressing NF-ATc in both cytoplasm and nucleus were added and divided by the total number of analyzed expressing cells. The results, which are shown in FIG. 9C indicate that NF-AT moved out of the nucleus and into the cytoplasm within 30 min of FK506 addition. These translocations occurred even if protein synthesis was inhibited. The full-length protein behaved similar to a fusion of the amino-terminal 418 amino acid with green fluorescent protein (NF-AT(CΔ418)-GFP) (FIG. 9A). pSH160cΔ41 8-GFP construct was made by fusing the BamHI-NotI fragment encoding GFP from pEGFP-1 (Clonetech) following the PvuII site at codon 418 of SH160c and was detected using its autofluorescence.

This time course of nuclear localization is consistent with that observed in murine lymphocytes activated by antigen presentation (Timmerman et al., *Nature*, 383: 837–840) and indicates that COS cells can support physiologic translocation of NF-ATc. As with NF-ATc3[4] (Shibasaki et al., *Nature*, 382: 370–373), overexpression of calcineurin enhanced the movement of NF-AT into the nucleus of COS cells (FIG. 9A), indicating that calcineurin is rate limiting for the movement of NF-ATc proteins into the nucleus.

Example 9

Addition of Heterologous Nuclear Localization Sequences to NF-ATc Results in Ca$^{2+}$-Independent, FK506-Resistant Nuclear Import The observation that overexpressed NF-ATc is cytoplasmic in Jurkat T lymphocytes and COS cells suggests that there is not an easily saturated cytoplasmic anchoring protein necessary to retain NF-ATc in the cytoplasm. Transfection of the NF-ATc1 expression construct over a 200-fold ranges of DNA concentration did not result in higher levels of constitutive nuclear localization. If NF-ATc was localized by a cytoplasmic anchoring partner, the addition of a fully active nuclear localization sequence (NLS) to NF-ATc should not overcome the cytoplasmic retention NF-ATc. Accordingly, NF-ATc1 expression constructs with zero, one, or two copies of either the SV40 large T-antigen NLS encoded between the FLAG epitope and the second amino acid of NF-ATc1, or one or two copies of a mutant form of the NLS (NLS-T). The constructs bearing the SV40 NLS and mutant (NLS-T) were created by insertion of synthetic oligo-nucleotides at the XbaI site of pSH160c (Ho et al. (1995). *J. Biol. Chem.* 270:19898, which encodes the FLAG epitope tag inserted at an XbaI site immediately 5' to the second codon of the human NF0ATc1 cDNA in the pBJ5 vector (Northrop et al. (1994) *Nature*, 369:497–502)). The inserted NLS is CTAGTCCTAAGAAGAAGAGAAAGG-TAT (SEQ ID NO: 80); the sequence of NLS-T is CTAGTC-CTAAGACGAAGAGAAAGGTAT (SEQ ID NO: 81) and substitutes a threonine for a lysine (*Cell*, 39:499–509) All point substitutions were created by sequential overlap extension PCR (*J. Biol. Chem.*, 270:19898–19900). Cells were then stained with an anti-FLAG antibody and the percentage of cells with nuclear fluorescence determined.

Figure 10:
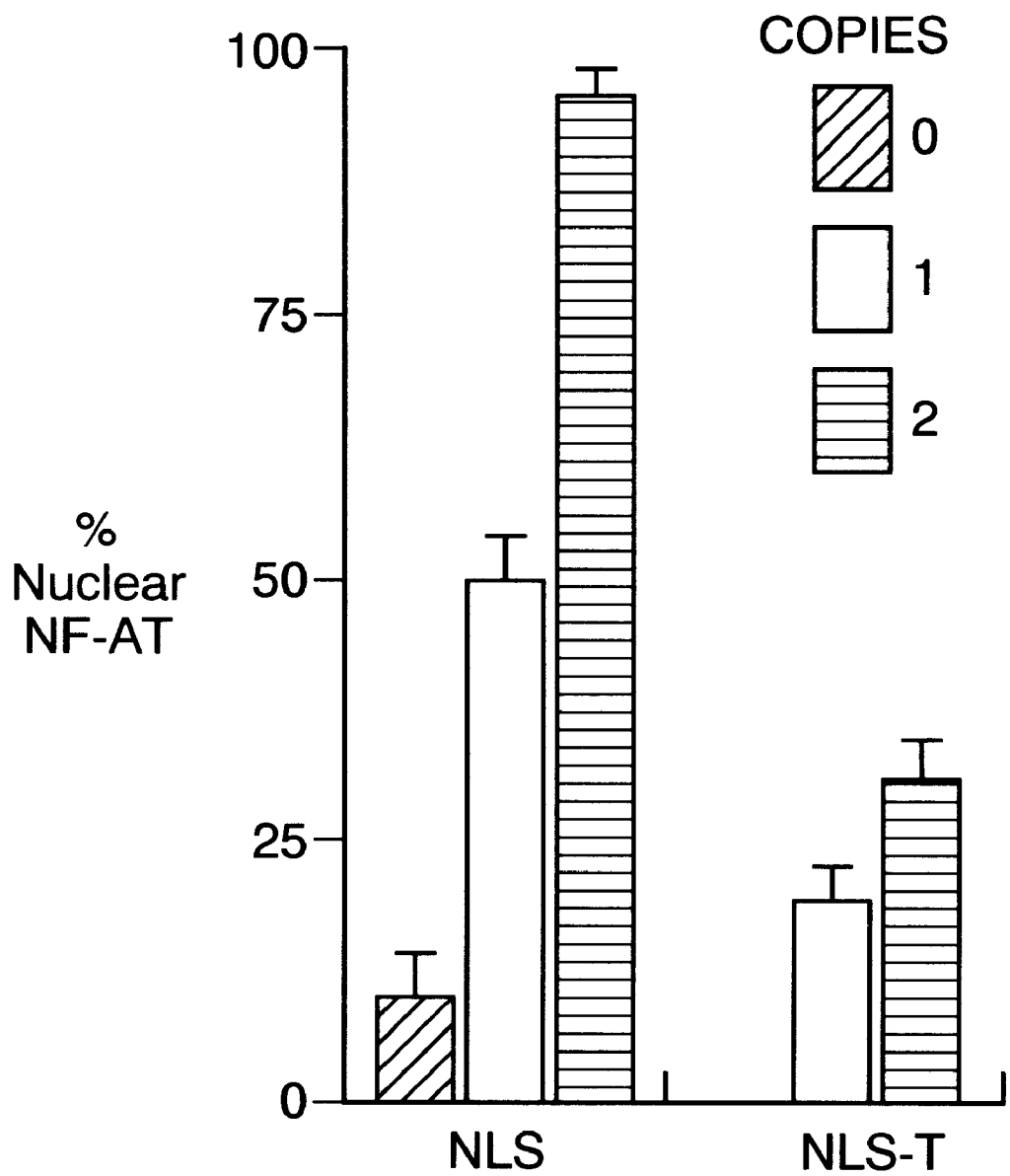
FIG. 10 depicts a diagram showing the percentage of Cos cells expressing NF-AT in the nuclear following transient transfection of the cells with a construct encoding NF-ATc1 fused to zero, one, or two copies of a wild-type NLS from SV40 large T antigen [NLS] inserted between the FLAG epitope and the second amino acid of NF-ATc1, or one or two copies of a mutant form of the NLS (NLS-T). Cells were stained with the anti-FLAG antibody.

As shown in FIG. 10, expression of NF-ATc1 with zero, one, or two copies of the SV40 large T-antigen NLS in COS cells results in a progressive increase in constitutive nuclear localization which was insensitive to FK506. In contrast, addition of the mutant NLS sequence, NLS-T (Kalderon et al. (1984) *Cell*, 39: 499–509), to NF-ATcI resulted in substantially less nuclear entry. The low level of nuclear localizations resulting from inclusion of NLS-T may be attributable to slight activity of this mutant, which, like the wild-type sequence, is enhanced when present in multiple copies (Roberts et al. (1987) *Cell*, 50: 465–475). These results argue against a mechanism of cytoplasmic localization dependent on a dominantly acting cytoplasmic binding protein.

Example 10

Two NLSs are Each Sufficient for NF-ATc Nuclear Translocation

Figures 11A, 11B:
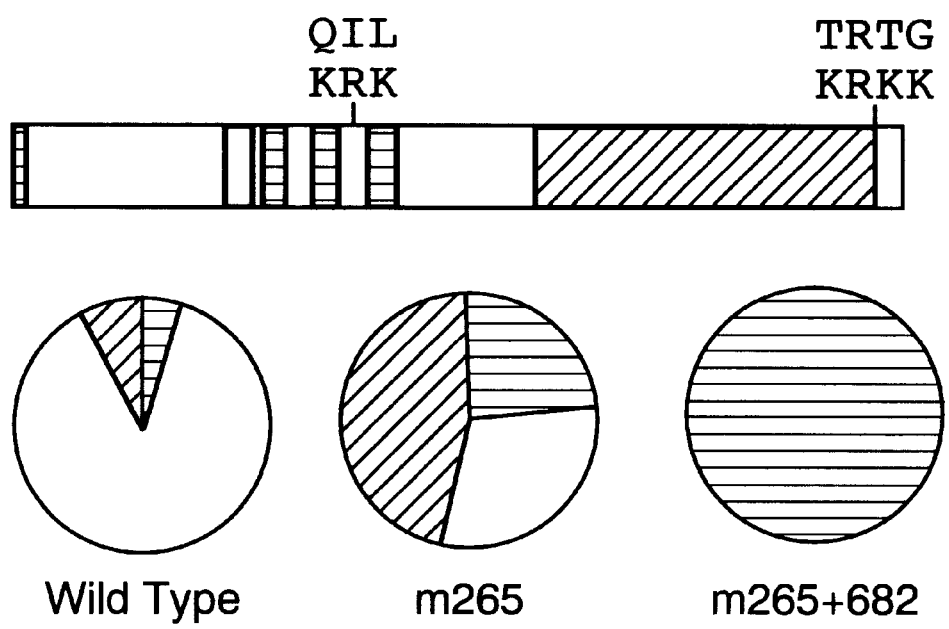
FIG. 11A shows the amino acid sequence of two conserved putative NLSs in NF-ATc1 (SEQ ID NO: 53 and SEQ ID NO: 54), and their positions in SEQ ID NO: 38.
FIG. 11B shows a diagram of NF-ATc1 and the amino acid sequence of the two NLSs, above which are shown the amino acid sequence of the mutated NLSs (TRTG has SEQ ID NO: 55 and KRKK has SEQ ID NO: 56). The lower portion of the figure shows the percentage of Cos cells expressing wildtype NF-AT or mutated NF-AT (m265, corresponding to an NF-ATc1 protein having a mutated N-terminal NLS; and m265+682 containing the m265 mutation and a mutation of the C-terminal NLS) in the nucleus after transient transfection of the cells and stimulation with ionomycin and calcium for 60 minutes. The percentage of cells staining in nucleus (lighted shaded areas), cytoplasm (solid areas), or both compartments (darkly shaded areas) was determined.

NF-ATc proteins contain four groups of clustered basic residues that are conserved among NF-ATc proteins which could possibly be NLSs (see FIG. 11A). To determine whether these sequences have NLS activity, each of them was linked individually to the cytoplasmic exchange factor SOS.

The SOS expression constructs were based on the human SOS cDNA tagged at the carboxyl terminus by a HA epitope, pSOS-E (*Proc. Natl. Acad. Sci.* 92:9810–9814). PSOS-265 was created by insertion of an oligonucleotides encoding the sequence LECNKRKYSLNVD (SEQ ID NO: 82) at the unique SalI site between SOS and the HA epitope. An expression construct encoding SOS (SOS-E) was expressed and visualized with 12CA5 antibody. Constructs encoding SOS-E attached to residues 263–271 of NF-ATc (SOS-265) or attached to residues 681–685 of NF-ATc (SOS-682) were also detected with the 12CA5 antibody. Immunoflucorescence was as described above, except that the HA epitope was detected by incubating with 1:2000 dilution of 12CA5 ascites.

The results, show that SOS-682, incorporating residues 682–685 of NF-ATc, and SOS-265, incorporating residues 265–267, are localized in the nucleus. Thus, these two conserved regions within NF-ATC are thus NLSs.

To determine whether these NLSs are required for nuclear import of NF-ATc, each sequence was mutated separately and in combination within the context of full-length NF-ATc1. A diagram of the mutations made in the NLS in the wild-type NF-ATc sequence is shown in FIG. 11B. The NLS at residues 265–268 was changed to QIL (construct m265). The NLS at residues 682–685 was changed to TRTG and the construct containing this mutation and m265 is referred to as m265+682. The mutant expression constructs were transfected in COS cells, and the cells were stimulated with I+$Ca^{++}$ for 60 minutes as described above. The percentage of cells staining in the nucleus, cytoplasm, or both compartments was determined.

The results, which are shown in FIG. 1B, indicate that mutation of the sequence at 265–267 from KRK to QIL reduced the extent of nuclear localization of NF-ATC in response to ionomycin, but up to 60% of cells show some $Ca^{2+}$-dependent nuclear accumulation of NF-ATC. Mutation of the sequence KRKK (SEQ ID NO: 56) at position 682–685 to TRTG (SEQ ID NO: 55), or precise removal of these 4 residues, had no effect on nuclear localization of NF-ATC in response to $Ca^{2+}$ elevation. However, NF-ATc containing mutations in both regions remains cytoplasmic after ionomycin treatment. Thus, like other nuclear proteins with multiple NLSs (Richardson et al. (1986) *Cell*, 44: 77–85), the two NLSs are partially redundant, as suggested by the observation that either can direct cytoplasmic SOS to the nucleus but both must be mutated to prevent nuclear entry. These data also indicated that both NLSs must be inactive in the absence of $Ca^{2+}$ stimulations.

Example 11

Mutation of Serines in the Amino Terminus Leads to Constitutive Nuclear Localization NF-ATc Since the amino terminus of NF-ATc is sufficient for calcineurin-dependent nuclear entry, it was determined whether phosphorylation of the amino terminus directed subcellular compartmentalization of the transcription factor. The amino terminus of each NF-ATc protein contains three copies of a sequence referred to as the SP-repeat motif (Ho et al. (1995). *J. Biol. Chem.*, 270: 19898–19900; Hoey et al. (1995) *Immunity*, 2: 461–472.; Masuda et al. (1995) *Mol. Cell Biol.*, 15:2697–2706). An additional SRR 23 amino acids in length lies just amino-terminal to the first SP repeat (Ho et al. (1995) *J. Biol. Chem.*, 270: 19898–19900) FIG. 9A). Phosphoamino acid analysis revealed that all phosphorylation is located on serines. Two-dimensional trypic peptide maps show many phosphopeptides derived from the amino-terminal 418 amino acids (see below). To determine whether phosphorylation of these particular serines could regulate NF-ATc localization, selected groups of conserved serines in the SRR and SP repeats were mutated to alanines and the subcellular localization of these mutants was determined in COS cells.

The SRR was mutagenized by changing the 11 serines to alanines in residues 172–194 to form mSRR. The first SP repeat was mutagenized by changing four serines to alanines in residues 199–211, to form mSP1. The second SP repeat was mutagenized by changing serines at 233 and 237 to alanines, mSP2. The third SP repeat was mutagenized at five serines at 278, 282, 286, 290, and 299, mSP3. Other mutated constructs are shown in FIG. 12. These substitutions were made in the construct pSH102cΔ418 (*Nature*, 369:497–502), which encodes the NF-AT carboxy terminal deletion construct (containing amino acid 1–418) and a hem-Agglutinin (HA) epitope tag at the amino terminus.

Immumoblot of cytoplasmic (C) or nuclear (N) extracts of cells transfected with wild-type (WT) or mutant forms of the NF-ATc cDNA were also done. Accordingly, transfected cells were treated for 60 min with media without additions (NS) or with ionomycin and calcium (I+CA$^{++}$), as described above, and then separated into cytoplasmic and nuclear fractions according to *J. Biol. Chem.* 270: 19898–19900, subjected to SDS-PAGE, transferred to a membrane and a Western blotting was performed using the M2 or 12CA5 antibody that was detected with anti-mouse peroxidase and chemiluminescence (Amersham).

The results indicate that mutation of all the serines within the SRR (mSRR) leads to constitutive nuclear localization in 100% of expressing cells that is unaffected by FK506. mSRR has an increased mobility on SDS electrophoresis, is present it the nucleus by Western blotting, and shows reduced incorporation of $^{32}$P after in vivo labeling with orthophosphate, consistent with the hypothesis that these serines affect the phosphorylation state of the protein in vivo. An NF-ATc mutant in which serines in the first SP repeat were substituted with alanines (mSP1) is also constitutively localized to the nucleus in 100% of expressing cells and shows a reduction in molecular weight. Similar results were obtained in NF-ATc mutants with S→A mutations in the first and third SP repeat (mSP13) and in versions in which mutations were engineered in all three SP repeats (mSP123) or combined with the mutations in the SRR (mSRR+SP123). The subcellular localization of each of these mutant forms of NF-ATc in constitutively nuclear if they are expressed in Jurkat cells, indicating that these phosphorserines control subcellular localization in a variety of cell types. The unregulated nuclear entry of the S→A mutations is not likely to be caused by denaturation of the protein, because each of these mutated forms of the mutated forms of NF-ATc participate in NF-ATc-dependent transcription.

Since S→A mutation of the SRR resulted in the smallest alteration in apparent molecular weight, it was likely that this region might contain the smallest numbers of critical phosphorserines necessary for cytoplasmic localization. These mutants can be dephosphorylated further after transfection into cells and ionomycin treatment, indicating that the SRR mutant is still a substrate for a phosphatase, possibly calcineurin. Thus further analysis by mutation of smaller blocks of serines in the SRR were performed. Alanine substitution at residues 172–176, 178–181, and 184–188, but not residues 191–194, resulted in nuclear accumulations of NF-ATc in 100% of expressing cells in the absence of Ca$^{2+}$/calcineurin signaling (see, FIG. 12A). Interestingly, the mutants with constitutive nuclear localization remain in the nucleus after adding FK506, a treatment that leads to rapid cytoplasmic accumulation of wild-type NF-ATc, NF-ATp, or NF-ATc3 that has been transported to the nucleus by stimulation (Flanagan et al. (1991) *Nature,* 352: 803–807; Shibazaki et al. (1996) *Nature,* 382: 370–372; Timmerman et al.(1996) *Nature,* 383: 837–840. Thus, these results indicates that phosphorylation of these residues is necessary for export of NF-ATc from the nucleus.

Example 12

Calcineurin Dephosphorylates Serines in NF-AT

To determine whether calcineurin could be the phosphatase directing nuclear entry, the ability of calcineurin to specifically dephosphorylate the residues associated with nuclear entry was investigated.

NF-AT GST fusion proteins were prepared as follows. Residues 196–304 of NF-ATc1 (Northrop et al. (1994) *Nature,* 369:497–502) were cloned into the Snial site of pGEX-3x to generate pGSP. A GST fusion protein in which the S→A substitutions in all three SP repeats described above was similarly constructed, pGAP, with 9 S and 10 T residues remaining. The GST fusion proteins were phosphorylated by incubating 1 μg of fusion protein immobilized on glutathione-Sepharose with whole brain extract (55 μg protein) (prepared as described below) and with 100 μm ATP and [γ-$^{32}$P]ATP (400 μCi/μmole) in 50 μl of kinase buffer (20 mM Tris at pH 7.5, 10 mM MgCl$_2$, 1 mM DTT) for 30 min. at 30° C. Kinase reactions were teminated by washing the agarose beads three times in 1 ml of calcineurin buffer. The fusion proteins were then incubated with calcineurin as above, or treated with 2 units of shrimp alkaline phosphatase (U.S. Biochemical) or 5 units of protein phosphatase 1 (Boehringer Mannheim) in the buffer described by the manufacturer for 30 min at 30° C. Samples were then electrophoresed and exposed for autoradiograpy.

Figures 12A, 12B:
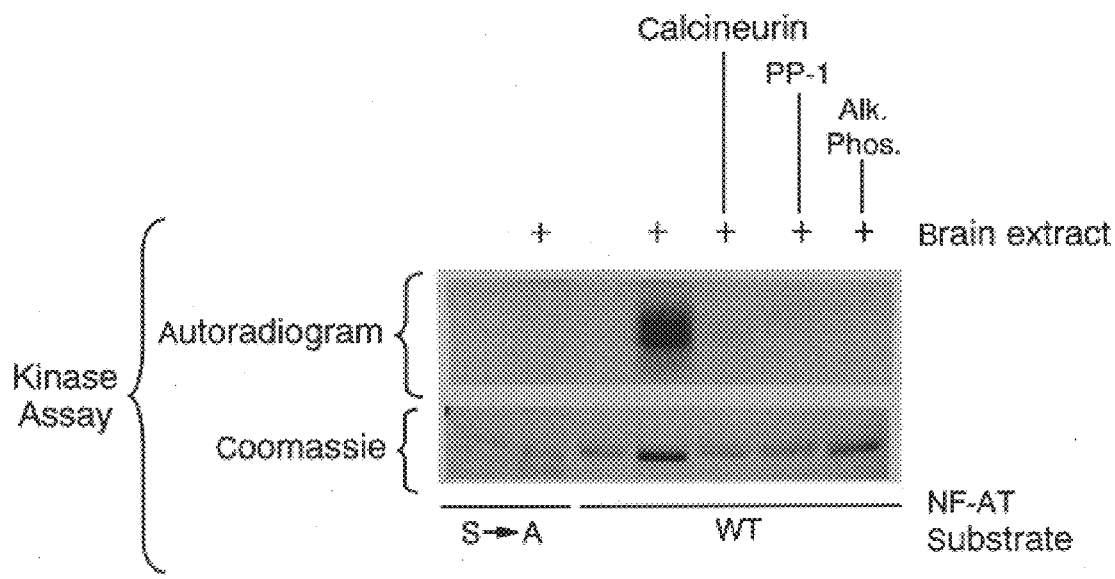
FIG. 12A shows the amino acid sequence of the SRR from NF-ATc1 (amino acid 170 to 194 of SEQ ID NO: 38, set forth in SEQ ID NO: 57), and the cellular localization of NF-ATc1 proteins (nuclear (N) or cytoplasmic (C)) having the indicated serine to alanine substitutions (SEQ ID NOs: 58–63).
FIG. 12B is a photograph of a Western blot, showing phosphorylated GST-NF-ATc1 fusion proteins containing amino acids 196–304 of NF-ATc (WT) or with serine to alanine mutations in the three SP repeats (S→A), after having been phosphorylated by incubation with [γ-$^{32}$P]ATP and a partially purified preparation of cellular NF-AT kinase activity (brain extract) and then incubated with phosphatases as indicated, prior to separation by electrophoresis and autoradiography (top lane). The bottom lane indicates the amount of NF-AT in each sample, as visualized by Coomassie staining.

The results, which are presented in FIG. 12B, indicate, that once phosphorylated, the 196–304 WT substrate is readily dephosphorylated by itt vitro treatment with calcineurin and phosphatase 1, which is activated by calcineurin (Cohen (1989) Annual Rev. Biochem. 58:453). These results indicate that the conserved serines in the SP repeats that control nuclear localization of NF-ATc are substrates for cellular kinases and calcineurin. Glycogen synthase kinase-3 (GSK-3) is a highly conserved proline-directed serine-threonine kinase that phosphorylates NF-AT in vivo and opposes Ca$^{2+}$/calcineurin-induced nuclear entry, see below. GSK-3 phosphorylates the conserved serines in the SP repeats in vitro. The serines in the SRR and SP repeat motifs conform to a GSK-3 consensus substrate sequence (Fiol et al. (1994) *J. Biol. Chem.,* 269: 32187–32197). Taken together, these results indicate that the conserved serines in these two motifs are phosphorylated in vivo by cellular kinases and dephosphorylated by calcineurin.

Example 13

Phosphoserines in the SRR Control an Intramolecular Interaction Within NF-ATc

The results described above raise the possibility that both basic NLSs interact with phosphoserines on the SP repeats and the serine-rich region to prevent nuclear entry in the unstimulated state. Such intramolecular interactions are difficult to discern because of the difficulty of expressing separate parts of the same protein at concentrations that would be equivalent to the high effective concentration of residues on the same peptide chain. The overcome this barrier to detecting intramolecular interactions, one part of NF-ATc was immobilized and interactions with other regions expressed in extracts of COS cells, which phosphorylate and translocate NF-ATc under Ca$^{2+}$/calcineurin control were analyzed.

Extracts of COS cells that had been transfected with the empty expression vector or a vector encoding the HA epitope-tagged amino-terminal 418 residues of NF-ATc (2–418) (Northrop (1994) *Nature,* 369:497–502) were incubated with glutathione-agarose beads coupled to GST or incubated with beads coupled to a GST fusion with the RSD of NF-ATc (GST-RSD). A GST fusion protein consisting of the Rel domain of NFATc1, GST-RSD (residues 415–716), was expressed in bacteria and affinity purified on glutathione-agarose ((*Gene,* 67:31–40). Residues 1–418 of NF-ATc1 tagged at the amino terminus with the HA epitope (*Nature,* 369:497–502) were expressed in COS cells and an extract made by lysis in buffer A (*J. Biol. Chem.* 270: 19898–19900) with protease and phosphatase inhibitors. One hundred micrograms of this extract was incubated with 30 μl of glutathione-agarose coupled to GST, GST-RSD, or GST-mNLS (~2 μg of fusion protein) in 300 μl of incubation buffer (50 mM HEPES at pH 7.8, 150 mM NaCL, 1 mM EDTA, 50 mm NaPO$_4$, 0.5% NP-40) with protease and phosphatase inhibitors as in (*J. Biol. Chem.*270 19898–19900) for 2 hr. at 4° C. and washed three times in incubation buffer. Affinity-selected proteins were eluted from the washed beads with SDS sample buffer and detected by immunoblotting using either the 7A6 (*Nature,* 369:497–502) or 12CA5 monoclonal antibodies.

Figure 13A:
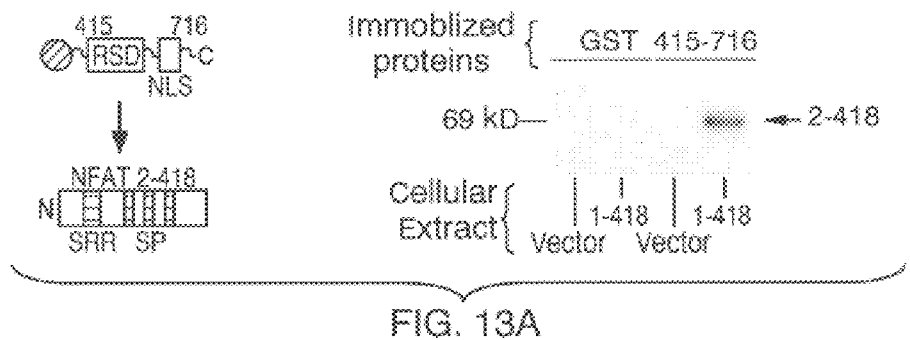
FIG. 13A is a photograph of a Western blot showing the results of an affinity purification of extracts of COS cells that had been transfected with the empty expression vector (Vector) or a vector encoding the HA epitope-tagged amino-terminal 418 residues of NF-ATc (2–418) with glutathione-agarose beads coupled to GST or incubated with beads coupled to a GST fusion with the RSD of NF-ATc (GST-RSD). Affinity-selected proteins were detected by immonoblotting with the anti-HA 12CA5 antibody. The left part of the panel is a graphic representation of the NF-AT polypeptide that was attached to the agarose beads and the NF-AT polypeptide which was affinity purified on the beads.

As shown in FIG. 13A, when the carboxyl terminus of the protein containing the Rel similarity domain and one of the two partially redundant NLSs was immobilized (GST 415–716), it interacted readily and specifically with the amino-terminal half of NT-ATc1 (1–418) when expressed in COS cell extracts, as well as interacting with the endogenous protein in extracts from lymphocytes.

Figure 13B:
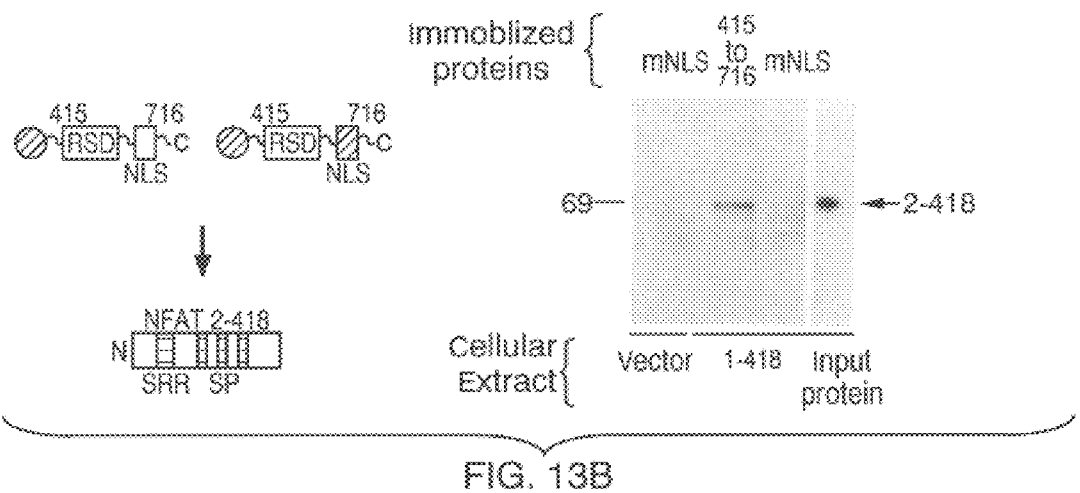
FIG. 13B is a photograph of a Western blot showing the results of an affinity purification of extracts from COS cells transfected with a construct encoding the HA epitope-tagged amino-terminal 418 residues of NF-ATc (2–418) or vector alone (Vector), with GST-RSD or a version with a mutation in the carboxy-terminal NLS (mNLS). Bound proteins were detected with the 12CA5 antibody. The left part of the panel is a graphic representation of the NF-AT polypeptides used in the example.

Because the amino terminus, which contains multiple phosphoserines, might simply interact with basic residues in the Rel similarity region, the NLS in the rel similarity domain was mutated and the binding of this mutated protein to amino-terminal residues 1–418 was analyzed. As shown in FIG. 13B, mutation of the carboxy-terminal NLS from KRKK (SEQ ID NO: 56) to TRTG (SEQ ID NO: 55) abolished binding to the amino-terminal 418 residues.

Figure 13C:
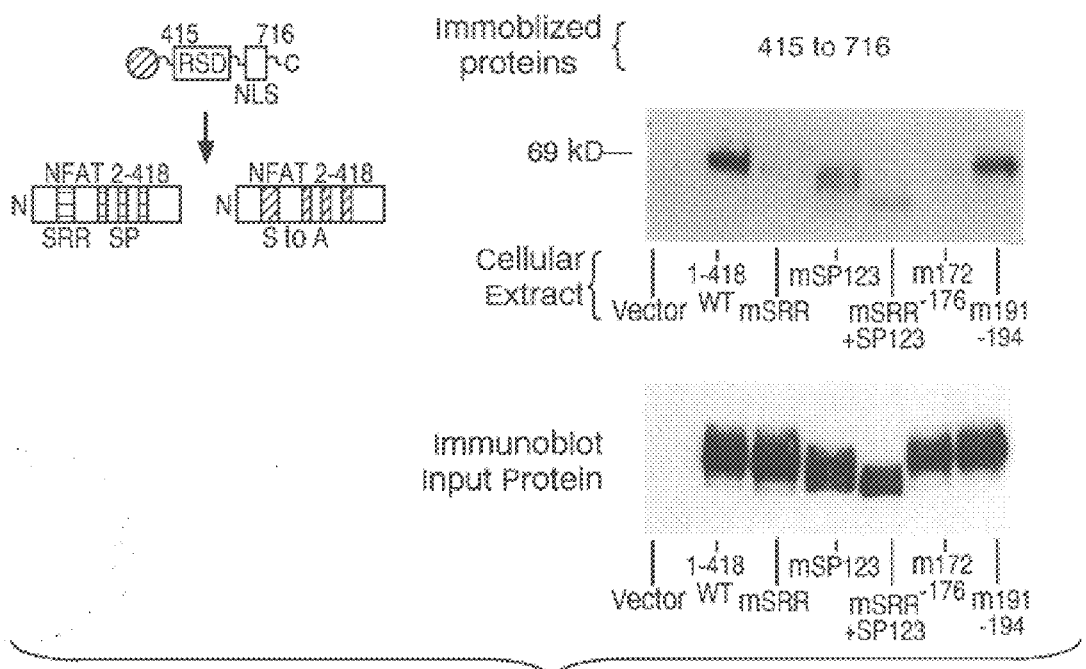
FIG. 13C is a photograph of a Western blot showing the results of an affinity purification of extracts from COS cells that had been transfected with the HA epitone-tagged amino-terminal 418 residues of NF-ATc (1–418 WT) or versions in which S→A mutations were present in the SRR or SP repeats with GST-RSD. The associated proteins were detected with the 7A6 antibody. The lower part of the blot shows the amount of NF-AT present in the cell extracts prior to affinity purification.

This mutation is unlikely to result in denaturation because alteration of this NLS still permits cooperation with NF-ATn and NF-AT-dependent transcription in vivo. To demonstrate that this interaction is sensitive to the presence of phosphoserines in the amino terminus, extracts of COS cells that had been transfected with the HA epitope-tagged amino-terminal 418 residues of NF-ATc (1–418 WT) or versions in which S→A mutations were present in the SRR or SP repeats were incubated with GST-RSD and then washed. As shown in FIG. 13C, the amino-terminal 418 residues with S→A mutation in the SRR shows reduced association with the carboxyl terminus of the protein, whereas S→A changes in the three SP repeats affect this association less strongly. Each set of mutations results in more rapid migration on SDS electrophoresis, indicating that these S→A mutations prevent phosphorylation. Nonoverlapping S→A mutations within the SRR (FIG. 13C) were also tested in this intramolecular association assay. Alanine substitutions in residues 172–176 reduce the association with the rel similarity domain (RSD), whereas alanine substitutions in serines between 191 and 194 do not alter the association with the RSD. Interestingly, there is a correlation between binding to the RSD in the intramolecular association assay and Ca$^{2+}$/calcineurin-independent nuclear entry—ml72–176 is constitutively nuclear and ml191–194 undergoes regulated nuclear entry. The differences in the in vitro intramolecular association assay between each S→A mutations of NF-ATc are unlikely to be attributable to denaturation, as all mutants are immunoprecipitated by a monoclonal antibody to the region of NF-ATc in the SP repeats (Northrop et al. (1994) *Nature,* 369:497–502), are stable when expressed in cells, and direct NF-AT-dependent transcription. The binding activity is unlikely to indicate a head-to-tail dimer forming between full-length NF-ATc molecules, as the protein is a monomer in solution and when bound to DNA (Hoey et al. (1995) *Immunity,* 2:461–472).

Figure 14:
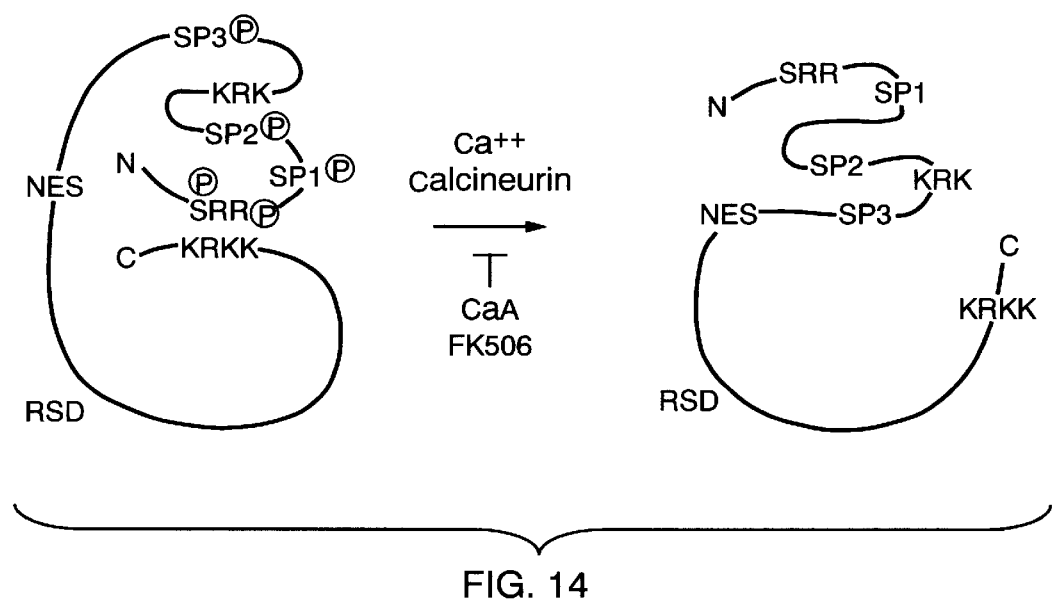
FIG. 14 shows a model of the mechanism of NT-ATc nuclear entry. According to the model, cytoplasmic NF-ATc is phosphorylated on the SP repeats and SRR masking the activity of its two partially redundant NLSs, the sequence KRK at position 265–267, and the sequence KRKK/R at position 682–685 of NF-ATc1. Dephosphorylation in response to activation of calcineurin leads to an alteration in an intramolecular interaction and perhaps a conformational change, exposing one or more of the NLSs to the nuclear import machinery. Once in the nucleus, termination of calcium signaling results in rapid export to the cytosol, possibly by the exposure of nuclear export sequences (NES).

Thus, the interaction within NF-ATc is dependent on residues in the SRR as well as an intact carboxy-terminal NLS. The correlation between the subcellular localization of mutants in the SRR and their behavior in in vitro binding assays suggests that this intramolecular association controls exposure and function of the carboxy-terminal NLS. The S→A changes in the three SP repeats disturbs binding to the RSD only weakly and suggests that these phosphoserines may not participate as strongly in the interaction with the carboxyl terminus of the protein. The dephosphorylation of the SP repeat motifs may result in nuclear localization by another mechanism, perhaps by exposure of the other NLS that lies between the second and third SP repeats. A model representing the interaction between the NLS and phosphoryated residues in NF-AT is presented in FIG. 14. This model is likely to be extended to the other members of the NF-ATc gene family based on the conservation of the NLSs, the SRR, and the SP repeat regions. The amino terminus of NF-ATc3 and NF-ATp (*Proc. Natl. Acad. Sci.,* 93:8907–8912; *Nature,* 382:370–373) undergo Ca$^{2+}$-sensitive nuclear entry.

Example 14

NF-AT Kinase Activity Copurifies With GSK-3

This example demonstrates that the kinase activity that phosphorylates the N-terminus of NF-AT copurifies with GSK-3.

Protein extracts from rat brains were tested for NF-AT kinase activity as follows. Extracts were prepared from rat brains homogenized in 2 volumes of 20 mM tris (pH 7.5), 1 mM EDTA, 5 mM EGTA, 2 mM dithiothreitol (DTT), and 50 mM β-glycerol-phosphate with protease and phospatase inhibitors [0.1 mM Na$_3$VO$_4$, 1 mM phenylmethylsulfonyl fluoride, pepstatin (1 μg/ml), aprotinin (1 μg/ml), leupeptin (5 μg/ml), and 1 mM benzamidine]. A portion of the 80,000 g supernatant was passed over a G-50 sizing column to remove endogenous adenosine triphosphate (ATP), made 10% in glycerol, and used a whole brain extract (5.5 mg of protein per ml). The NF-AT kinase activity was followed through NH$_4$SO$_4$ fractionation and separation on phosphocellulose (P-11 resin), and elution with 200 mM NaCl. The active fractions were pooled and further purified on a Mono-S column (Hughes et al., *Eur. J. Biochem.* 203, 305 (1991)).

Column fractions were assayed for NF-AT kinase activity on wild type and mutated NF-AT peptides with [γ-$^{32}$P]ATP and then autoradiographed. Furthermore, since analysis of NF-AT N-terminal portion, in particular amino acids 196–304, indicated the presence of putative overlapping GSK-3 consensus sites (SSXXS(P)) (see FIG. 15), column fractions were also assayed for the phosphorylation of GS-2, the GSK-3-specific peptide substrate (Welsh et al., *J. Biol. Chem.* 271, 11410 (1996)). In addition, since GSK-3 (Hughes et al., *Eur. J. Biochem.* 203, 305 (1991)) often phosphorylates serines adjacent to serines previously phosphorylated by protein kinase A (PKA) or another kinase (Fiol et al., *J. Biol. Chem.* 269, 32187 (1994)), phosphorylation of PKA-prephosphorylated wild type NF-AT peptide was also used as a substrate. Phosphorylation of several sites in NF-ATc by PKA could produce a series of phosphorylation-dependent, overlapping GSK-3 consensus sites (Fiol et al., *J. Biol. Chem.* 269, 32187 (1994)) (FIG. 15). The total amount of protein in each fraction was also determined (as measured by absorbance at 280 nm).

The substrate NF-AT peptides were prepared by cloning a DNA fragment encoding residues 196 to 304 of NF-ATc1

(Durand et al., *Mol. Cell. Biol.* 8, 1715 (1988); Cocerill et al., ibid 15, 2071 (1995); Chuvpilo et al., *Nucleic Acids Res.* 21, 5694 (1993); Rooney et al., *Immunity*, 2, 473 (1995); Goldfield et al., *J. Exp. Med.* 178, 1365 (1993)) into pGEX-3x to generate pGSP. A GST fusion protein with S→A substitutions (FIG. 15), pGAP, was similarly constructed with 9 serine and 10 threonine residues remaining. Bacterially expressed proteins were purified on gluthathione agarose and used at 1 µg of fusion protein per 10 µl of bead slurry (D. B. Smith and K. S. Johnson, *Gene* 67, 31 (1988)). The fusion proteins were used directly or were prephosphorylated on agarose by addition of 5 units of PKA (Sigma) per microgram of fusion protein at 30° C. in kinase buffer [20 mM tris (pH 7.5), 10 mM $MgCl_2$, and 1 mM DTT] with 1 mM ATP for 2 hours and then washed to remove PKA and ATP. One unit of PKA is defined as 1 pmol of $^{32}P$ transferred per minute. Kinase assays incubated fusion protein (1 µg) on glutathione Sepharose, 100 µM ATP with $[\gamma-^{32}P]ATP$ (400 µCi/µmol) in 50 µl of kinase buffer for 30 min at 30° C. Beads were incubated with 10 µl of column fractions or of whole brain extract (55 µg of protein), 2.5 units of purified PKA or GSK-3β (New England Biolabs), or both. Experiments with crude or partially purified brain extracts included aprotinin, leupeptin, and pepstatin (all at 1 µg/ml), 0.1 mM β-glycerol-phosphate, and 1 mM $Na_3VO_4$. Kinase reactions were terminated by washing the agarose beads twice with I ml of TEN [50 mM tris (pH 7.5), 1 mM EDTA, 150 mM NaCl, and 0.5% NP-40] to remove phosphorylated cellular proteins, fractionated on SDS-PAGE, autoradiographed, and stained with Coomassie to ensure that the substrate was not degraded.

Figure 15A:
FIG. 15A shows the amino acid sequence of amino acids 196–304 of NF-ATc1 (SEQ ID NO: 38) set forth in SEQ ID NO: 64. Putative overlapping GSK-3 consensus sites (SEQ ID NO:85) [SPXXS(P)] (Fiol el al., *J. Biol. Chem.* 269, 32187 (1994)) are overlined. The nuclear localization sequence is in bold type, and sites phosphorylated by PKA in vitro are boxed. The underlined serines are serines that have been substituted with alanines in some examples.
Figure 15B:
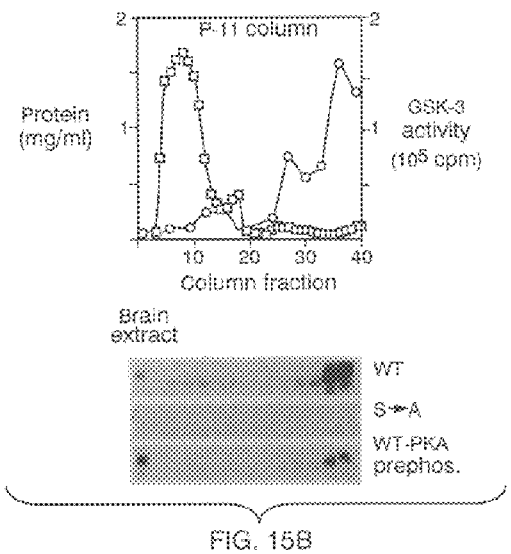
FIG. 15B shows a graph depicting the level of GSK-3 activity in various fractions eluted from a P-11 column following ammonium sulfate fractionation of brain extracts. The lower part of the panel shows autoradiograms of Western blots showing the ability of the eluted fractions to phosphorylate GST-NF-AT fusion proteins containing wild-type (WT) NF-ATc1 or NF-ATc1 in which the underlined serines of pane A were mutated into alanines, or NF-ATc1 which was in vitro phosphorylated with PKA (WT-PKA prephosph.).
Figure 15C:
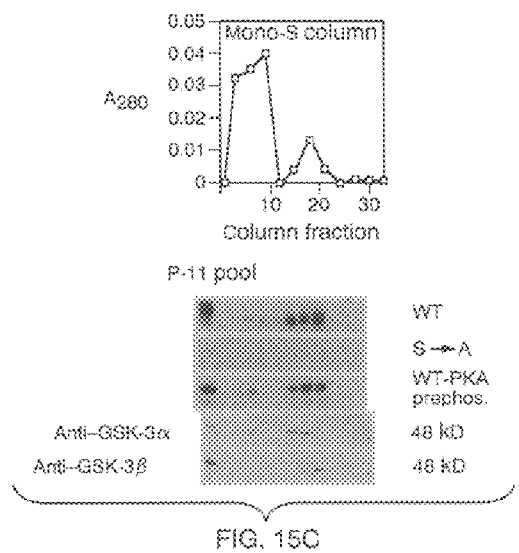
FIG. 15C shows a graph depicting the amount of protein in various fractions eluted from a Mono-S column of the P-11 pool of panel B. The lower part of the panel shows autoradiograms of Western blots showing the ability of the eluted fractions to phosphorylate GST-NF-AT fusion proteins containing wild-type (WT) NF-ATc1 or NF-ATc1 in which the underlined serines of pane A were mutated into alanines, or NF-ATc1 which was in vitro phosphorylated with PKA (WT-PKA prephosph.). The bottom two photographs show autoradiograms of Western blots containing protein from the eluted fractions incubated with antisera specific for GSK-3α and GSK-3β.

The result of the kinase assays using fractions from the column, which are represented in FIG. 15 (panels A and B), show that the chromatographic behavior of the NF-AT kinase was similar to that of GSK-3. In particular, NF-AT kinase activity was shown to be strongest in about fractions 35–40 of column P-11 (see FIG. 15B) and about fractions 15–25 of Mono-S column (see FIG. 15C), which are also the fractions which had strongest GSK-3 activity. In fact, the peak of NF-AT kinase activity and GSK-3 immunoreactivity is at fraction 21. Furthermore, the PKA prephosphorylated wild-type NF-AT peptide was also phosphorylated by the same column fractions. On the contrary, the active column fractions did not significantly phosphorylate the mutated NF-AT substrate peptide.

Protein immunoblotting, with antibodies to GSK-3α and GSK-3, confirmed that they copurified with the NF-AT kinase (FIG. 15C), and PKA eluted in a partially overlapping peak from the Mono-S column. In fact, the peak of PKA immunoreactivity is at fraction 24. Thus, these results indicate that NF-ATc is likely be a substrate of GSK-3 and PKA.

Example 15

GSK-3 and Another Kinase Synergize to Phosphorylate NF-AT

The role of GSK-3 in the phosphorylation of NF-ATc was assessed by immunodepleting GSK-3 from whole brain extracts. Antisera to GSK-3α and GSK-3β or control antibodies were used to remove these proteins from whole brain extract. Immunodepletion of GSK-3 activity in 110 µg of whole grain extract was done in 200 µl of TEN, 1 mM DTT, and protease and phosphatase inhibitors (same as used above) with 3 µg of anti-GSK-3α (sheep polyclonal, Upstate Biotechnolgy), anti-GSK-3β (immunoglobulin Gl (IgGl) monoclonal, Transduction Labs), or both, and 20 µl of protein G-Sepharose at 4° C. for 4 hours. The IgGl mouse monoclonal antibody (mAb) M2 (Kodak), sheep polyclonal anti-HIVp 17 (NIH), or both were used as control antibodies. The NF-AT kinase assay used 2.5 µl of the supermatant (1.2 µg of protein) (Cook et al., *EMBO, J.* 15, 4526 (1996); Stambolic et al. *Curr. Biol.* 6, 1664 (1996)).

Immunodepleted extracts were incubated with PKA-prephosphorylated NF-AT in an in vitro kinase reaction with $[\gamma-^{32}P]ATP$, and the $^{32}P$-labeled substrate was detected by autoradiography. Two substrates were used: NF-AT (WT) to detect the priming kinase activity, and WT-PKA prephosphorylated to detect GSK-3 activity. In one reaction, five units of purified GSK-3β were added to the reaction.

Figure 16A:
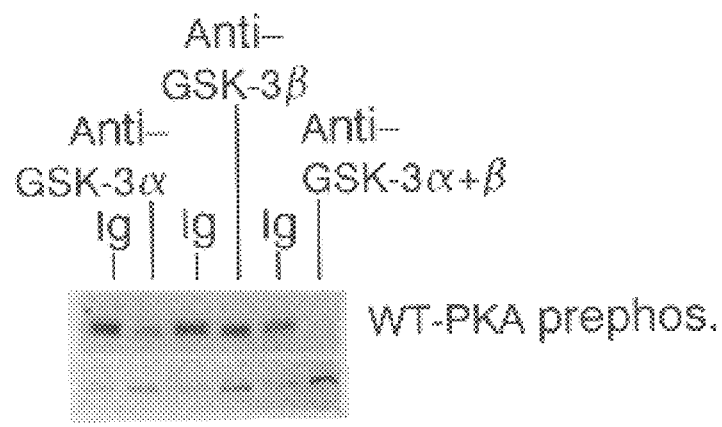
FIG. 16A shows an autoradiogram of a Western blot of PKA-prephosphorylated NF-AT (WT-PKA prephos.) incubated with brain extracts immunodepleted with antisera to GSK-3α and/or GSK-3β or control antibodies in an in vitro kinase reaction with $[\gamma\text{-}^{32}P]ATP$, and the $^{32}P$-labeled substrate (upper gel; the lower gel shows Coomassie staining).
Figure 16B:
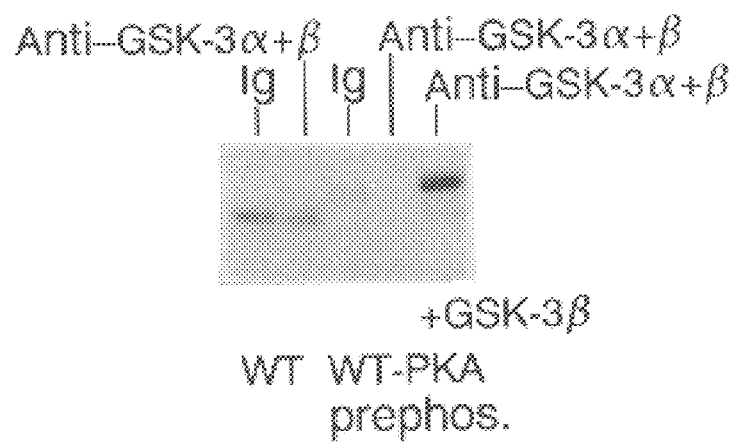
FIG. 16B shows a photograph of an autoradiogram of a Westen blot of PKA-prephosphorylated NF-AT (WT-PKA prephos.) or NF-AT (WT) incubated with brain extracts immunodepleted with antisera to GSK-3α and GSK-3β or control antibodies (Ig) in an in vitro kinase reaction with $[\gamma\text{-}^{32}P]ATP$.

As shown in FIG. 16, depletion of GSK-3α and GSK-3β from the extracts with specific antibodies completely and specifically removed the NF-AT kinase activity toward NF-ATc prephosphorylated by PKA. However, this immunodepleted extract maintained the ability to phosphorylate NF-ATc (FIG. 16B), which indicated that there are at least two NF-AT kinase activities: an activity that can act directly on NF-ATc, and a second activity that requires prior phosphorylation of NF-ATc. The second kinase activity is that of GSK-3 (as shown by immunodepletion experiments) and the priming kinase activity can be provided itt vitro by PKA. However, specific inhibition of PKA in extracts indicates that PKA does not provide all of the priming kinase activity in either brain or lymphocyte extracts. It should be noted, that GSK-3 immunodepletion does not effect the phosphorylation of the unprimed NF-AT substrate because under conditions of substrate excess, only a small percentage of substrate become primed and hence available for subsequent phosphorylation by GSK-3. It is likely that enzyme is limiting in these assays because there is no detectable alteration of the mobility of the substrate upon Coomassie staining, which would reflect phosphorylation.

Example 16

PKA and GSK-3 Stoichiometrically Phosphorylate NF-ATc

The wild-type NF-AT fusion protein (referred to as "WT substrate") was phosphorylated in vitro with purified PKA and/or GSK-3 kinases. In the reactions in which the WT substrate was incubated with the two kinases, the first kinase was permitted to phosphorylate the WT substrate with nonradioactive ATP to completion; then, the WT substrate beads were washed to remove the kinase and the WT beads were phosphorylated by the second kinase in the presence of $[\gamma-^{32}P]ATP$.

Figure 17A:
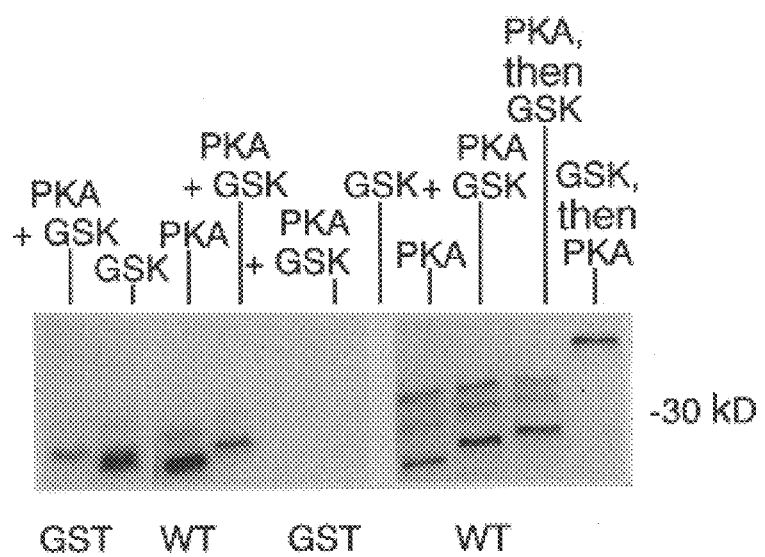
FIG. 17A shows autoradiograms of a Western blot depicting NF-AT-GST fusion proteins phosphorylated in vitro with the indicated purified kinases. In the rightmost lanes, the first kinase was permitted to phosphorylate the WT substrate with nonradioactive ATP to completion; then, the WT substrate beads were washed to remove the kinase and the WT beads were phosphorylated by the second kinase in the presence of $[\gamma\text{-}^{32}P]ATP$.

The results, which are shown in FIG. 17A, indicate that phosphorylation of GSK-3β alone incorporated <0.01 mol of $^{32}P$ per mole of NF-AT, whereas PKA alone gave 1 to 2 mol of $^{32}P$ per mole of NF-AT and the combination of GSK-3β and PKA gave 3 to 7 mol of $^{32}P$ per mole of NF-AT. Casein kinase II (CKII) and $Ca^{2+}$-calmodulin-dependent protein kinase II (CaMkII) did not stoichiometrically phosphorylate the glutathione-S-transferase fusion protein NF-AT-GST. Furthermore, GSK-3β phosphorylated NF-ATc only if it was first phosphorylated by PKA. Similar results were obtained using dephosphorylated NF-ATc purified from lymphocytes as a substrate.

It was then tested whether PKA and GSK-3β contribute to the celullar phosphorylation of NF-ATc by comparing the tryptic phosphopeptides from NF-ATc phosphorylated in vivo with those derived from in vitro phosphorylation of the NF-AT fusion protein. NF-ATc was overexpressed in COS cells (which support reversible Ca2+-dependent nuclear localization) and labeled with [$^{32}$P]orthophosphate. COS cells transfected with 3 µg of PSH102 (Northrop et al., Nature 369, 497 (1994)) were labeled with [$^{32}$P] orthophosphate (1 mCi/ml) for 6 hours and immunoprecipitated with the hemagglutinin (HA) mAb 12CA5, transferred to polyvinylidene difluoride membrane, and digested with trypsin. Oxidized peptides (1000 cpm) were separated by electrophoresis on cellulose at pH 1.9 for 30 min at 1000 V and then chromatographed in the second dimension using butanol-acetic acid-pyridine solvent (Boyle et al., Methods Enzymol. 201, 110 (1991)). In one reaction, the PKA+GSK-3β in vitro phosphorylated peptides were mixed with the in vivo phosphorylated peptides before two-dimensional separation to establish that they are similar.

Figure 17B:
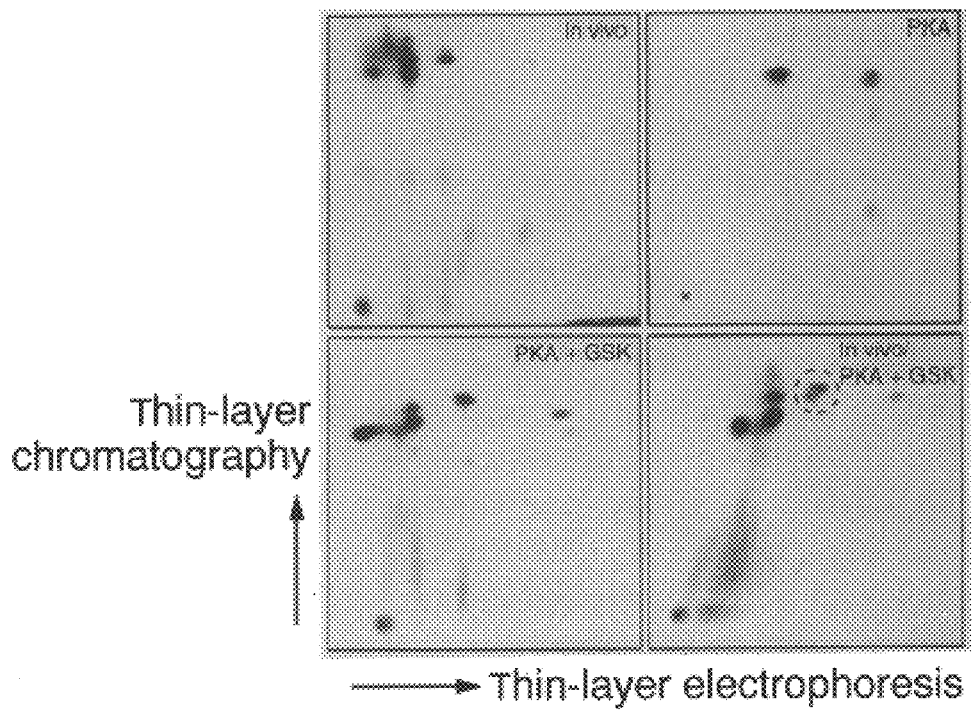
FIG. 17B depicts autoradiograms of two-dimensional tryptic phosphopeptide maps of the NF-ATc1 wild-type fusion protein with the indicated kinases in vitro. NF-ATc was overexpressed in COS cells [which support reversible Ca2+-dependent nuclear localization] and labeled with $[^{32}P]$ orthophosphate. In the lower right panel, the PKA+GSK-3β in vitro phosphorylated peptides were mixed with the in vivo phosphorylated peptides before two-dimensional separation to establish that they are similar. Phosphopeptides migrating differently are circled with a dashed line.

The results, shown in FIG. 17B, indicate that the tryptic phosphopeptides from NF-ATc phosphorylated in vivo with those derived from in vitro phosphorylation of the NF-AT fusion protein were identical, with the exception of one phosphopeptide. These results suggest that GSK-3β and another kinase synergize to phosphorylate NF-AT on the sites involved in Ca$^{2+}$-dependent nuclear localization in vivo.

Example 17

Sites of Phosphorylation of NF-T by PKA and GSK-3

The sites of phosphorylation by GSK-3 and PKA were defined by Edman degradation of in vitro $^{32}$P-labeled tryptic fragments. Wild-type NF-ATc-GST fusion protein was phosphorylated in vitro with PKA with [γ-$^{32}$P]ATP(50 µCi/µmol) and cleaved with Factor Xa to release the fusion protein. This was isolated on SDS-polyacrylamide gel electrophoresis (PAGE) and cleaved by trypsin, and radioactive fragments were purified by high-performance liquid chromatography (HPLC). One radioactive fraction release $^{32}$P in the second Edman degradation cycle and had the sequence ASVTEESWLGAR (SEQ ID NO: 83) of the tryptic peptide with Ser$^{245}$ in the second position. A second radioactive fraction released $^{32}$P in the third Edman degradation cycle and had a molecular size indicating the tryptic peptide KYSLNGR encompassing Ser$^{269}$ in the NF-ATc sequence. A second GST fusion protein encoding residues 223 to 277 of NF-AT was purified, phosphorylated in vitro with non-radioactive ATP and PKA, washed, then phosphorylated with [γ-$^{32}$P]ATP (50 µCi/µmol) and GSK-3β. The fusion protein was isolated on SDS-PAGE and cleaved by trypsin, and two radioactive fragments were purified by HPLC. One radioactive fragment contained the tryptic peptide GLGACTLLGSPQHSPSTSPR (SEQ ID NO: 84).

Thus, the results indicate that PKA phosphorylates the NF-ATc fusion protein at two serines (FIG. 15A). The PKA site at Ser$^{245}$ creates a series of overlapping GSK-3 substrate sites. Phosphorylation of the PKA-prephosphorylated NF-ATc fusion protein by GSK-3β labeled the peptide that contains this array of GSK-3 sites (FIG. 15A).

Example 18

GSK-3 Overexpression Blocked Ca++ NF-AT Induced Nuclear Translocation

The biological importance of NF-ATc phosphorylation by GSK-3β was assessed by manipulating its activity in cells and determining the effect on the subcellular localization of NF-ATc. Cos cells, which like many cells, express GSK-3 (Woodgett, in Methods in Enzymology, T. Hunter and B. M. Sefton, Eds. (Academic Press, San Diego, Calif., 199 1), vol. 200, p. 564), were cotransfected with 1 µg of a construct encoding FLAG epitope-tagged NF-ATc1 and 3 µg of GSK-3 expression vector or with the empty vector and the cells were left .unstimulated or were treated with 2 µM ionomycin and 10 mM CaCl$_2$ (I+Ca$^{2+}$) to induce nuclear localization of NF-ATc. Human GSK-3β cDNA (He et al., Nature 374, 617 (1995))was cloned into pBJ-5. NF-ATc was visualized with FLAG mAb M2 and indirect immunofluorescence. COS cell NF-AT translocation assay were done as described in Northrop et al., Nature 369, 497 (1994).

The results show that transfected NF-ATc family members (Shibasaki et al. Nature 382, 370 (1996); Luo et al., Proc. Natl. Acad. Sci. U.S.A. 93, 8907 (1996)), like endogenous NF-ATc, were cytoplasmic and translocated to the nucleus when cells were stimulated by agents that increase intracellular Ca$^{2+}$. Furthermore, overexpression of GSK-3β blocked the Ca$^{2+}$-calcineurin-induced nuclear translocation of coexpressed NF-ATc in COS cells.

Figure 18A:
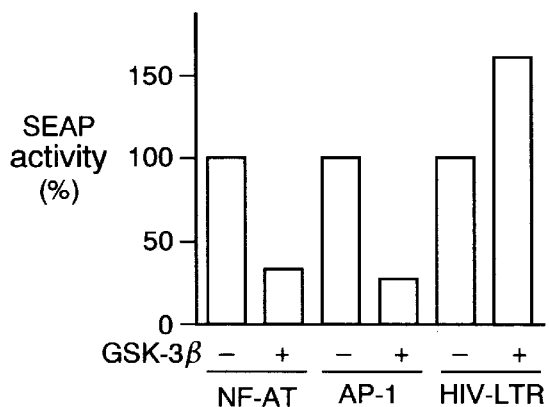
FIG. 18A shows the activiy of alkaline phosphatase (SEAP) in extracts from Jurkat cells transfected with an SEAP reporter gene under the control of an NF-AT, AP-1 or HIV-LTR regulatory element and in which GSK-3β is overexpressed or in which the empty vector was overexpressed. NF-AT SEAP activity is expressed as a percentage of the ionomycin-stimulated and phorbal 12-myristate 13-acetate (PMA)-stimulated control activity; AP-1 and HIV-LTR SEAP activities are expressed as a percentage of PMA-stimulated activity (Spencer et al., *Science* 262, 1019 (1993)).

In another example, endogenous NF-AT-dependent transcription was shown to be inhibited by overexpression of GSK-3β. Jurkat-T antigen cells were transfected with 2 µg of a transcription reporter plasmid (NF-AT dependent reporter, AP-1 dependent reporter, or HIV-LTR containing reporter linked to a gene encoding the SEAP) and either 3 µg of the GSK-3β expression construct or empty vector. NF-AT SEAP activity was measured and expressed as a percentage of the ionomycin-stimulated and phorbol 12-myristate 13-acetate (PMA)-stimulated control activity; AP-1 and HIV-LTR SEAP activities are expressed as a percentage of PMA-stimulated activity (Spencer et al., Science 262, 1019 (1993)). The results, which are depicted in FIG. 18, panel A, show that GSK-3 overexpression inhibits NF-AT dependent reporter gene expression. AP-1 dependent reporter gene expression was also downregulated by GSK-3 overexpression, probably due to the ability of GSK-3 to produce an inhibitory phosphorylation on c-Jun (Mikolakaki et al., Oncogene 8, 833 (1993)). GSK-3 did not have an inhibitory effect on the HIV-LTR dependent reporter gene expression.

In yet another example, the ability of various serine-threonine kinases to inhibit the nuclear entry of cotransfected NF-ATc in COS cells was compared. Accordingly, COS cells were contransfected with I ug of FLAG epitope-tagged NF-ATc1 and 1 µg of the serine-threonine kinases CKII, CaMkδA, CaMkδB, PKA or PKC or 3 µg of GSK-3p or 0.5 µg of ERK. ERK cDNA was cloned into pBJ-5. Drosophilia CKII cDNA was polymerase chain reaction-amplified and cloned into pBJ-5. Murine PKA cDNA and an activated form of PKC-β were cloned into pSRα. The calcineurin A and B expression constructs (Clipstone and Crabtree, Nature 357, 695 (1992)), CaMkII constructs (Srinivasan et al. J. Cell Biol. 126, 839 (1994)), COS cell NF-AT translocation assay, and Jurkat T antigen cell transcription reporter assays (Northrop et al. (1994) Nature 369:497) were as described. Transfected cells were stimulated with ionomycin and 10 mM Ca$^{2+}$, and the percentages of cells expressing NF-AT localized in the nucleus, cytoplasm, or both compartments were scored visually and are presented as a percentage of expressing cells. The transfected ERK kinase was activated by adding PMA (25 ng/ml). Comparison of the relative expression of the HA epitope-tagged kinases was performed by immunoblotting 15 µg of whole cell extracts with HA mAb 12CA5.

Figure 18B:
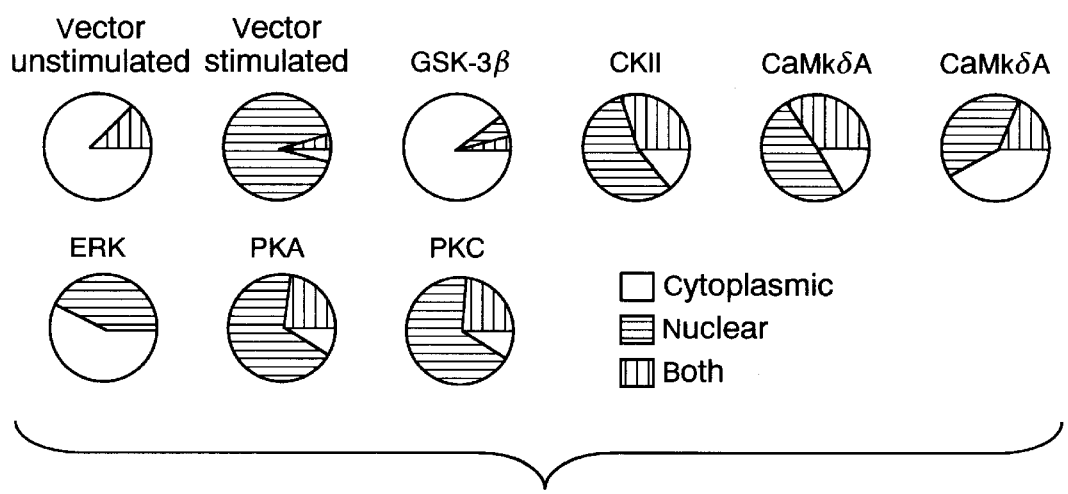
FIG. 18B shows the percentage of cells expressing NF-ATc1 in the cytoplasm, nucleus or both after cotransfection of COS cells with FLAG epitope-tagged NF-ATc1 and each of the indicated serine-threonine kinases. Cells were stimulated with ionomycin and 10 mM $Ca^{2+}$, and the percentages of cells expressing NF-AT localized in the nucleus, cytoplasm, or both compartments were scored visually and are presented as a percentage of expressing cells. The transfected ERK kinase was activated by adding PMA (25 ng/ml).

The results, which are presented in FIG. 18B, indicate that although GSK-3 was expressed in smaller amounts, it was the most active in inhibiting nuclear entry of NF-ATc.

Overexpression of PKA had little effect on NF-ATc localization. This may indicate that endogenous PKA activity or another kinase is adequate to phosphorylate NF-ATc in COS cells or that such phosphorylation is necessary, but not sufficient, for nuclear export. Thus, these results indicate that the $Ca^{2+}$-calcineurin signaling pathway is opposed by GSK-3.

Example 19

Overexpression of GSK-3 Enhances the Nuclear Export of NF-AT

This example describes the effects of GSK-3 on the nuclear export of NF-AT by first causing its translocation to the nucleus by stimulating cells with ionomycin, then removing the $Ca^{2+}$-calcineurin signal and blocking further nuclear import with the calcineurin inhibitor FK506 (Clipstone and G. R. Crabtree, Nature 357, 695 (1992)).

COS cells were cotransfected with expression constructs encoding FLAG epitope-tagged NF-ATc1 (1 μg), calcineurin A and B (0.5 μg each) (N. A. Clipstone and G. R. Crabtree, Nature 357, 695 (1992)), and 2 μg of vector, GSK-3β or GSK-KM, a catalytically inactive GSK-3β (He et al., Nature. 374, 617 (1995)). Cells were also cotransfected with a version of NF-ATc1 in which the underlined serines in FIG. 15A were changed to alanines with calcineurin and GSK-3β. The inclusion of Ca-calcineurin promotes NF-ATc nuclear entry (Shibasaki et al., Nature 382, 370 (1996); Luo et al., Proc. Natl. Acad. Sci. U.S.A. 93, 8907 (1996)) and overcomes the cytoplasmic localization of NF-ATc induced by GSK-3β overexpression. Wild-type NF-ATc was localized in the cytosol in 98% of unstimulated expressing cells, whereas 90% of cells translocated NF-ATc to the nucleus with I+$Ca^{2+}$, treatment; this translocation was completely blocked by FK506. NF-ATc was localized in the nucleus by treatment with I+$Ca^{2+}$ for 60 min, then the medium was changed to medium with FK506 (20 ng/ml) to terminate $Ca^{2+}$ signaling and to block nuclear reentry of NF-ATc. Transfected NF-ATc was detected with FLAG mAb M2 by indirect immunofluorescence, and 200 expressing cells were scored as expressing NF-ATc in the cytoplasm, nucleus, or both compartments.

Figure 19:
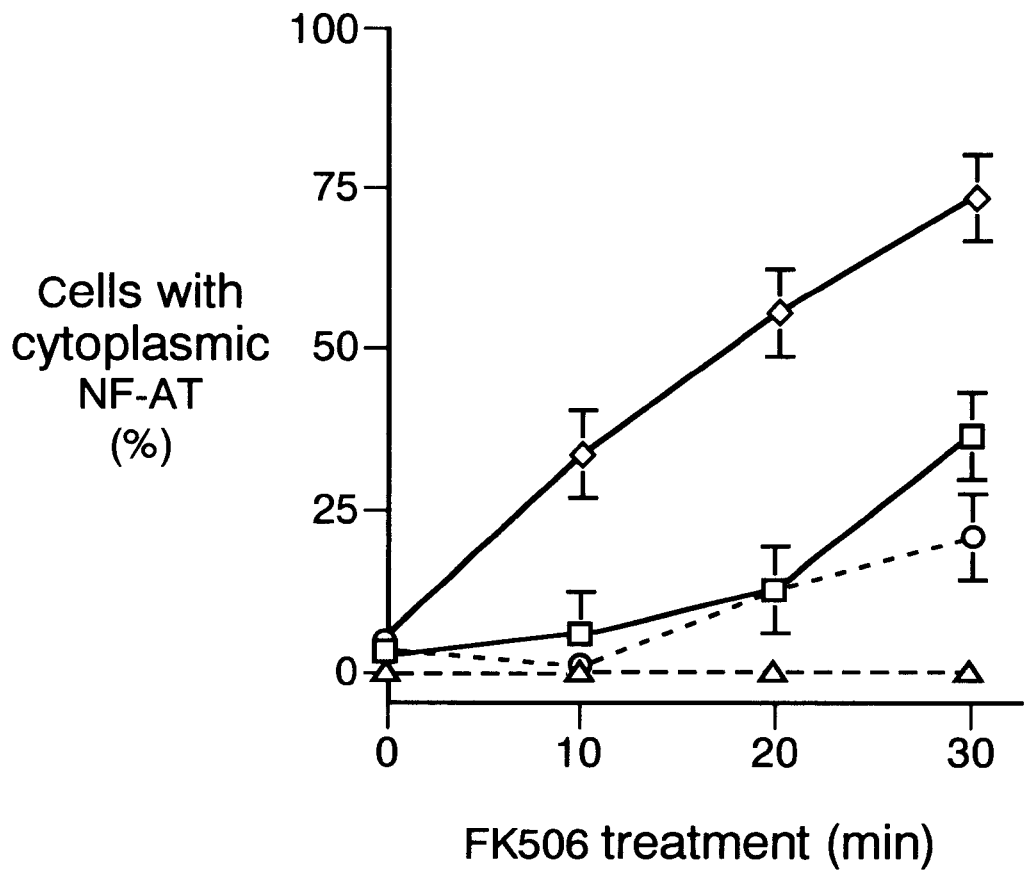
FIG. 19 shows the percentage of cells having cytoplasmic NF-ATc, after overexpression of GSK-3β in COS cells cotransfected with expression constructs encoding FLAG epitope-tagged NF-ATc1, calcineurin A and B, and vector (□), GSK-3β(◇) or GSK-KM (○), a catalytically inactive GSK-3β (He et al., *Nature.* 374, 617 (1995)). Cells were also cotransfected with a version of NF-ATc1 in which the underlined serines in FIG. 1A were changed to alanines with calcineurn and GSK-3β (Δ). To obtain NF-ATc localization in the nucleus, the transfected cells were treated with ionomyin and $Ca^{2+}$ for 60 min, then the medium was changed to medium with FK506 (20 ng/ml) to terminate $Ca^{2+}$ signaling and to block nuclear reentry of NF-ATc. Transfected NF-ATc was detected with FLAG mAb M2 by indirect immunofluorescence, and 200 expressing cells were scored as expressing NF-ATc in the cytoplasm, nucleus, or both compartments.

The results, shown in FIG. 19, show that overexpression of GSK-3β in amounts approximately one-tenth those of NF-ATc enhanced the movement of NF-ATc into the cytoplasm relative to that in cells transfected with the vector or with a catalytically inactive form of GSK-3β (He et al., Nature, 374, 617 (1995)). GSK-3p overexpression did not influence the constitutive nuclear localization of NF-ATc with S-A mutations in the serine-proline repeats. These data indicate that GSK-3β acts catalytically to direct the nuclear export of NF-ATc and that the regulation of nuclear export involves the phosphorylation of NF-ATc at conserved serines. Because NF-ATc family members are expressed in many tissues and have sequence similarity at the $NH_2$-terminal residues involved in nuclear import and export, GSK-3 is likely to control the compartmentalization of each of the four different NF-ATc family members.

EQUIVALENTS

Those skilled in the art will recognize, or be able to ascertain using no more than routine experimentation, many equivalents of the specific embodiments of the invention described herein. Such equivalents are intended to be encompassed by the following claims.

SEQUENCE LISTING (1) GENERAL INFORMATION:

(iii) NUMBER OF SEQUENCES: 85

(2) INFORMATION FOR SEQ ID NO:1:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(xi) SEQUENCE DESCRIPTION: SEQ ID NO:1:

TTCCTCCGGG GCGCGCGGCG TGAGCCCGGG GCGAGG    36

(2) INFORMATION FOR SEQ ID NO:2:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(xi) SEQUENCE DESCRIPTION: SEQ ID NO:2:

CAGCGCGGGG CGGCCACTTC TCCTGTGCCT CCGCCCGCTG CT                                42

(2) INFORMATION FOR SEQ ID NO:3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:3:

GCCGCGCGGA TGCCAAGCAC CAGCTTTCCA GTCCCTTCCA AG                                42

(2) INFORMATION FOR SEQ ID NO:4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:4:

CCAACGTCAG CCCCGCCCTG CCGCTCCCCA CGGCGCACTC CA                                42

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:5:

TTCAGACCTC CACACCGGGC ATCATCCCGC CGGCGG                                       36

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:6:

GCCACACCAG GCCTGATGGG GCCCCTGCCC TGGAGAGTCC TC                                42

(2) INFORMATION FOR SEQ ID NO:7:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:7:

AGTCTGCCCA GCCTGGAGGC CTACAGAGAC CCCTCGTGCC TG                42

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:8:

GTGTCTCCCA AGACCACGGA CCCCGAGGAG GGCTTTCCC                   39

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:9:

AGCTGGCTGG GTGCCCGCTC CTCCAGACCC GCGTCCCCTT GC                42

(2) INFORMATION FOR SEQ ID NO:10:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:10:

TACAGCCTCA ACGGCCGGCA GCCGCCCTAC TCACCCCACC AC                42

(2) INFORMATION FOR SEQ ID NO:11:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:11:

GACCACCGAC AGCAGCCTGG ACCTGGGAGA TGGCGTCCCT GT                42

(2) INFORMATION FOR SEQ ID NO:12:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:12:

CCTGGGCAGC CCCCCGCCCC CGGCCGACTT CGCGCCCGAA GA                               42

(2) INFORMATION FOR SEQ ID NO:13:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:13:

GCTCCCCTAC CAGTGGCGAA GCCCAAGCCC CTGTCCCCTA CG                               42

(2) INFORMATION FOR SEQ ID NO:14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:14:

CTTCGGATTG AGGTGCAGCC CAAGTCCCAC CACCGAGCCC AC                               42

(2) INFORMATION FOR SEQ ID NO:15:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:15:

CATGGCTACT TGGAGAATGA GCCGCTGATG CTGCAGCTTT TC                               42

(2) INFORMATION FOR SEQ ID NO:16:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:16:

AAGACCGTGT CCACCACCAG CCACGAGGCT ATCCTCTCCA AC                               42

(2) INFORMATION FOR SEQ ID NO:17:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "oligonucleotide"

(xi) SEQUENCE DESCRIPTION: SEQ ID NO:17:

TCAGCTCAGG AGCTGCCTCT GGTGGAGAAG CAGAGCACGG AC                     42

(2) INFORMATION FOR SEQ ID NO:18:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:18:

AACGCCATCT TTCTAACCGT AAGCCGTGAA CATGAGCGCG                        40

(2) INFORMATION FOR SEQ ID NO:19:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:19:

AGAAACGACG TCGCCGTAAA GCAGCGTGGC GTGTGGCA                          38

(2) INFORMATION FOR SEQ ID NO:20:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:20:

GCATACTCAG ATAGTCACGG TTATTTTGCT TCTTGCGAAT G                      41

(2) INFORMATION FOR SEQ ID NO:21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:21:

AGGGCGCGGG CACCGGGGCG CGGGCAGGGC TCGGAG                            36

(2) INFORMATION FOR SEQ ID NO:22:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:22:

GCAAGAAGCA AAATAACCGT GACTATCTGA GTATGC                             36

(2) INFORMATION FOR SEQ ID NO:23:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

Ser Pro Arg Ala Ser Val Thr Glu Glu Ser Trp Leu Gly
1               5                   10

(2) INFORMATION FOR SEQ ID NO:24:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Ser Pro Arg Val Ser Val Thr Asp Asp Ser Trp Leu Gly
1               5                   10

(2) INFORMATION FOR SEQ ID NO:25:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

Asn Ala Ile Phe Leu Thr Val Ser Arg Glu His Glu Arg Val Gly Cys
1               5                   10                  15

(2) INFORMATION FOR SEQ ID NO:26:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

Leu His Gly Tyr Leu Glu Asn Glu Pro Leu Met Leu Gln Leu Phe Ile
1               5                   10                  15

Gly Thr (2) INFORMATION FOR SEQ ID NO:27:

(i) SEQUENCE CHARACTERISTICS:
        (A) LENGTH: 16 amino acids
        (B) TYPE: amino acid (C) STRANDEDNESS:
        (D) TOPOLOGY: linear (ii) MOLECULE TYPE: peptide (xi) SEQUENCE DESCRIPTION: SEQ ID NO:27:

Pro Ser Thr Ser Pro Arg Ala Ser Val Thr Glu Glu Ser Trp Leu Gly
1               5                   10                  15

(2) INFORMATION FOR SEQ ID NO:28:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

Gly Pro Ala Pro Arg Ala Gly Gly Thr Met Lys Ser Ala Glu Glu Glu
1               5                   10                  15

His Tyr Gly (2) INFORMATION FOR SEQ ID NO:29:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

Ala Ser Ala Gly Gly His Pro Ile Val Gln
1               5                   10

(2) INFORMATION FOR SEQ ID NO:30:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

Asn Thr Arg Val Arg Leu Val Phe Arg Val
1               5                   10

(2) INFORMATION FOR SEQ ID NO:31:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

Ala Lys Thr Asp Arg Asp Leu Cys Lys Pro Asn Ser Leu Val Val Glu
1               5                   10                  15

Ile Pro Pro Phe Arg Asn
            20

(2) INFORMATION FOR SEQ ID NO:32:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
Glu Val Gln Pro Lys Ser His His Arg Ala His Tyr Glu Thr Glu Gly
 1               5                  10                  15
Ser Arg
```

(2) INFORMATION FOR SEQ ID NO:33:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
Ser Pro Arg Val Ser Val Thr Asp Asp Ser Trp Leu Gly Asn Thr
 1               5                  10                  15
```

(2) INFORMATION FOR SEQ ID NO:34:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

```
Ser His His Arg Ala His Tyr Glu Thr Glu Gly Ser Arg Gly Ala Val
 1               5                  10                  15
```

(2) INFORMATION FOR SEQ ID NO:35:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
Leu Arg Asn Ser Asp Ile Glu Leu Arg Lys Gly Glu Thr Asp Ile Gly
 1               5                  10                  15
Arg
```

(2) INFORMATION FOR SEQ ID NO:36:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

Thr Leu Ser Leu Gln Val Ala Ser Asn Pro Ile Glu Cys
1               5                   10

(2) INFORMATION FOR SEQ ID NO:37:

(i) SEQUENCE CHARACTERISTICS:
       (A) LENGTH: 13 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:37:

Val Lys Ala Ser Ala Gly Gly His Pro Ile Val Gln Leu
1               5                   10

(2) INFORMATION FOR SEQ ID NO:38:

(i) SEQUENCE CHARACTERISTICS:
       (A) LENGTH: 716 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:38:

Met Pro Ser Thr Ser Phe Pro Val Pro Ser Lys Phe Pro Leu Gly Pro
1               5                   10                  15

Ala Ala Ala Val Phe Gly Arg Gly Glu Thr Leu Gly Pro Ala Pro Arg
                20                  25                  30

Ala Gly Gly Thr Met Lys Ser Ala Glu Glu His Tyr Gly Tyr Ala
            35                  40                  45

Ser Ser Asn Val Ser Pro Ala Leu Pro Leu Pro Thr Ala His Ser Thr
    50                  55                  60

Leu Pro Ala Pro Cys His Asn Leu Gln Thr Ser Thr Pro Gly Ile Ile
65                  70                  75                  80

Pro Pro Ala Asp His Pro Ser Gly Tyr Gly Ala Ala Leu Asp Gly Cys
                85                  90                  95

Pro Ala Gly Tyr Phe Leu Ser Ser Gly His Thr Arg Pro Asp Gly Ala
                100                 105                 110

Pro Ala Leu Glu Ser Pro Arg Ile Glu Ile Thr Ser Cys Leu Gly Leu
            115                 120                 125

Tyr His Asn Asn Asn Gln Phe Phe His Asp Val Glu Val Glu Asp Val
    130                 135                 140

Leu Pro Ser Ser Lys Arg Ser Pro Ser Thr Ala Thr Leu Ser Leu Pro
145                 150                 155                 160

Ser Leu Glu Ala Tyr Arg Asp Pro Ser Cys Leu Ser Pro Ala Ser Ser
                165                 170                 175

Leu Ser Ser Arg Ser Cys Asn Ser Glu Ala Ser Ser Tyr Glu Ser Asn
            180                 185                 190

Tyr Ser Tyr Pro Tyr Ala Ser Pro Gln Thr Ser Pro Trp Gln Ser Pro
    195                 200                 205

Cys Val Ser Pro Lys Thr Thr Asp Pro Glu Glu Gly Phe Pro Arg Gly
    210                 215                 220

Leu Gly Ala Cys Thr Leu Leu Gly Ser Pro Gln His Ser Pro Ser Thr
225                 230                 235                 240

```
Ser Pro Arg Ala Ser Val Thr Glu Glu Ser Trp Leu Gly Ala Arg Ser
            245                 250                 255

Ser Arg Pro Ala Ser Pro Cys Asn Lys Arg Lys Tyr Ser Leu Asn Gly
            260                 265                 270

Arg Gln Pro Pro Tyr Ser Pro His His Ser Pro Thr Pro Ser Pro His
            275                 280                 285

Gly Ser Pro Arg Val Ser Val Thr Asp Asp Ser Trp Leu Gly Asn Thr
            290                 295                 300

Thr Gln Tyr Thr Ser Ser Ala Ile Val Ala Ala Ile Asn Ala Leu Thr
305                 310                 315                 320

Thr Asp Ser Ser Leu Asp Leu Gly Asp Gly Val Pro Val Lys Ser Arg
            325                 330                 335

Lys Thr Thr Leu Glu Gln Pro Pro Ser Val Ala Leu Lys Val Glu Pro
            340                 345                 350

Val Gly Glu Asp Leu Gly Ser Pro Pro Pro Ala Asp Phe Ala Pro
            355                 360                 365

Glu Asp Tyr Ser Ser Phe Gln His Ile Arg Lys Gly Gly Phe Cys Asp
            370                 375                 380

Gln Tyr Leu Ala Val Pro Gln His Pro Tyr Gln Trp Ala Lys Pro Lys
385                 390                 395                 400

Pro Leu Ser Pro Thr Ser Tyr Met Ser Pro Thr Leu Pro Ala Leu Asp
            405                 410                 415

Trp Gln Leu Pro Ser His Ser Gly Pro Tyr Glu Leu Arg Ile Glu Val
            420                 425                 430

Gln Pro Lys Ser His His Arg Ala His Tyr Glu Thr Glu Gly Ser Arg
            435                 440                 445

Gly Ala Val Lys Ala Ser Ala Gly Gly His Pro Ile Val Gln Leu His
450                 455                 460

Gly Tyr Leu Glu Asn Glu Pro Leu Met Leu Gln Leu Phe Ile Gly Thr
465                 470                 475                 480

Ala Asp Asp Arg Leu Leu Arg Pro His Ala Phe Tyr Gln Val His Arg
            485                 490                 495

Ile Thr Gly Lys Thr Val Ser Thr Thr Ser His Glu Ala Ile Leu Ser
            500                 505                 510

Asn Thr Lys Val Leu Glu Ile Pro Leu Leu Pro Glu Asn Ser Met Arg
            515                 520                 525

Ala Val Ile Asp Cys Ala Cys Ile Leu Lys Leu Arg Asn Ser Asp Ile
            530                 535                 540

Glu Leu Arg Lys Gly Glu Thr Asp Ile Gly Arg Lys Asn Thr Arg Val
545                 550                 555                 560

Arg Leu Val Phe Arg Val His Val Pro Gln Pro Ser Gly Arg Thr Leu
            565                 570                 575

Ser Leu Gln Val Ala Ser Asn Pro Ile Glu Cys Ser Gln Arg Ser Ala
            580                 585                 590

Gln Glu Leu Pro Leu Val Glu Lys Gln Ser Thr Asp Ser Tyr Pro Val
            595                 600                 605

Val Gly Gly Lys Lys Met Val Leu Ser Gly His Asn Phe Leu Gln Asp
            610                 615                 620

Ser Lys Val Ile Phe Val Glu Lys Ala Pro Asp Gly His His Val Trp
625                 630                 635                 640

Glu Met Glu Ala Lys Thr Asp Arg Asp Leu Cys Lys Pro Asn Ser Leu
            645                 650                 655

Val Val Glu Ile Pro Pro Phe Arg Asn Gln Arg Ile Thr Ser Pro Val
```

His Val Ser Phe Tyr Val Cys Asn Gly Lys Arg Lys Arg Ser Gln Tyr
        675                 680                 685

Gln Arg Phe Thr Tyr Leu Pro Ala Asn Gly Asn Ala Ile Phe Leu Thr
        690                 695                 700

Val Ser Arg Glu His Glu Arg Val Gly Cys Phe Phe
705                 710                 715

(2) INFORMATION FOR SEQ ID NO:39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:39:

ACGCCCAAAG AGGAAAATTT GTTTCATACA                             30

(2) INFORMATION FOR SEQ ID NO:40:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

Leu Arg Asn Ala Asp Ile Glu Leu Arg
1               5

(2) INFORMATION FOR SEQ ID NO:41:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

Gly Glu Thr Asp Ile Gly
1               5

(2) INFORMATION FOR SEQ ID NO:42:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

Arg Asn Ala Asp Ile Glu
1               5

(2) INFORMATION FOR SEQ ID NO:43:

(i) SEQUENCE CHARACTERISTICS:

(A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(ix) FEATURE:
            (A) NAME/KEY: misc_feature
            (B) LOCATION: one-of(3, 9)
            (D) OTHER INFORMATION: /product= "inosine"

(xi) SEQUENCE DESCRIPTION: SEQ ID NO:43:

MGNAAYGCNG AYATHGAR                                                      18

(2) INFORMATION FOR SEQ ID NO:44:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(ix) FEATURE:
            (A) NAME/KEY: misc_feature
            (B) LOCATION: one-of(1, 10, 16)
            (D) OTHER INFORMATION: /product= "inosine"

(xi) SEQUENCE DESCRIPTION: SEQ ID NO:44:

NCCDATRTCN GTYTCNCC                                                      18

(2) INFORMATION FOR SEQ ID NO:45:

(i) SEQUENCE CHARACTERISTICS:
            (A) LENGTH: 2751 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 240..2387

(xi) SEQUENCE DESCRIPTION: SEQ ID NO:45:

GAATTCCGCA GGGCGCGGGC ACCGGGGCGC GGGCAGGGCT CGGAGCCACC GCGCAGGTCC          60

TAGGGCCGCG GCCGGGCCCC GCCACGCGCG CACACGCCCC TCGATGACTT TCCTCCGGGG         120

CGCGCGGCGC TGAGCCCGGG GCGAGGGCTG TCTTCCCGGA GACCCGACCC CGGCAGCGCG         180

GGGCGGCCAT TTCTCCTGTG CCTCCGCCCG CTGCTCCACT CCCCGCCGCC GCCGCGCGG          239

ATG CCA AGC ACC AGC TTT CCA GTC CCT TCC AAG TTT CCA CTT GGC CCT           287
Met Pro Ser Thr Ser Phe Pro Val Pro Ser Lys Phe Pro Leu Gly Pro
 1               5                  10                  15

GAG GCT GCG GTC TTC GGG AGA GGA GAA ACT TTG GGG CCC GCG CCG CGC           335
Glu Ala Ala Val Phe Gly Arg Gly Glu Thr Leu Gly Pro Ala Pro Arg
                20                  25                  30

GCC GGC GGC ACC ATG AAG TCA GCG GAG GAA GAA CAC TAT GGC TAT GCA           383
Ala Gly Gly Thr Met Lys Ser Ala Glu Glu Glu His Tyr Gly Tyr Ala
            35                  40                  45

TCC TCC AAC GTC AGC CCC GCC CTG CCG CTC CCC ACG GCG CAC TCC ACC           431
Ser Ser Asn Val Ser Pro Ala Leu Pro Leu Pro Thr Ala His Ser Thr
        50                  55                  60

```
                                                              -continued

CTG CCG GCC CCG TGC CAC AAC CTT CAG ACC TCC ACA CCG GGC ATC ATC      479
Leu Pro Ala Pro Cys His Asn Leu Gln Thr Ser Thr Pro Gly Ile Ile
 65                  70                  75                  80

CCG CCG GCG GAC CAC CCC TCG GGG TAC GGA GCA GCT TTG GAC GGT GGG      527
Pro Pro Ala Asp His Pro Ser Gly Tyr Gly Ala Ala Leu Asp Gly Gly
                     85                  90                  95

CCC GCG GGC TAC TTC CTC TCC TCC GGC CAC ACC AGG CCT GAT CGG GCC      575
Pro Ala Gly Tyr Phe Leu Ser Ser Gly His Thr Arg Pro Asp Arg Ala
            100                 105                 110

CCT GCC CTG GAG AGT CCT CGC ATC GAG ATA ACC TCG TGC TTG GGC CTG      623
Pro Ala Leu Glu Ser Pro Arg Ile Glu Ile Thr Ser Cys Leu Gly Leu
                115                 120                 125

TAC CAC AAC AAT AAC CAG TTT TTC CAC GAT GTG GAG GTG GAA GAC GTC      671
Tyr His Asn Asn Asn Gln Phe Phe His Asp Val Glu Val Glu Asp Val
130                 135                 140

CTC CCT AGC TCC AAA CGG TCC CCC TCC ACG GCC ACG CTG AGT CTG CCC      719
Leu Pro Ser Ser Lys Arg Ser Pro Ser Thr Ala Thr Leu Ser Leu Pro
145                 150                 155                 160

AGC CTG GAG GCC TAC AGA GAC CCC TCG TGC CTG AGC CCG GCC AGC AGC      767
Ser Leu Glu Ala Tyr Arg Asp Pro Ser Cys Leu Ser Pro Ala Ser Ser
                165                 170                 175

CTG TCC TCC CGG AGC TGC AAC TCA GAG GCC TCC TCC TAC GAG TCC AAC      815
Leu Ser Ser Arg Ser Cys Asn Ser Glu Ala Ser Ser Tyr Glu Ser Asn
            180                 185                 190

TAC TCG TAC CCG TAC GCG TCC CCC CAG ACG TCG CCA TGG CAG TCT CCC      863
Tyr Ser Tyr Pro Tyr Ala Ser Pro Gln Thr Ser Pro Trp Gln Ser Pro
        195                 200                 205

TGC GTG TCT CCC AAG ACC ACG GAC CCC GAG GAG GGC TTT CCC CGC GGG      911
Cys Val Ser Pro Lys Thr Thr Asp Pro Glu Glu Gly Phe Pro Arg Gly
210                 215                 220

CTG GGG GCC TGC ACA CTG CTG GGT TCC CCG CAG CAC TCC CCC TCC ACC      959
Leu Gly Ala Cys Thr Leu Leu Gly Ser Pro Gln His Ser Pro Ser Thr
225                 230                 235                 240

TCG CCC CGC GCC AGC GTC ACT GAG GAG AGC TGG CTG GGT GCC CGC TCC     1007
Ser Pro Arg Ala Ser Val Thr Glu Glu Ser Trp Leu Gly Ala Arg Ser
                245                 250                 255

TCC AGA CCC GCG TCC CCT TGC AAC AAG AGG AAG TAC AGC CTC AAC GGC     1055
Ser Arg Pro Ala Ser Pro Cys Asn Lys Arg Lys Tyr Ser Leu Asn Gly
            260                 265                 270

CGG CAG CCG CCC TAC TCA CCC CAC CAC TCG CCC ACG CCG TCC CCG CAC     1103
Arg Gln Pro Pro Tyr Ser Pro His His Ser Pro Thr Pro Ser Pro His
        275                 280                 285

GGC TCC CCG AGG GTC AGC GTG ACC GAC GAC TCG TGG TTG GGC AAC ACC     1151
Gly Ser Pro Arg Val Ser Val Thr Asp Asp Ser Trp Leu Gly Asn Thr
    290                 295                 300

ACC CAG TAC ACC AGC TCG GCC ATC GTG GCC GCC ATC AAC GAG CTG ACC     1199
Thr Gln Tyr Thr Ser Ser Ala Ile Val Ala Ala Ile Asn Glu Leu Thr
305                 310                 315                 320

ACC GAC AGC AGC CTG GAC CTG GGA GAT GGC GTC CCT GTC AAG TCC CGC     1247
Thr Asp Ser Ser Leu Asp Leu Gly Asp Gly Val Pro Val Lys Ser Arg
                325                 330                 335

AAG ACC ACC CTG GAG CAG CAG CCC TCA GTG GCG CTC AAG GTG GAG CCC     1295
Lys Thr Thr Leu Glu Gln Gln Pro Ser Val Ala Leu Lys Val Glu Pro
            340                 345                 350

GTC GGG GAG GAC CTG GGC AGC CCC CCG CCG CCG GCC GAC TTC GCG CCC     1343
Val Gly Glu Asp Leu Gly Ser Pro Pro Pro Pro Ala Asp Phe Ala Pro
        355                 360                 365

GAA GAC TAC TCC TCT TTC CAG CAC ATC AGG AAG GGC GGC TTC TGC GAC     1391
Glu Asp Tyr Ser Ser Phe Gln His Ile Arg Lys Gly Gly Phe Cys Asp
370                 375                 380
```

```
CAG TAC CTG GCG GTG CCG CAG CAC CCC TAC CAG TGG GCG AAG CCC AAG      1439
Gln Tyr Leu Ala Val Pro Gln His Pro Tyr Gln Trp Ala Lys Pro Lys
385                 390                 395                 400

CCC CTG TCC CCT ACG TCC TAC ATG AGC CCG ACC CTG CCC GCC CTG GAC      1487
Pro Leu Ser Pro Thr Ser Tyr Met Ser Pro Thr Leu Pro Ala Leu Asp
            405                 410                 415

TGG CAG CTG CCG TCC CAC TCA GGC CCG TAT GAG CTT CGG ATT GAG GTG      1535
Trp Gln Leu Pro Ser His Ser Gly Pro Tyr Glu Leu Arg Ile Glu Val
                420                 425                 430

CAG CCC AAG TCC CAC CAC CGA GCC CAC TAC GAG ACG GAG GGC AGC CGG      1583
Gln Pro Lys Ser His His Arg Ala His Tyr Glu Thr Glu Gly Ser Arg
        435                 440                 445

GGG GCA GTG AAG GCG TCG GCC GGA GGA CAC CCC ATC GTG CAG CTG CAT      1631
Gly Ala Val Lys Ala Ser Ala Gly Gly His Pro Ile Val Gln Leu His
450                 455                 460

GGC TAC TTG GAG AAT GAG CCG CTG ATG CTG CAG CTT TTC ATT GGG ACG      1679
Gly Tyr Leu Glu Asn Glu Pro Leu Met Leu Gln Leu Phe Ile Gly Thr
465                 470                 475                 480

GCG GAC GAC CGC CTG CTG CGC CCG CAC GCC TTC TAC CAG GTG CAC CGC      1727
Ala Asp Asp Arg Leu Leu Arg Pro His Ala Phe Tyr Gln Val His Arg
            485                 490                 495

ATC ACA GGG AAG ACC GTG TCC ACC ACC AGC CAC GAG GCT ATC CTC TCC      1775
Ile Thr Gly Lys Thr Val Ser Thr Thr Ser His Glu Ala Ile Leu Ser
                500                 505                 510

AAC ACC AAA GTC CTG GAG ATC CCA CTC CTG CCG GAG AAC AGC ATG CGA      1823
Asn Thr Lys Val Leu Glu Ile Pro Leu Leu Pro Glu Asn Ser Met Arg
        515                 520                 525

GCC GTC ATT GAC TGT GCC GGA ATC CTG AAA CTC AGA AAC TCC GAC ATT      1871
Ala Val Ile Asp Cys Ala Gly Ile Leu Lys Leu Arg Asn Ser Asp Ile
530                 535                 540

GAA CTT CGC AAA GGA GAG ACG GAC ATC GGG AGG AAG AAC ACA CGG GTA      1919
Glu Leu Arg Lys Gly Glu Thr Asp Ile Gly Arg Lys Asn Thr Arg Val
545                 550                 555                 560

CGG CTG GTG TTC CGC GTT CAC GTC CCG CAA CCC AGC GGC CGC ACG CTG      1967
Arg Leu Val Phe Arg Val His Val Pro Gln Pro Ser Gly Arg Thr Leu
            565                 570                 575

TCC CTG CAG GTG GCC TCC AAC CCC ATC GAA TGC TCC CAG CGC TCA GCT      2015
Ser Leu Gln Val Ala Ser Asn Pro Ile Glu Cys Ser Gln Arg Ser Ala
                580                 585                 590

CAG GAG CTG CCT CTG GTG GAG AAG CAG AGC ACG GAC AGC TAT CCG GTC      2063
Gln Glu Leu Pro Leu Val Glu Lys Gln Ser Thr Asp Ser Tyr Pro Val
        595                 600                 605

GTG GGC GGG AAG AAG ATG GTC CTG TCT GGC CAC AAC TTC CTG CAG GAC      2111
Val Gly Gly Lys Lys Met Val Leu Ser Gly His Asn Phe Leu Gln Asp
610                 615                 620

TCC AAG GTC ATT TTC GTG GAG AAA GCC CCA GAT GGC CAC CAT GTC TGG      2159
Ser Lys Val Ile Phe Val Glu Lys Ala Pro Asp Gly His His Val Trp
625                 630                 635                 640

GAG ATG GAA GCG AAA ACT GAC CGG GAC CTG TGC AAG CCG AAT TCT CTG      2207
Glu Met Glu Ala Lys Thr Asp Arg Asp Leu Cys Lys Pro Asn Ser Leu
            645                 650                 655

GTG GTT GAG ATC CCG CCA TTT CGG AAT CAG AGG ATA ACC AGC CCC GTT      2255
Val Val Glu Ile Pro Pro Phe Arg Asn Gln Arg Ile Thr Ser Pro Val
                660                 665                 670

CAC GTC AGT TTC TAC GTC TGC AAC GGG AAG AGA AAG GGA AGC CAG TAC      2303
His Val Ser Phe Tyr Val Cys Asn Gly Lys Arg Lys Gly Ser Gln Tyr
        675                 680                 685

CAG CGT TTC ACC TAC CTT CCC GCC AAC GGT AAC GCC ATC TTT CTA ACC      2351
Gln Arg Phe Thr Tyr Leu Pro Ala Asn Gly Asn Ala Ile Phe Leu Thr
```

```
            690                 695                 700
GTA AGC CGT GAA CAT GAG CGC GTG GGG TGC TTT TTC TAAAGACGCA           2397
Val Ser Arg Glu His Glu Arg Val Gly Cys Phe Phe
705                 710                 715

GAAACGACGT CGCCGTAAAG CAGCGTGGCG TGTTGCACAT TTAACTGTGT GATGTCCCGT    2457

TAGTGAGACC GAGCCATCGA TGCCCTGAAA AGGAAAGGAA AAGGGAAGCT TCGGATGCAT    2517

TTTCCTTGAT CCCTGTTGGG GGTGGGGGGC GGGGGTTGCA TACTCAGATA GTCACGGTTA   2577

TTTTGCTTCT TGCGAATGTA TAACAGCCAA GGGGAAAACA TGGCTCTTCT GCTCCAAAAA    2637

ACTGAGGGGG TCCTGGTGTG CATTTGCACC CTAAAGCTGC TTACGGTGAA AAGGCAAATA   2697

GGTATAGCTA TTTTGCAGGC ACCTTTAGGA ATAAACTTTG CTTTTAAAAA AAAA          2751
```

(2) INFORMATION FOR SEQ ID NO:46:

(i) SEQUENCE CHARACTERISTICS:
        (A) LENGTH: 716 amino acids
        (B) TYPE: amino acid
        (D) TOPOLOGY: linear (ii) MOLECULE TYPE: protein (xi) SEQUENCE DESCRIPTION: SEQ ID NO:46:

```
Met Pro Ser Thr Ser Phe Pro Val Pro Ser Lys Phe Pro Leu Gly Pro
 1               5                  10                  15

Glu Ala Ala Val Phe Gly Arg Gly Glu Thr Leu Gly Pro Ala Pro Arg
                20                  25                  30

Ala Gly Gly Thr Met Lys Ser Ala Glu Glu His Tyr Gly Tyr Ala
            35                  40                  45

Ser Ser Asn Val Ser Pro Ala Leu Pro Leu Pro Thr Ala His Ser Thr
 50                  55                  60

Leu Pro Ala Pro Cys His Asn Leu Gln Thr Ser Thr Pro Gly Ile Ile
 65                  70                  75                  80

Pro Pro Ala Asp His Pro Ser Gly Tyr Gly Ala Ala Leu Asp Gly Gly
                85                  90                  95

Pro Ala Gly Tyr Phe Leu Ser Ser Gly His Thr Arg Pro Asp Arg Ala
                100                 105                 110

Pro Ala Leu Glu Ser Pro Arg Ile Glu Ile Thr Ser Cys Leu Gly Leu
                115                 120                 125

Tyr His Asn Asn Asn Gln Phe Phe His Asp Val Glu Val Glu Asp Val
 130                 135                 140

Leu Pro Ser Ser Lys Arg Ser Pro Ser Thr Ala Thr Leu Ser Leu Pro
145                 150                 155                 160

Ser Leu Glu Ala Tyr Arg Asp Pro Ser Cys Leu Ser Pro Ala Ser Ser
                165                 170                 175

Leu Ser Arg Ser Cys Asn Ser Glu Ala Ser Ser Tyr Glu Ser Asn
                180                 185                 190

Tyr Ser Tyr Pro Tyr Ala Ser Pro Gln Thr Ser Pro Trp Gln Ser Pro
                195                 200                 205

Cys Val Ser Pro Lys Thr Thr Asp Pro Glu Glu Gly Phe Pro Arg Gly
                210                 215                 220

Leu Gly Ala Cys Thr Leu Leu Gly Ser Pro Gln His Ser Pro Ser Thr
225                 230                 235                 240

Ser Pro Arg Ala Ser Val Thr Glu Glu Ser Trp Leu Gly Ala Arg Ser
                245                 250                 255

Ser Arg Pro Ala Ser Pro Cys Asn Lys Arg Lys Tyr Ser Leu Asn Gly
```

-continued

```
                    260                 265                 270
Arg Gln Pro Pro Tyr Ser Pro His His Ser Pro Thr Pro Ser Pro His
                275                 280                 285
Gly Ser Pro Arg Val Ser Val Thr Asp Asp Ser Trp Leu Gly Asn Thr
            290                 295                 300
Thr Gln Tyr Thr Ser Ser Ala Ile Val Ala Ile Asn Glu Leu Thr
305                 310                 315                 320
Thr Asp Ser Ser Leu Asp Leu Gly Asp Gly Val Pro Val Lys Ser Arg
                325                 330                 335
Lys Thr Thr Leu Glu Gln Gln Pro Ser Val Ala Leu Lys Val Glu Pro
                340                 345                 350
Val Gly Glu Asp Leu Gly Ser Pro Pro Pro Ala Asp Phe Ala Pro
            355                 360                 365
Glu Asp Tyr Ser Ser Phe Gln His Ile Arg Lys Gly Gly Phe Cys Asp
            370                 375                 380
Gln Tyr Leu Ala Val Pro Gln His Pro Tyr Gln Trp Ala Lys Pro Lys
385                 390                 395                 400
Pro Leu Ser Pro Thr Ser Tyr Met Ser Pro Thr Leu Pro Ala Leu Asp
                405                 410                 415
Trp Gln Leu Pro Ser His Ser Gly Pro Tyr Glu Leu Arg Ile Glu Val
                420                 425                 430
Gln Pro Lys Ser His His Arg Ala His Tyr Glu Thr Glu Gly Ser Arg
                435                 440                 445
Gly Ala Val Lys Ala Ser Ala Gly Gly His Pro Ile Val Gln Leu His
            450                 455                 460
Gly Tyr Leu Glu Asn Glu Pro Leu Met Leu Gln Leu Phe Ile Gly Thr
465                 470                 475                 480
Ala Asp Asp Arg Leu Leu Arg Pro His Ala Phe Tyr Gln Val His Arg
                485                 490                 495
Ile Thr Gly Lys Thr Val Ser Thr Thr Ser His Glu Ala Ile Leu Ser
                500                 505                 510
Asn Thr Lys Val Leu Glu Ile Pro Leu Leu Pro Glu Asn Ser Met Arg
                515                 520                 525
Ala Val Ile Asp Cys Ala Gly Ile Leu Lys Leu Arg Asn Ser Asp Ile
            530                 535                 540
Glu Leu Arg Lys Gly Glu Thr Asp Ile Gly Arg Lys Asn Thr Arg Val
545                 550                 555                 560
Arg Leu Val Phe Arg Val His Val Pro Gln Pro Ser Gly Arg Thr Leu
                565                 570                 575
Ser Leu Gln Val Ala Ser Asn Pro Ile Glu Cys Ser Gln Arg Ser Ala
            580                 585                 590
Gln Glu Leu Pro Leu Val Glu Lys Gln Ser Thr Asp Ser Tyr Pro Val
            595                 600                 605
Val Gly Gly Lys Lys Met Val Leu Ser Gly His Asn Phe Leu Gln Asp
            610                 615                 620
Ser Lys Val Ile Phe Val Glu Lys Ala Pro Asp Gly His His Val Trp
625                 630                 635                 640
Glu Met Glu Ala Lys Thr Asp Arg Asp Leu Cys Lys Pro Asn Ser Leu
                645                 650                 655
Val Val Glu Ile Pro Pro Phe Arg Asn Gln Arg Ile Thr Ser Pro Val
            660                 665                 670
His Val Ser Phe Tyr Val Cys Asn Gly Lys Arg Lys Gly Ser Gln Tyr
            675                 680                 685
```

```
Gln Arg Phe Thr Tyr Leu Pro Ala Asn Gly Asn Ala Ile Phe Leu Thr
    690                 695                 700

Val Ser Arg Glu His Glu Arg Val Gly Cys Phe Phe
705                 710                 715
```

(2) INFORMATION FOR SEQ ID NO:47:

(i) SEQUENCE CHARACTERISTICS:
      (A) LENGTH: 302 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:47:

```
Thr Lys Asn Val Glu Lys Lys Pro Tyr Val Lys Ile Thr Glu Gln Pro
1               5                   10                  15

Ala Gly Lys Ala Leu Arg Phe Pro Tyr Glu Cys Glu Gly Arg Ser Ala
                20                  25                  30

Gly Ser Ile Pro Gly Val Asn Xaa Thr Pro Glu Asn Lys Thr Tyr Pro
            35                  40                  45

Thr Xaa Xaa Xaa Val Gly Tyr Lys Gly Arg Ala Val Val Val Ser
    50                  55                  60

Cys Val Thr Lys Asp Thr Pro Tyr Arg Pro His Pro His Asn Leu Val
65                  70                  75                  80

Gly Lys Glu Gly Cys Xaa Lys Gly Val Cys Thr Leu Glu Ile Asn Ser
                85                  90                  95

Glu Xaa Xaa Arg Xaa Val Phe Ser Asn Leu Gly Ile Gln Cys Xaa Lys
            100                 105                 110

Lys Lys Asp Xaa Glu Ala Ala Leu Lys Ala Arg Glu Glu Ile Arg Val
            115                 120                 125

Leu Pro Phe Lys Thr Gly Phe Ser His Arg Pro Gln Pro Ser Xaa Ile
    130                 135                 140

Asp Leu Asn Ser Val Arg Leu Cys Phe Gln Val Pro Xaa Glu Xaa Xaa
145                 150                 155                 160

Gln Lys Gly Arg Phe Thr Ser Pro Leu Pro Pro Val Val Ser Xaa Pro
                165                 170                 175

Ile Phe Asp Lys Lys Ala Met Ser Asp Leu Val Ile Cys Arg Leu Cys
            180                 185                 190

Xaa Cys Ser Ala Xaa Val Pro Gly Asn Thr Gln Xaa Xaa Leu Leu Cys
    195                 200                 205

Glu Xaa Val Ala Lys Xaa Asp Ile Ser Val Arg Phe Glu Glu Lys
    210                 215                 220

Asn Gly Gln Ser Val Trp Glu Ala Phe Gly Asp Phe Gln His Thr Asp
225                 230                 235                 240

Val His Lys Gln Thr Xaa Xaa Thr Phe Lys Thr Pro Arg Xaa Xaa Thr
                245                 250                 255

Leu Asp Ile Thr Glu Pro Ala Lys Val Phe Ile Gln Leu Arg Arg Pro
            260                 265                 270

Xaa Asp Gly Val Thr Ser Xaa Ala Leu Pro Phe Glu Tyr Xaa Pro Met
    275                 280                 285

Xaa Xaa Xaa Xaa Ala His Leu Arg Arg Lys Arg Xaa Xaa Thr
    290                 295                 300
```

(2) INFORMATION FOR SEQ ID NO:48:

(i) SEQUENCE CHARACTERISTICS:
    (A) LENGTH: 297 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:48:

```
Met Ala Xaa Xaa Leu Tyr Asn Pro Tyr Ile Glu Ile Ile Glu Gln Pro
1               5                   10                  15

Xaa Gln Lys Gly Met Arg Phe Pro Tyr Glu Cys Glu Gly Arg Ser Ala
            20                  25                  30

Gly Xaa Xaa Pro Gln Glu His Xaa Xaa Asp Asn Asn Arg Thr Tyr Pro
        35                  40                  45

Ser Xaa Xaa Xaa Met Asn Tyr Tyr Gly Arg Gly Lys Val Arg Xaa Thr
    50                  55                  60

Leu Val Thr Lys Asn Asp Pro Tyr Xaa Pro His Pro His Asp Leu Val
65                  70                  75                  80

Gly Lys Asp Cys Arg Asp Gly Tyr Tyr Glu Xaa Glu Phe Xaa Asn Glu
                85                  90                  95

Arg Arg Pro Leu Phe Phe Gln Asn Leu Gly Ile Arg Cys Xaa Lys Lys
            100                 105                 110

Lys Glu Xaa Xaa Glu Ala Ile Ile Thr Arg Ile Lys Ala Gly Ile Asn
            115                 120                 125

Xaa Phe Asn Val Pro Glu Lys Gln Leu Asn Asp Ile Glu Asp Cys Asp
130                 135                 140

Leu Asn Val Val Arg Leu Cys Phe Gln Val Pro Leu Glu Pro Xaa Glu
145                 150                 155                 160

His Gly Asn Leu Thr Thr Ala Leu Pro Pro Val Val Ser Asn Pro Ile
                165                 170                 175

Tyr Xaa Asn Arg Ala Pro Asn Xaa Ala Glu Leu Arg Xaa Cys Arg Val
                180                 185                 190

Asn Lys Xaa Cys Gly Xaa Val Arg Gly Gly Asp Glu Xaa Phe Leu Leu
            195                 200                 205

Cys Asp Xaa Val Gln Lys Xaa Asp Ile Glu Val Arg Phe Val Leu Asn
210                 215                 220

Asp Trp Glu Ala Lys Xaa Ile Phe Ser Xaa Ala Asp Xaa His Xaa Gln
225                 230                 235                 240

Val Xaa Xaa Val Phe Lys Thr Pro Pro Xaa Cys Lys Ala Ile Thr Glu
                245                 250                 255

Pro Val Thr Val Met Lys Gln Leu Arg Arg Pro Xaa Asp Gln Glu Val
                260                 265                 270

Ser Xaa Ser Met Asp Phe Arg Tyr Leu Pro Asp Xaa Lys Xaa Xaa Tyr
    275                 280                 285

Gly Asn Asn Ala Lys Xaa Xaa Xaa Thr
290                 295
```

(2) INFORMATION FOR SEQ ID NO:49:

(i) SEQUENCE CHARACTERISTICS:
        (A) LENGTH: 331 amino acids
        (B) TYPE: amino acid
        (C) STRANDEDNESS:
        (D) TOPOLOGY: linear (ii) MOLECULE TYPE: peptide -continued (xi) SEQUENCE DESCRIPTION: SEQ ID NO:49:

```
Ile Pro Leu Ser Thr Asp Gly Pro Tyr Leu Gln Ile Leu Glu Gln Pro
 1               5                  10                  15
Lys Gln Xaa Gly Phe Arg Phe Xaa Tyr Val Cys Glu Gly Pro Ser Xaa
             20                  25                  30
Gly Xaa Xaa Pro Gly Xaa Xaa Xaa Glu Lys Asn Lys Lys Ser Tyr Pro
         35                  40                  45
Ser Val Lys Xaa Cys Asn Tyr Val Gly Pro Ala Lys Xaa Xaa Xaa Gln
 50                  55                  60
Leu Val Thr Asn Gly Lys Val Ile Xaa Leu His Ala His Ser Leu Val
 65                  70                  75                  80
Gly Lys His Cys Glu Asp Gly Val Cys Thr Val Thr Ala Xaa Pro Lys
                 85                  90                  95
Asp Xaa Xaa Val Gly Phe Ala Asn Leu Gly Ile Leu His Xaa Xaa Lys
            100                 105                 110
Lys Lys Val Phe Glu Thr Leu Glu Ala Arg Asn Thr Glu Ala Cys Ile
            115                 120                 125
Arg Gly Tyr Asn Pro Gly Leu Leu Val His Ser Asp Leu Ala Tyr Leu
            130                 135                 140
Gln Ala Glu Gly Gly Gly Asp Arg Gln Leu Thr Asp Arg Glu Lys Glu
145                 150                 155                 160
Ile Ile Arg Gln Ala Ala Val Xaa Gln Thr Lys Glu Met Asp Leu Xaa
                165                 170                 175
Val Val Arg Leu Xaa Phe Thr Ala Phe Xaa Pro Xaa Xaa Xaa Gly Ser
            180                 185                 190
Phe Thr Arg Arg Leu Glu Pro Val Val Ser Xaa Xaa Ile Tyr Xaa Ser
            195                 200                 205
Lys Ala Pro Asn Ala Ser Xaa Leu Lys Ile Val Arg Met Asp Arg Thr
            210                 215                 220
Xaa Gly Cys Val Thr Gly Gly Glu Glu Xaa Tyr Leu Leu Cys Asp Xaa
225                 230                 235                 240
Val Gln Lys Xaa Asp Ile Gln Ile Arg Phe Tyr Glu Glu Glu Asn Gly
                245                 250                 255
Gly Val Trp Glu Gly Phe Gly Asp Phe Ser Pro Thr Asp Val His Xaa
            260                 265                 270
Gln Phe Ala Xaa Val Phe Lys Thr Pro Lys Xaa Xaa Xaa Val Asn Ile
            275                 280                 285
Thr Lys Pro Ala Ser Val Phe Val Gln Leu Arg Arg Lys Xaa Asp Leu
290                 295                 300
Glu Thr Ser Xaa Pro Lys Pro Phe Leu Tyr Tyr Pro Glu Ile Lys Xaa
305                 310                 315                 320
Lys Glu Glu Val Gln Arg Lys Xaa Xaa Leu
                325                 330
```

(2) INFORMATION FOR SEQ ID NO:50:

(i) SEQUENCE CHARACTERISTICS:
      (A) LENGTH: 296 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:50:

Xaa Pro Xaa Gln Ala Ser Gly Pro Tyr Val Glu Ile Ile Glu Gln Pro

```
1               5                   10                  15
Lys Gln Xaa Gly Met Arg Phe Xaa Tyr Lys Cys Glu Gly Arg Ser Ala
                20                  25                  30
Gly Xaa Xaa Pro Gly Glu Arg Xaa Xaa Asp Thr Thr Lys Thr His Pro
            35                  40                  45
Thr Xaa Lys Xaa Asn Gly Tyr Thr Gly Pro Gly Xaa Xaa Arg Xaa Ser
        50                  55                  60
Leu Val Thr Lys Asp Xaa Pro His Arg Pro Xaa Pro His Glu Leu Val
65                  70                  75                  80
Gly Lys Asp Cys Arg Asp Gly Tyr Tyr Glu Xaa Asp Leu Cys Pro Xaa
                85                  90                  95
Arg Asp Ser Xaa His Ser Phe Gln Asn Leu Gly Ile Gln Cys Xaa Lys
            100                 105                 110
Lys Arg Asp Leu Glu Gln Ala Ile Ser Gln Arg Ile Gln Thr Asn Asn
            115                 120                 125
Asn Xaa Phe His Val Pro Ile Glu Glu Gln Arg Gly Asp Tyr Asp Leu
    130                 135                 140
Xaa Ala Val Arg Leu Cys Phe Gln Val Thr Val Pro Arg Xaa Pro Ala
145                 150                 155                 160
Gly Arg Xaa Leu Leu Leu Thr Pro Val Leu Ser His Pro Ile Phe Xaa
                165                 170                 175
Asn Arg Ala Pro Asn Xaa Ala Glu Leu Lys Ile Cys Arg Val Asn Arg
            180                 185                 190
Xaa Ser Gly Ser Cys Xaa Gly Gly Asp Glu Xaa Phe Leu Leu Cys Asp
            195                 200                 205
Xaa Val Gln Lys Xaa Asp Ile Glu Val Tyr Phe Thr Gly Pro Gln Trp
    210                 215                 220
Glu Ala Arg Gly Ser Phe Ser Gly Ala Asp Val His Xaa Gln Val Ala
225                 230                 235                 240
Ile Val Phe Arg Thr Pro Pro Xaa Ala Xaa Pro Ser Xaa Gln Xaa Pro
                245                 250                 255
Val Xaa Val Ser Met Gln Leu Arg Arg Pro Xaa Asp Arg Glu Leu Ser
            260                 265                 270
Xaa Pro Met Glu Phe Gln Tyr Leu Pro Asp Thr Asp Xaa Arg His Arg
    275                 280                 285
Leu Glu Glu Lys Arg Lys Xaa Thr
    290                 295

(2) INFORMATION FOR SEQ ID NO:51:

(i) SEQUENCE CHARACTERISTICS:
        (A) LENGTH: 293 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:51:

Gln Leu Pro Ser His Ser Gly Pro Tyr Glu Leu Arg Ile Glu Val Gln
1               5                   10                  15
Pro Lys Ser His His Arg Ala His Tyr Glu Thr Glu Gly Ser Arg Gly
                20                  25                  30
Ala Val Lys Ala Ser Ala Gly Gly His Pro Ile Val Gln Leu His Gly
            35                  40                  45
Tyr Leu Glu Asn Glu Pro Leu Met Leu Gln Leu Phe Ile Gly Thr Ala
```

```
              50                  55                  60
Asp Asp Arg Leu Leu Arg Pro His Ala Phe Tyr Gln Val His Arg Ile
 65                      70                  75                  80

Thr Gly Lys Thr Val Ser Thr Thr Ser His Glu Ala Ile Leu Ser Asn
                     85                  90                  95

Thr Lys Val Leu Glu Ile Pro Leu Leu Pro Glu Asn Ser Met Arg Ala
                    100                 105                 110

Val Ile Asp Cys Ala Gly Ile Leu Lys Leu Arg Asn Ser Asp Ile Glu
                115                 120                 125

Leu Arg Lys Gly Glu Thr Asp Ile Gly Arg Lys Asn Thr Arg Val Arg
    130                 135                 140

Leu Val Phe Arg Val His Val Pro Gln Pro Ser Gly Arg Thr Leu Ser
145                 150                 155                 160

Leu Gln Val Ala Ser Asn Pro Ile Glu Cys Ser Gln Arg Ser Ala Gln
                165                 170                 175

Glu Leu Pro Leu Val Glu Lys Gln Ser Thr Asp Ser Tyr Pro Val Val
                180                 185                 190

Gly Gly Lys Lys Met Val Leu Ser Gly His Asn Phe Leu Gln Asp Ser
            195                 200                 205

Lys Val Ile Phe Val Glu Lys Ala Pro Asp Gly His His Val Trp Glu
    210                 215                 220

Met Glu Ala Lys Thr Asp Arg Asp Leu Cys Lys Pro Asn Ser Leu Val
225                 230                 235                 240

Val Glu Ile Pro Pro Phe Arg Asn Gln Arg Ile Thr Ser Pro Val His
                245                 250                 255

Val Ser Phe Tyr Val Cys Asn Gly Lys Arg Lys Gly Ser Gln Tyr Gln
                260                 265                 270

Arg Phe Thr Tyr Leu Pro Ala Asn Gly Asn Ala Ile Phe Leu Thr Val
                275                 280                 285

Ser Arg Glu His Glu
290

(2) INFORMATION FOR SEQ ID NO:52:

(i) SEQUENCE CHARACTERISTICS:
        (A) LENGTH: 293 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:52:

Pro Leu Xaa Asn Gln Ser Gly Gly Tyr Glu Leu Arg Ile Glu Val Gln
  1                   5                  10                  15

Pro Lys Arg His His Arg Ala His Tyr Glu Thr Glu Gly Ser Arg Gly
                 20                  25                  30

Ala Val Lys Ala Xaa Xaa Gly Gly His Pro Xaa Val Gln Leu His Gly
             35                  40                  45

Tyr Xaa Glu Asn Lys Pro Leu Gly Leu Gln Xaa Phe Ile Gly Thr Ala
 50                  55                  60

Asp Xaa Arg Xaa Leu Xaa Pro His Ala Phe Tyr Gln Val His Arg Ile
 65                  70                  75                  80

Thr Gly Lys Thr Val Thr Thr Thr Ser Tyr Glu Lys Ile Xaa Xaa Asn
                 85                  90                  95

Thr Lys Val Leu Glu Ile Pro Leu Glu Pro Lys Asn Ser Met Arg Ala
```

```
                    100                 105                 110
Val Ile Asp Cys Ala Gly Ile Leu Lys Leu Arg Asn Xaa Asp Ile Glu
            115                 120                 125

Leu Arg Lys Gly Glu Thr Asp Ile Gly Arg Lys Asn Thr Arg Val Arg
    130                 135                 140

Leu Val Phe Arg Val His Val Pro Xaa Pro Ser Gly Arg Ile Xaa Ser
145                 150                 155                 160

Leu Gln Ala Ala Ser Asn Pro Ile Glu Cys Ser Gln Arg Ser Ala His
                165                 170                 175

Glu Leu Pro Xaa Val Glu Xaa Gln Asp Met Asp Gly Cys Leu Val Tyr
            180                 185                 190

Gly Gly Gln Gln Met Xaa Leu Xaa Gly Gln Asn Phe Thr Ala Xaa Ser
        195                 200                 205

Lys Val Val Phe Xaa Glu Lys Xaa Xaa Asp Gly Gln Gln Ile Trp Glu
    210                 215                 220

Met Glu Ala Thr Val Asp Lys Asp Lys Ser Gln Pro Asn Asn Leu Phe
225                 230                 235                 240

Val Glu Ile Pro Glu Xaa Arg Asn Lys His Ile Arg Val Pro Val Lys
                245                 250                 255

Val Asn Phe Tyr Val Ile Asn Gly Lys Arg Lys Gly Ser Gln Pro Gln
            260                 265                 270

His Phe Thr Tyr His Pro Val Pro Ala Ile Lys Thr Glu Pro Xaa Asp
        275                 280                 285

Glu Tyr Glu Pro Gly
    290

(2) INFORMATION FOR SEQ ID NO:53:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:53:

Cys Asn Lys Arg Lys Tyr Ser Leu Asn
1               5

(2) INFORMATION FOR SEQ ID NO:54:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:54:

Gly Lys Arg Lys Lys
1               5

(2) INFORMATION FOR SEQ ID NO:55:

(i) SEQUENCE CHARACTERISTICS:
        (A) LENGTH: 4 amino acids
        (B) TYPE: amino acid
        (C) STRANDEDNESS:
        (D) TOPOLOGY: linear
```

(ii) MOLECULE TYPE: peptide (xi) SEQUENCE DESCRIPTION: SEQ ID NO:55:

Thr Arg Thr Gly
1

(2) INFORMATION FOR SEQ ID NO:56:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:56:

Lys Arg Lys Lys
1

(2) INFORMATION FOR SEQ ID NO:57:

(i) SEQUENCE CHARACTERISTICS:
            (A) LENGTH: 25 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:57:

Cys Leu Ser Pro Ala Ser Ser Leu Ser Ser Arg Ser Cys Asn Ser Glu
1               5                   10                  15

Ala Ser Ser Tyr Glu Ser Asn Tyr Ser
            20                  25

(2) INFORMATION FOR SEQ ID NO:58:

(i) SEQUENCE CHARACTERISTICS:
            (A) LENGTH: 25 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:58:

Cys Leu Ala Pro Ala Ala Ala Leu Ala Ala Arg Ala Cys Asn Ala Glu
1               5                   10                  15

Ala Ala Ala Tyr Glu Ala Asn Tyr Ala
            20                  25

(2) INFORMATION FOR SEQ ID NO:59:

(i) SEQUENCE CHARACTERISTICS:
            (A) LENGTH: 25 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:59:

Cys Leu Ser Pro Ala Ser Ser Leu Ser Ser Arg Ser Cys Asn Ala Glu
1               5                   10                  15

Ala Ala Ala Tyr Glu Ala Asn Tyr Ala
            20                  25

(2) INFORMATION FOR SEQ ID NO:60:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:60:

```
Cys Leu Ala Pro Ala Ala Ala Leu Ser Ser Arg Ser Cys Asn Ser Glu
 1               5                  10                  15
Ala Ser Ser Tyr Glu Ser Asn Tyr Ser
            20                  25
```

(2) INFORMATION FOR SEQ ID NO:61:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:61:

```
Cys Leu Ser Pro Ala Ser Ser Leu Ala Ala Arg Ala Cys Asn Ser Glu
 1               5                  10                  15
Ala Ser Ser Tyr Glu Ser Asn Tyr Ser
            20                  25
```

(2) INFORMATION FOR SEQ ID NO:62:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:62:

```
Cys Leu Ser Pro Ala Ser Ser Leu Ser Ser Arg Ser Cys Asn Ala Glu
 1               5                  10                  15
Ala Ala Ala Tyr Glu Ser Asn Tyr Ser
            20                  25
```

(2) INFORMATION FOR SEQ ID NO:63:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:63:

```
Cys Leu Ser Pro Ala Ser Ser Leu Ser Ser Arg Ser Cys Asn Ser Glu
 1               5                  10                  15
Ala Ser Ser Tyr Glu Ala Asn Tyr Ala
            20                  25
```

(2) INFORMATION FOR SEQ ID NO:64:

(i) SEQUENCE CHARACTERISTICS:
    (A) LENGTH: 110 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:64:

```
Pro Tyr Ala Ser Pro Gln Thr Ser Pro Trp Gln Ser Pro Cys Val Ser
1               5                  10                 15
Pro Lys Thr Thr Asp Pro Glu Glu Gly Phe Pro Arg Gly Leu Gly Ala
            20                  25                 30
Cys Thr Leu Leu Gly Ser Pro Gln His Ser Pro Ser Thr Ser Pro Arg
            35                  40                 45
Ala Ser Val Thr Glu Glu Ser Trp Leu Gly Ala Arg Ser Ser Arg Pro
        50                  55                 60
Ala Ser Pro Cys Asn Lys Arg Lys Tyr Ser Leu Asn Gly Arg Gln Pro
65                  70                  75                 80
Pro Tyr Ser Pro His His Ser Pro Tyr Pro Ser Pro His Gly Ser Pro
                85                  90                 95
Arg Val Ser Val Thr Asp Asp Ser Trp Leu Gly Asn Thr Thr
                100                 105                110
```

(2) INFORMATION FOR SEQ ID NO:65:

(i) SEQUENCE CHARACTERISTICS:
    (A) LENGTH: 4 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:65:

Lys Arg Lys Arg
1

NFORMATION FOR SEQ ID NO:66:

(i) SEQUENCE CHARACTERISTICS:
    (A) LENGTH: 4 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 4
    (D) OTHER INFORMATION: /product= "Lys or Arg"

(xi) SEQUENCE DESCRIPTION: SEQ ID NO:66:

Lys Arg Lys Xaa
1

NFORMATION FOR SEQ ID NO:67:

(i) SEQUENCE CHARACTERISTICS:
    (A) LENGTH: 5 amino acids
    (B) TYPE: amino acid
    (C) STRANDEDNESS:
    (D) TOPOLOGY: linear (ii) MOLECULE TYPE: peptide

```
        (ix) FEATURE:
              (A) NAME/KEY: Modified-site
              (B) LOCATION: 5
              (D) OTHER INFORMATION: /product= "Lys or Arg"

(xi) SEQUENCE DESCRIPTION: SEQ ID NO:67:

Gly Lys Arg Lys Xaa
1               5

NFORMATION FOR SEQ ID NO:68:

(i) SEQUENCE CHARACTERISTICS:
              (A) LENGTH: 7 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:68:

Asn Gly Lys Arg Lys Arg Ser
1               5

NFORMATION FOR SEQ ID NO:69:

(i) SEQUENCE CHARACTERISTICS:
              (A) LENGTH: 7 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:69:

Asn Gly Lys Arg Lys Lys Ser
1               5

NFORMATION FOR SEQ ID NO:70:

(i) SEQUENCE CHARACTERISTICS:
              (A) LENGTH: 7 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:70:

Asn Gly Arg Arg Lys Arg Ser
1               5

NFORMATION FOR SEQ ID NO:71:

(i) SEQUENCE CHARACTERISTICS:
              (A) LENGTH: 13 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:71:

Ser Pro Cys Asn Lys Arg Lys Tyr Ser Leu Asn Gly Arg
1               5                   10

NFORMATION FOR SEQ ID NO:72:

(i) SEQUENCE CHARACTERISTICS:
```

(A) LENGTH: 9 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 7
          (D) OTHER INFORMATION: /product= "Lys or Arg"

(xi) SEQUENCE DESCRIPTION: SEQ ID NO:72:

Cys Asn Gly Lys Arg Lys Xaa Ser Gln
1               5

(2) INFORMATION FOR SEQ ID NO:73:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:73:

ACGCCCAAAG AGGAAAATTT GTTTCATACA                                          30

(2) INFORMATION FOR SEQ ID NO:74:

(i) SEQUENCE CHARACTERISTICS:
          (A) LENGTH: 17 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:74:

Leu Arg Asn Ser Asp Ile Glu Leu Arg Lys Gly Glu Thr Asp Ile Gly
1               5                   10                  15

Arg (2) INFORMATION FOR SEQ ID NO:75:

(i) SEQUENCE CHARACTERISTICS:
          (A) LENGTH: 9 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:75:

Leu Arg Asn Ala Asp Ile Glu Leu Arg
1               5

(2) INFORMATION FOR SEQ ID NO:76:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:76:

Gly Glu Thr Asp Ile Gly
1               5

(2) INFORMATION FOR SEQ ID NO:77:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:77:

Arg Asn Ala Asp Ile Glu
1               5

(2) INFORMATION FOR SEQ ID NO:78:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: one-of(3, 9)
        (D) OTHER INFORMATION: /product= "inosine"

(xi) SEQUENCE DESCRIPTION: SEQ ID NO:78:

MGNAAYGCNG AYATHGAR                                               18

(2) INFORMATION FOR SEQ ID NO:79:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: one-of(1, 10, 16)
        (D) OTHER INFORMATION: /product= "inosine"

(xi) SEQUENCE DESCRIPTION: SEQ ID NO:79:

NCCDATRTCN GTYTCNCC                                               18

(2) INFORMATION FOR SEQ ID NO:80:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:80:

CTAGTCCTAA GAAGAAGAGA AAGGTAT                                     27

(2) INFORMATION FOR SEQ ID NO:81:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:81:

CTAGTCCTAA GACGAAGAGA AAGGTAT                                           27

(2) INFORMATION FOR SEQ ID NO:82:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:82:

Leu Glu Cys Asn Lys Arg Lys Tyr Ser Leu Asn Val Asp
1               5                   10

(2) INFORMATION FOR SEQ ID NO:83:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:83:

Ala Ser Val Thr Glu Glu Ser Trp Leu Gly Ala Arg
1               5                   10

(2) INFORMATION FOR SEQ ID NO:84:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:84:

Gly Leu Gly Ala Cys Thr Leu Leu Gly Ser Pro Gln His Ser Pro Ser
1               5                   10                  15
Thr Ser Pro Arg
            20

(2) INFORMATION FOR SEQ ID NO:85:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide -continued

```
        (B) LOCATION: 1..6
        (D) OTHER INFORMATION: /product= "consensus sequence"

(xi) SEQUENCE DESCRIPTION: SEQ ID NO:85:

Ser Pro Xaa Xaa Ser Pro
1               5
```

What is claimed is:

1. A method for identifying a compound which modulates translocation of an NF-AT polypeptide across the nuclear membrane of a cell by binding of the compound to the NF-AT polypeptide, comprising
   (i) contacting test compounds with an NF-AT polypeptide, or portion thereof, wherein the NF-AT polypeptide is encoded by a nucleic acid which hybridizes to a nucleic acid having SEQ ID NO: 45 in 5×SSC at 42° C.;
   (ii) identifying those test compounds which bind to the NF-AT polypeptide; and
   (iii) determining which of the test compounds so identified modulates translocation of an NF-AT polypeptide across the nuclear membrane of a cell.

2. The method of claim 1, comprising identifying those test compounds which bind to a nuclear localization sequence (NLS) of the NF-AT polypeptide.

3. The method of claim 1, comprising identifying those test compounds which bind to a portion of the NF-AT polypeptide which binds to a NLS of the NF-AT polypeptide.

4. The method of claim 1, wherein the NF-AT polypeptide is a fusion polypeptide.

5. The method of claim 1, wherein the NF-AT polypeptide is a recombinantly produced NF-AT polypeptide.

6. The method of claim 2, wherein the NLS comprises the amino acid sequence KRK.

7. The method of claim 2, wherein the NLS comprises the amino acid sequence KRKK/R (SEQ ID NO: 66).

8. The method of claim 2, wherein the NLS comprises the amino acid sequence GKRKK/R (SEQ ID NO: 67).

9. The method of claim 2, wherein the NLS comprises the amino acid sequence NGRRKRS (SEQ ID NO: 70).

10. The method of claim 3, wherein the portion of an NF-AT polypeptide binding to said NLS comprises a sequence selected from the group consisting of about amino acids 170–192 of SEQ ID NO: 38, about amino acids 199–219 of SEQ ID NO: 38, about amino acids 233–252 of SEQ ID NO: 38, and about amino acids 278–301 of SEQ ID NO: 38.

11. The method of claim 3, wherein the portion of an NF-AT polypeptide binding to said NLS comprises an SRR.

12. The method of claim 3, wherein the portion of an NF-AT polypeptide binding to said NLS comprises at least one phosphoserine.

13. The method of claim 6, wherein the NLS comprises the amino acid sequence CNKRKYSLN (SEQ ID NO: 53).

14. The method of claim 10, wherein the portion of an NF-AT polypeptide binding to said NLS comprises at least three phosphoserines.

15. The method of claim 11, wherein the portion of an NF-AT polypeptide binding to said NLS comprises at least three phosphoserines.

16. The method of claim 15, wherein all the serines of the SRR are phosphorylated.

17. A method for identifying a compound which promotes or inhibits translocation of an NF-AT polypeptide across the nuclear membrane of a cell, comprising
   (i) providing a polypeptide complex comprising a nuclear localization sequence (NLS) of an NF-AT polypeptide and a portion of an NF-AT polypeptide which binds to said NLS, wherein the NF-AT polypeptide is encoded by a nucleic acid which hybridizes to a nucleic acid having SEQ ID NO: 45 in 5×SSC at 42° C.;
   (ii) contacting the polypeptide complex with test compounds and determining whether a test compound modulates the binding of the NLS to the portion of an NF-AT polypeptide which binds to said NLS; and
   (ii) determining which of the test compounds so identified promotes or inhibits translocation of an NF-AT polypeptide across the nuclear membrane of a cell.

18. The method of claim 17, wherein the portion of an NF-AT polypeptide which binds to said NLS is selected from the group consisting of SRR, SP1, SP2, and SP3.

19. The method of claim 17, wherein the NLS or the portion of an NF-AT polypeptide which binds to said NLS is a fusion polypeptide.

20. The method of claim 17, wherein the NLS or the portion of an NF-AT polypeptide which binds to said NLS is a recombinantly produced NF-AT polypeptide.

21. The method of claim 18, wherein the NLS is an N-terminal or C-terminal NLS.

22. The method of claim 18, wherein the portion of an NF-AT polypeptide binding to said NLS comprises a sequence selected from the group consisting of about amino acids 170–192 of SEQ ID NO: 38, about amino acids 199–219 of SEQ ID NO: 38, about amino acids 233–252 of SEQ ID NO: 38, and about amino acids 278–301 of SEQ ID NO: 38.

23. The method of claim 18, wherein the portion of an NF-AT polypeptide binding to said NLS is an SRR.

24. The method of claim 21, wherein the NLS is an N-terminal NLS and the portion of an NF-AT polypeptide binding to said NLS is an SRR.

25. The method of claim 21, wherein the NLS comprises the amino acid sequence KRK.

26. The method of claim 21, wherein the NLS comprises the amino acid sequence KRKK/R (SEQ ID NO: 66).

27. The method of claim 21, wherein the NLS comprises the amino acid sequence GKRKK/R (SEQ ID NO: 67).

28. The method of claim 21, wherein the NLS comprises the amino acid sequence NGRRKRS (SEQ ID NO: 70).

29. The method of claim 24, wherein the NLS comprises the amino acid sequence KRKK/R (SEQ ID NO: 66).

30. The method of claim 25, wherein the NLS comprises the amino acid sequence CNKRKYSLN (SEQ ID NO: 53).

31. A method for identifying a compound which promotes or inhibits phosphorylation of an NF-AT polypeptide, comprising
   (i) providing a reaction mixture comprising (a) an NF-AT polypeptide, or a portion thereof which contains a phosphorylation site and (b) a kinase or portion thereof sufficient to phosphorylate an NF-AT polypeptide, wherein the NF-AT polypeptide is encoded by a nucleic acid which hybridizes to a nucleic acid having SEQ ID NO: 45 in 5×SSC at 42° C.;

(ii) contacting the reaction mixture with test compounds under conditions permitting phosphorylation of said NF-AT polypeptide; and (iii) determining which of the test compounds promotes or inhibits phosphorylation of the NF-AT polypeptide.

32. The method of claim 31, wherein the kinase is glycogen synthase kinase-3 (GSK-3) or protein kinase A (PKA).

33. The method of claim 31, wherein the NF-AT polypeptide, or a portion thereof which contains a phosphorylation site, comprising an amino acid sequence from amino acids 172–301 of SEQ ID NO: 38.

34. The method of claim 31, wherein the NF-AT polypeptide is a fusion polypeptide.

35. The method of claim 31, wherein the NF-AT polypeptide is a recombinantly produced NF-AT polypeptide.

36. The method of claim 33, wherein the NF-AT polypeptide, or a portion thereof which contains a phosphorylation site, comprises an SRR, SP1, SP2, or SP3 sequence.

37. The method of claim 36, wherein the NF-AT polypeptide, or a portion thereof which contains a phosphorylation site, comprises a sequence selected from the group consisting of about amino acids 170–192 of SEQ ID NO: 38, about amino acids 199–219 of SEQ ID NO: 38, about amino acids 233–252 of SEQ ID NO: 38, and about amino acids 278–301 of SEQ ID NO: 38.

38. A method for identifying a compound which modulates dephosphorylation of an NF-AT polypeptide, comprising (i) providing a reaction mixture comprising (a) a phosphorylated NF-AT polypeptide, or a portion thereof comprising a phosphorylated serine residue, and (b) a phosphatase, or portion thereof sufficient to bind to a phosphorylated amino acid residue, wherein the NF-AT polypeptide is encoded by a nucleic acid which hybridizes to a nucleic acid having SEQ ID NO: 45 in 5×SSC at 42° C.;

(ii) contacting the reaction mixture with test compounds under conditions permitting dephosphorylation of said NF-AT polypeptide; and (iii) determining which of the test compounds modulates dephosphorylation of the NF-AT polypeptide.

39. The method of claim 38, wherein the phosphatase is calcineurin.

40. The method of claim 38, wherein the NF-AT polypeptide is a fusion polypeptide.

41. The method of claim 38, wherein the NF-AT polypeptide is a recombinantly produced NF-AT polypeptide.

42. A method for identifying a compound which modulates translocation of an NF-AT polypeptide across the nuclear membrane of a cell by binding of the compound to the NF-AT polypeptide, comprising (i) contacting test compounds with an NF-AT polypeptide, or portion thereof, wherein the NF-AT polypeptide, or portion thereof, wherein the NF-AT polypeptide comprises at least 25 contiguous amino acids having an amino acid sequence which is at least 80% identical to an amino acid sequence of SEQ ID NO: 38, wherein the percent identity is determined with the algorithm GAP, BESTFIT, or FASTA in the Wisconsin Genetics Software Package Release 7.0, using default gap weights;

(ii) identifying those test compounds which bind to the NF-AT polypeptide; and determining which of the test compounds so identified modulates translocation of an NF-AT polypeptide across the nuclear membrane of a cell.

43. The method of claim 42, wherein the NF-AT polypeptide comprises at least 25 contiguous amino acids having an amino acid sequence which is at least 90% identical to an amino acid sequence of SEQ ID NO: 38.

44. The method of claim 42, comprising identifying those test compounds which bind to a NLS of the NF-AT polypeptide.

45. The method of claim 42, comprising identifying those test compounds which bind to a portion of the NF-AT polypeptide which binds to a NLS of the NF-AT polypeptide.

46. The method of claim 42, wherein the NF-AT polypeptide is a fusion polypeptide.

47. The method of claim 42, wherein the NF-AT polypeptide is a recombinantly produced NF-AT polypeptide.

48. The method of claim 43, wherein the NF-AT polypeptide comprises at least 25 contiguous amino acids of SEQ ID NO: 38.

49. The method of claim 44, wherein the NLS comprises the amino acid sequence KRK.

50. The method of claim 44, wherein the NLS comprises the amino acid sequence KRKK/R (SEQ ID NO: 66).

51. The method of claim 44, wherein the NLS comprises the amino acid sequence GKRKK/R (SEQ ID NO: 67).

52. The method of claim 44, wherein the NLS comprises the amino acid sequence NGRRKRS (SEQ ID NO: 70).

53. The method of claim 45, wherein the portion of the NF-AT polypeptide which binds to an NLS comprises a sequence selected from the group consisting of about amino acids 170–192 of SEQ ID NO: 38, about amino acids 199–219 of SEQ ID NO: 38, about amino acids 233–252 of SEQ ID NO: 38, and about amino acids 278–301 of SEQ ID NO: 38.

54. The method of claim 45, wherein the portion of the NF-AT polypeptide which binds to an NLS comprises an SRR.

55. The method of claim 45, wherein the portion of the NF-AT polypeptide which binds to an NLS comprises at least one phosphoserine.

56. The method of claim 49, wherein the NLS comprises the amino acid sequence CNKRKYSLN (SEQ ID NO: 53).

57. The method of claim 53, wherein the portion of the NF-AT polypeptide which binds to an NLS comprises at least three phosphoserines.

58. The method of claim 54, wherein the portion of the NF-AT polypeptide which binds to an NLS comprises at least three phosphoserines.

59. The method of claim 58, wherein all the serines of the SRR are phosphorylated.

60. A method for identifying a compound which promotes or inhibits translocation of an NF-AT polypeptide across the nuclear membrane of a cell, comprising (i) providing a polypeptide complex comprising a nuclear localization sequence (NLS) of an NF-AT polypeptide and a portion of an NF-AT polypeptide which binds to said NLS, wherein the NF-AT polypeptide comprises at least 25 contiguous amino acids having an amino acid sequence which is at least 80% identical to an amino acid sequence of SEQ ID NO: 38, wherein the percent identity is determined with the algorithm GAP, BESTFIT, or FASTA in the Wisconsin Genetics Software Package Release 7.0, using default gap weights;

(ii) contacting the polypeptide complex with test compounds and determining whether a test compound modulates the binding of the NLS to the portion of an NF-AT polypeptide which binds to said NLS; and (iii) determining which of the test compounds so identified promotes or inhibits translocation of an NF-AT polypeptide across the nuclear membrane of a cell.

61. The method of claim 60, wherein the NF-AT polypeptide comprises at least 25 contiguous amino acids having an amino acid sequence which is at least 90% identical to an amino acid sequence of SEQ ID NO: 38.

62. The method of claim 60, wherein the portion of an NF-AT polypeptide which binds to said NLS is selected from the group consisting of SRR, SP1, SP2, and SP3.

63. The method of claim 60, wherein the NLS or the portion of an NF-AT polypeptide which binds to said NLS is a fusion polypeptide.

64. The method of claim 60, wherein the NLS or the portion of an NF-AT polypeptide which binds to said NLS is a recombinantly produced NF-AT polypeptide.

65. The method of claim 61, wherein the NF-AT polypeptide comprises at least 25 contiguous amino acids of SEQ ID NO: 38.

66. The method of claim 62, wherein the NLS is an N-terminal or C-terminal NLS.

67. The method of claim 62, wherein the portion of an NF-AT polypeptide which binds to said NLS comprises a sequence selected from the group consisting of about amino acids 170–192 of SEQ ID NO: 38, about amino acids 199–219 of SEQ ID NO: 38, about amino acids 233–252 of SEQ ID NO: 38, and about amino acids 278–301 of SEQ ID NO: 38.

68. The method of claim 62, wherein the portion of an NF-AT polypeptide which binds to said NLS is an SRR.

69. The method of claim 65, wherein the NLS is an N-terminal NLS and the portion of an NF-AT polypeptide binding to said NLS is an SRR.

70. The method of claim 66, wherein the NLS comprises the amino acid sequence KRK.

71. The method of claim 66, wherein the NLS comprises the amino acid sequence KRKK/R (SEQ ID NO: 66).

72. The method of claim 66, wherein the NLS comprises the amino acid sequence GKRKK/R (SEQ ID NO: 67).

73. The method of claim 66, wherein the NLS comprises the amino acid sequence NGRRKRS (SEQ ID NO: 70).

74. The method of claim 69, wherein the NLS comprises the amino acid sequence KRKK/R (SEQ ID NO: 66).

75. The method of claim 70, wherein the NLS comprises the amino acid sequence CNKRKYSLN (SEQ ID NO: 53).

76. A method for identifying a compound which promotes or inhibits phosphorylation of an NF-AT polypeptide, comprising (i) providing a reaction mixture comprising (a) an NF-AT polypeptide, or a portion thereof which contains a phosphorylation site and (b) a kinase or portion thereof sufficient to phosphorylate an NF-AT polypeptide, wherein the NF-AT polypeptide comprises at least 25 contiguous amino acids having an amino acid sequence which is at least 80% identical to an amino acid sequence of SEQ ID NO: 38, wherein the percent identity is determined with the algorithm GAP, BESTFIT, or FASTA in the Wisconsin Genetics Software Package Release 7.0, using default gap weights;

(ii) contacting the reaction mixture with test compounds under conditions permitting phosphorylation of said NF-AT polypeptide; and (iii) determining which of the test compounds promotes or inhibits phosphorylation of the NF-AT polypeptide.

77. The method of claim 76, wherein the NF-AT polypeptide comprises at least 25 contiguous amino acids having an amino acid sequence which is at least 90% identical to an amino acid sequence of SEQ ID NO: 38.

78. The method of claim 76, which the kinase is GSK-3 or PKA.

79. The method of claim 76, wherein the NF-AT polypeptide, or a portion thereof which contains a phosphorylation site, comprises an amino acid sequence from amino acids 172–301 of SEQ ID NO: 38.

80. The method of claim 76, wherein the NF-AT polypeptide is a fusion polypeptide.

81. The method of claim 76, wherein the NF-AT polypeptide is a recombinantly produced NF-AT polypeptide.

82. The method of claim 77, wherein the NF-AT polypeptide comprises at least 25 contiguous amino acids of SEQ ID NO: 38.

83. The method of claim 79, wherein the NF-AT polypeptide, or a portion thereof which contains a phosphorylation site, comprises an SRR, SP1, SP2, or SP3 sequence.

84. The method of claim 83, wherein the NF-AT polypeptide, or a portion thereof which contains a phosphorylation site, comprises a sequence selected from the group consisting of about amino acids 170–192 of SEQ ID NO: 38, amino acids 199–219 of SEQ ID NO: 38, amino acids 233–252 of SEQ ID NO: 38, and amino acids 278–301 of SEQ ID NO: 38.

85. A method for identifying a compound which modulates dephosphorylation of an NF-AT polypeptide, comprising (i) providing a reaction mixture comprising (a) a phosphorylated NF-AT polypeptide, or a portion thereof comprising a phosphorylated serine residue, and (b) a phosphatase, or portion thereof sufficient to bind to a phosphorylated amino acid residue, wherein the NF-AT polypeptide comprises at least 25 contiguous amino acids having an amino acid sequence which is at least 80% identical to an amino acid sequence of SEQ ID NO: 38, wherein the percent identity is determined with the algorithm GAP, BESTFIT, or FASTA in the Wisconsin Genetics Software Package Release 7.0, using default gap weights;

(ii) contacting the reaction mixture with a test compound under conditions permitting dephosphorylation of said NF-AT polypeptide and;

(iii) determining which of the compounds modulates dephosphorylation of the NF-AT polypeptide.

86. The method of claim 85, wherein the NF-AT polypeptide comprises at least 25 contiguous amino acids having an amino acid sequence which is at least 90% identical to an amino acid sequence of SEQ ID NO: 38.

87. The method of claim 85, wherein the phosphatase is calcineurin.

88. The method of claim 85, wherein the NF-AT polypeptide is a fusion polypeptide.

89. The method of claim 85, wherein the NF-AT polypeptide is a recombinantly produced NF-AT polypeptide.

90. The method of claim 86, wherein the NF-AT polypeptide comprises at least 25 contiguous amino acids of SEQ ID NO: 38.

* * * * *